(12) United States Patent
Carini et al.

(10) Patent No.: US 7,772,183 B2
(45) Date of Patent: Aug. 10, 2010

(54) HEPATITIS C VIRUS INHIBITORS

(75) Inventors: David J. Carini, Wallingford, CT (US); Barry L. Johnson, Wallingford, CT (US); Zhizhen Barbara Zheng, Cheshire, CT (US); Stanley D'Andrea, Wallingford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 784 days.

(21) Appl. No.: 11/546,505

(22) Filed: Oct. 11, 2006

(65) Prior Publication Data

US 2007/0093414 A1   Apr. 26, 2007

Related U.S. Application Data

(60) Provisional application No. 60/725,673, filed on Oct. 12, 2005.

(51) Int. Cl.
    *A61K 38/00*    (2006.01)
(52) U.S. Cl. .......................................................... 514/9
(58) Field of Classification Search ........................ None
    See application file for complete search history.

(56) References Cited

U.S. PATENT DOCUMENTS

| 2005/0153877 | A1 | 7/2005 | Miao et al. | |
| 2005/0153900 | A1* | 7/2005 | Velazquez et al. | 514/18 |
| 2005/0164921 | A1* | 7/2005 | Njoroge et al. | 514/9 |
| 2006/0172950 | A1 | 8/2006 | Wang et al. | |
| 2006/0199773 | A1 | 9/2006 | Sausker et al. | |
| 2006/0257980 | A1 | 11/2006 | Li | |

FOREIGN PATENT DOCUMENTS

| WO | WO 98/17679 | 4/1998 |
|---|---|---|
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/060926 | 8/2002 |
| WO | WO 03/053349 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |

(Continued)

OTHER PUBLICATIONS

Tsantrizos et al, "Macrocyclic Inhibitors of the NS3 Protease as Potential Therapeutic Agents of Hepatitis C Virus Infection," Angew. Chem. Int. Ed. (2003), vol. 42, pp. 1356-136.*

(Continued)

*Primary Examiner*—Cecilia Tsang
*Assistant Examiner*—Thomas S Heard
(74) *Attorney, Agent, or Firm*—Warren K. Volles; Pamela A. Mingo

(57) ABSTRACT

Hepatitis C virus inhibitors having the general formula

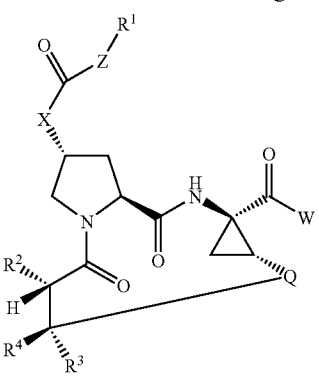

are disclosed. Compositions comprising the compounds and methods for using the compounds to inhibit HCV are also disclosed.

19 Claims, No Drawings

FOREIGN PATENT DOCUMENTS

| | | |
|---|---|---|
| WO | WO 2006/130552 | 12/2006 |
| WO | WO 2006/130553 | 12/2006 |
| WO | WO 2006/130554 | 12/2006 |
| WO | WO 2006/130626 | 12/2006 |
| WO | WO 2006/130627 | 12/2006 |
| WO | WO 2006/130686 | 12/2006 |
| WO | WO 2006/130687 | 12/2006 |
| WO | WO 2007/001406 | 1/2007 |
| WO | WO 2006/130666 | 12/2008 |

OTHER PUBLICATIONS

U.S. Appl. No. 11/481,536, filed Jul. 6, 2006, Hewawasam et al.

Lauer G. M. et al., "Hepatitis C Virus Infection," New England Journal of Medicine, vol. 345 No. 1, pp. 41-52, (2001).

Poupart, M.-A. et al., "Solid-Phase Synthesis of Peptidomimetic Inhibitors for the Hepatitis C Virus NS3 Protease," The Journal of Organic Chemistry, vol. 66 No. 14, pp. 4743-4751, (2001).

U.S. Appl. No. 11/591,293, filed Nov. 1, 2006, D'Andrea et al.

\* cited by examiner

HEPATITIS C VIRUS INHIBITORS

CROSS-REFERENCE TO RELATED APPLICATIONS

This application claims the benefit of U.S. Provisional Application Ser. No. 60/725,673 filed Oct. 12, 2005.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with another compound having anti-HCV activity, e.g., a compound which is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In one aspect the present disclosure provides a compound of formula (I)

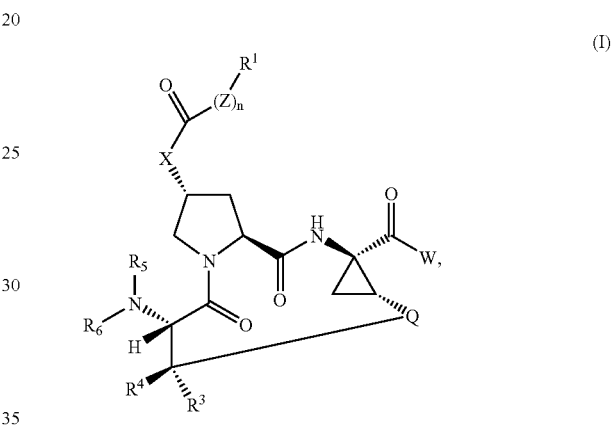

(I)

or a pharmaceutically acceptable salt thereof, wherein $R^1$ is selected from hydrogen, alkoxyalkyl, alkyl, aryl, arylalkyl, cyanoalkyl, cycloalkyl, (cycloalkyl)alkyl, dialkylaminoalkyl, haloalkoxyalkyl, haloalkyl, heterocyclyl, heterocyclylalkyl, and hydroxyalkyl;

$R^3$ and $R^4$ are independently selected from hydrogen, alkoxyalkyl, alkyl, haloalkoxyalkyl, and haloalkyl;

$R^5$ is selected from hydrogen, alkyl and haloalkyl;

$R^6$ is selected from hydrogen, alkyl, alkoxycarbonyl, alkylaminocarbonyl, alkylcarbonyl, aminocarbonyl, aryloxycarbonyl, cycloalkyloxycarbonyl, dialkylaminocarbonyl, haloalkoxycarbonyl, haloalkyl, and heterocyclylcarbonyl;

Q is a $C_{3-9}$ saturated or unsaturated chain optionally containing from one to three heteroatoms independently selected from O, $S(O)_m$, and $NR^7$; wherein m is 0, 1, or 2, and $R^7$ is selected from hydrogen, alkoxy, alkoxycarbonyl, alkyl, alkylcarbonyl, alkylsulfonyl, aminocarbonyl, arylsulfonyl, cycloalkyl, (cycloalkyl)alkyl, cycloalkyloxy, dialkylaminocarbonyl, dialkylaminocarbonylalkyl, haloalkyl, and heterocyclylcarbonyl;

W is selected from alkoxy, hydroxy, and —$NHSO_2R^8$; wherein $R^8$ is selected from alkyl, aryl, cycloalkyl, (cycloalkyl)alkyl, dialkylaminocarbonyl, dialkylaminocarbonylalkyl, heterocyclyl, heterocyclylcarbonyl, and —$NR^aR^b$; wherein the cycloalkyl is optionally substituted with one group selected from alkyl, alkoxy, halo, haloalkyl, cyano, cyanoalkyl, and haloalkoxy; and wherein $R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl;

X is selected from O and NH;

n is 0 or 1; and

Z is selected from O and NR$^9$; wherein R$^9$ is selected from hydrogen, alkyl, aryl, arylalkyl, cycloalkyl, (cycloalkyl)alkyl, and heterocyclyl; provided that when Q contains zero heteroatoms, and W is other than —NHSO$_2$NR$^a$R$^b$, then n is 1.

In another aspect the present disclosure provides a compound of formula (I), or a pharmaceutically acceptable salt thereof, wherein X is O.

In another aspect the present disclosure provides a compound of formula (I), or a pharmaceutically acceptable salt thereof, wherein W is —NHSO$_2$R$^8$.

In another embodiment the present disclosure provides a compound of formula (II),

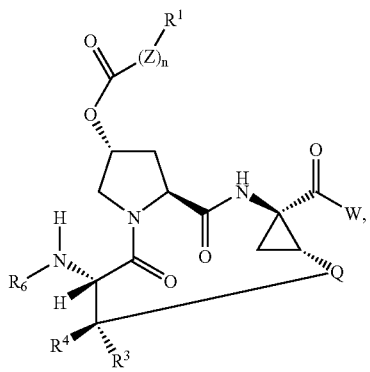

(II)

or a pharmaceutically acceptable salt thereof, wherein

R$^1$ is selected from alkyl, aryl, arylalkyl, cycloalkyl, (cycloalkyl)alkyl, heterocyclyl, and heterocyclylalkyl;

R$^3$ and R$^4$ are independently selected from hydrogen and alkyl;

R$^6$ is selected from alkoxycarbonyl, alkylaminocarbonyl, alkylcarbonyl, aminocarbonyl, arylcarbonyl, cycloalkyloxycarbonyl, dialkylaminocarbonyl, and heterocyclylcarbonyl;

Q is a C$_{5-6}$ saturated or unsaturated chain optionally containing one or two heteroatoms independently selected from O and NR$^7$; wherein R$^7$ is selected from hydrogen, alkoxy, alkoxycarbonyl, alkyl, alkylcarbonyl, cycloalkyl, (cycloalkyl)alkyl, cycloalkyloxy, dialkylaminocarbonyl, and haloalkyl;

W is —NHSO$_2$R$^8$; wherein R$^8$ is selected from alkyl, aryl, cycloalkyl, (cycloalkyl)alkyl, heterocyclyl, and —NR$^a$R$^b$; wherein the cycloalkyl is optionally substituted with one group selected from alkyl, alkoxy, halo, haloalkyl, and cyano; and wherein R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl;

n is 0 or 1; and

Z is NR$^9$; wherein R$^9$ is selected from hydrogen, alkyl, aryl, arylalkyl, cycloalkyl, (cycloalkyl)alkyl, and heterocyclyl;

provided that when Q contains zero heteroatoms, and W is other than —NHSO$_2$NR$^a$R$^b$, then n is 1.

In another embodiment the present disclosure provides a compound of formula (II), or a pharmaceutically acceptable salt thereof, wherein R$^3$ and R$^4$ are each hydrogen.

In another embodiment the present disclosure provides a compound of formula (II), or a pharmaceutically acceptable salt thereof, wherein R$^6$ is alkoxycarbonyl.

In another embodiment the present disclosure provides a compound of formula (III),

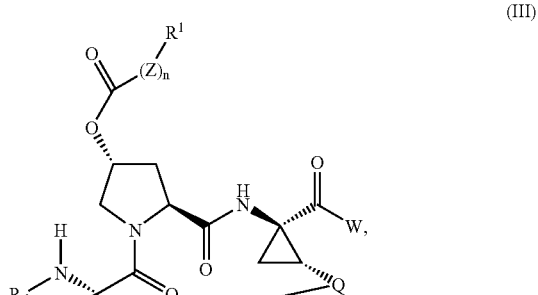

(III)

or a pharmaceutically acceptable salt thereof, wherein

R$^1$ is selected from alkyl, aryl, arylalkyl, cycloalkyl, (cycloalkyl)alkyl, and heterocyclyl;

R$^6$ is alkoxycarbonyl;

Q is a C$_{5-6}$ unsaturated chain optionally containing one heteroatom selected from O and NR$^7$; wherein R$^7$ is selected from hydrogen and cycloalkyl;

W is —NHSO$_2$R$^8$; wherein R$^8$ is cycloalkyl;

n is 0 or 1; and

Z is NR$^9$; wherein R$^9$ is selected from hydrogen, alkyl, aryl, arylalkyl, cycloalkyl, (cycloalkyl)alkyl, and heterocyclyl;

provided that when Q contains zero heteroatoms, and W is other than —NHSO$_2$NR$^a$R$^b$, then n is 1.

In another embodiment the present disclosure provides a compound of formula (III), or a pharmaceutically acceptable salt thereof, wherein Q contains no heteroatoms.

In another embodiment the present disclosure provides a compound of formula (III), or a pharmaceutically acceptable salt thereof, wherein Q contains one heteroatom.

In another embodiment the present disclosure provides a compound selected from

Compound 1

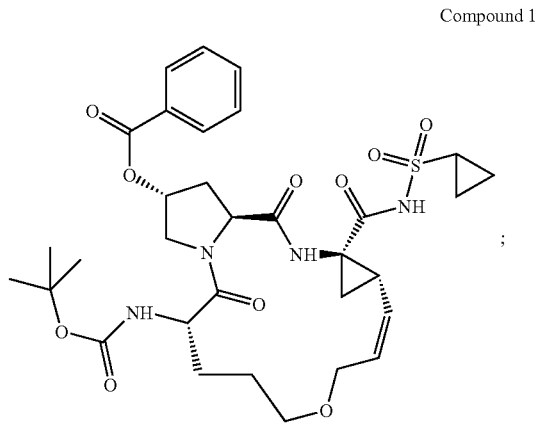

Compound 2
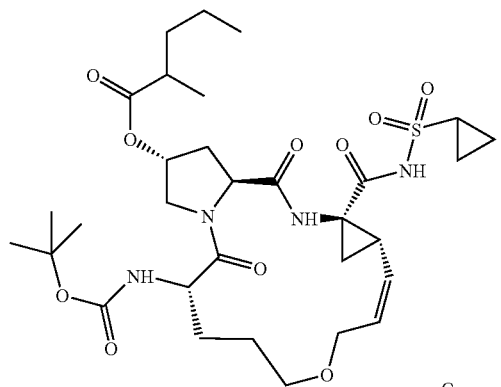
Compound 3
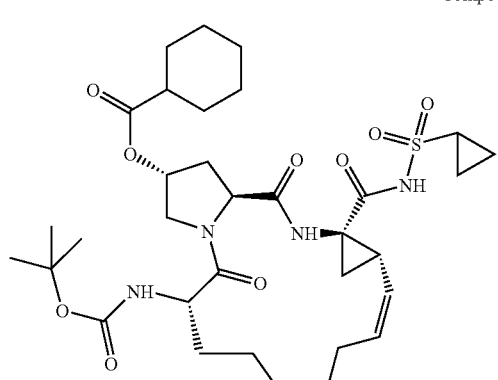
Compound 4
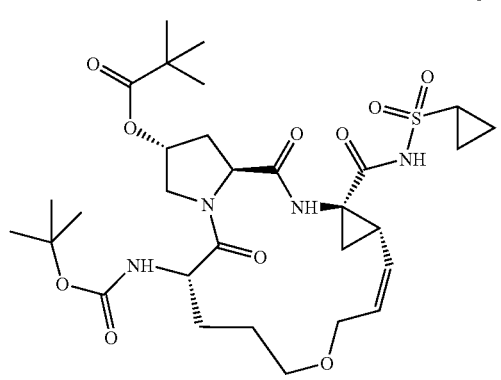
Compound 5
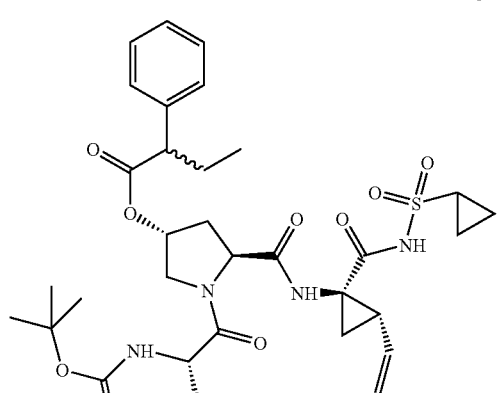
Compound 6
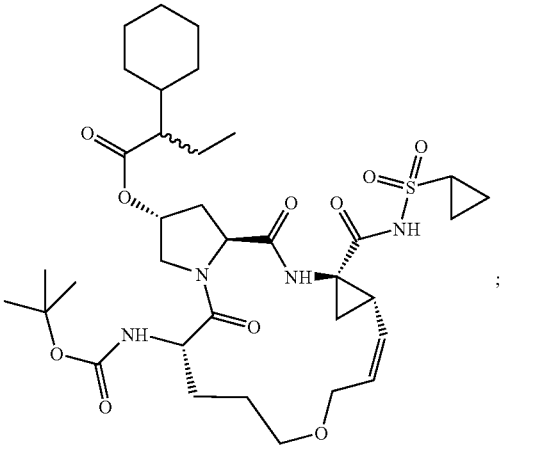
Compound 7
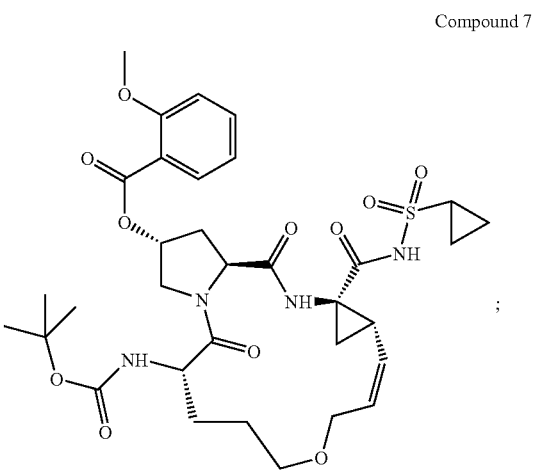
Compound 8
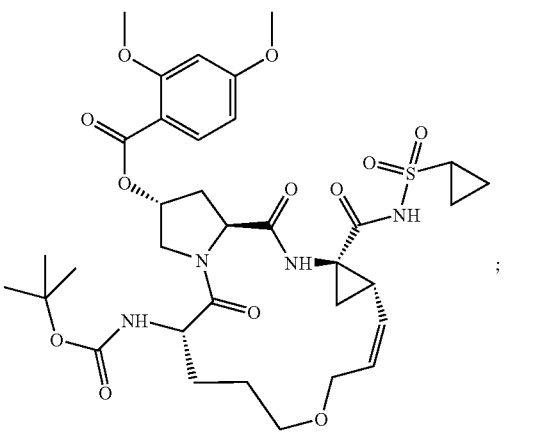

-continued
Compound 9
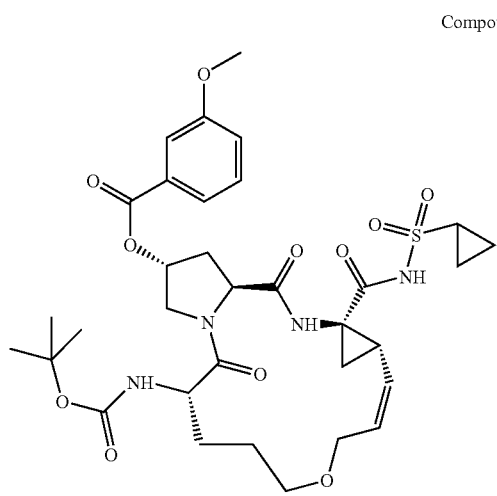
Compound 10
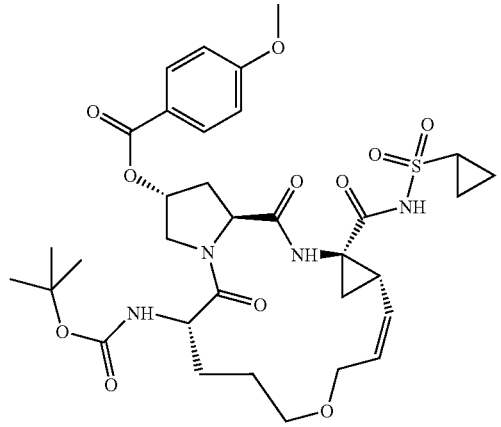
Compound 11
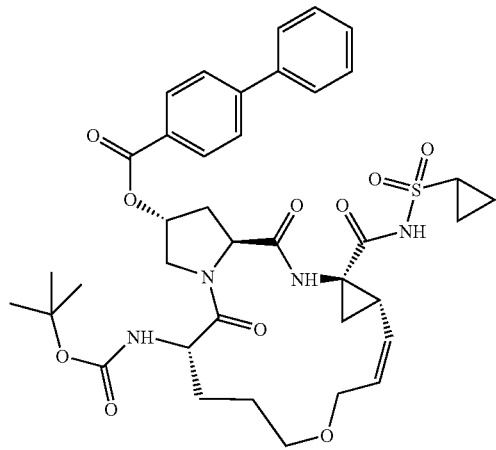
-continued
Compound 12
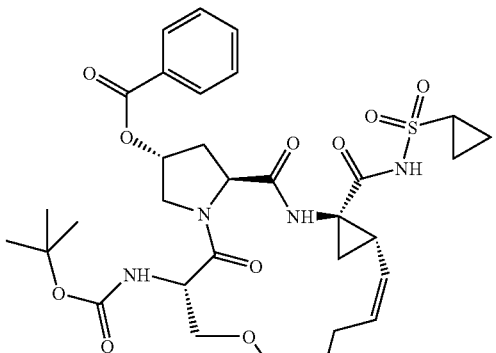
Compound 13
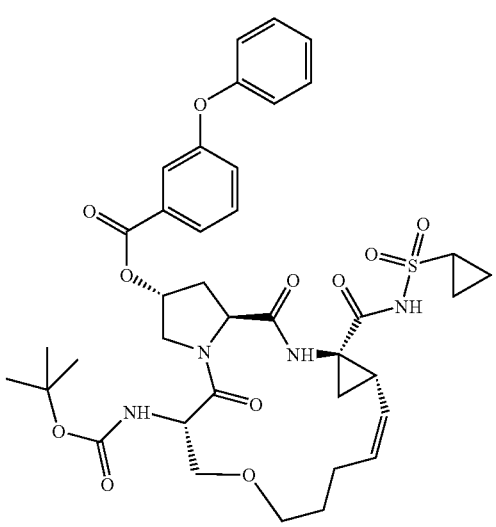
Compound 14
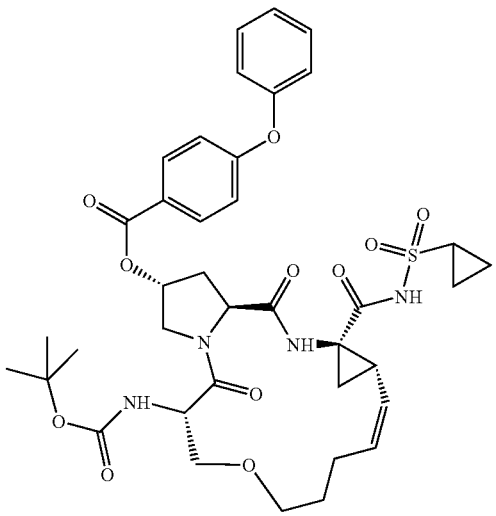

-continued

Compound 37

Compound 38

Compound 39

Compound 40

Compound 41

Compound 42

Compound 43
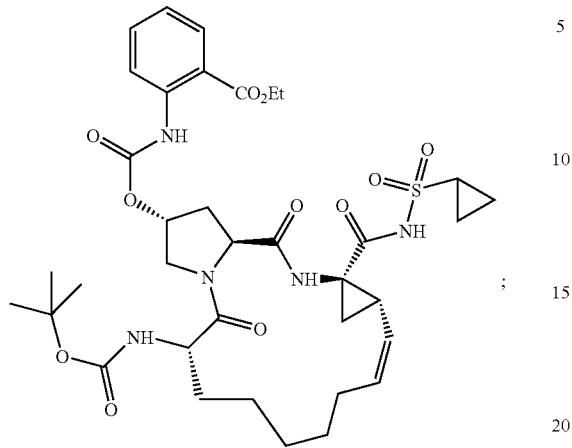
Compound 44
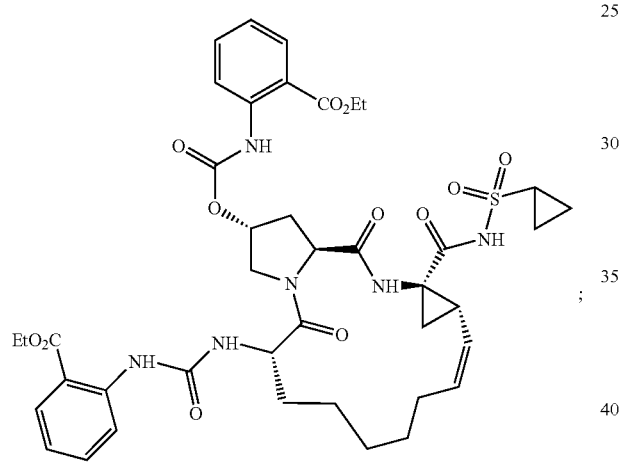
Compound 45
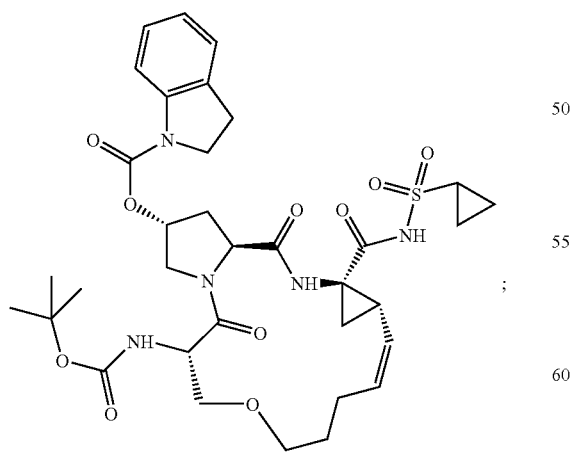
Compound 46
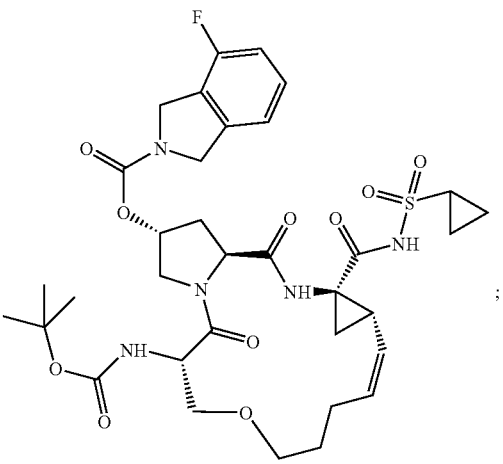
Compound 47
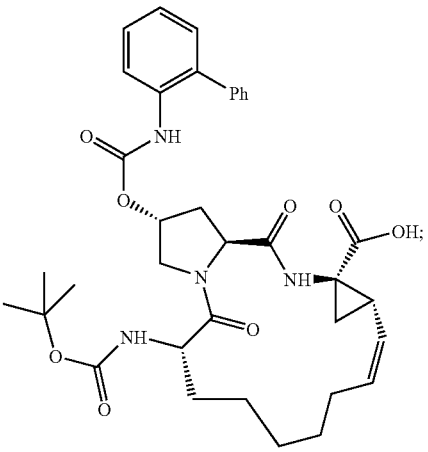
Compound 48
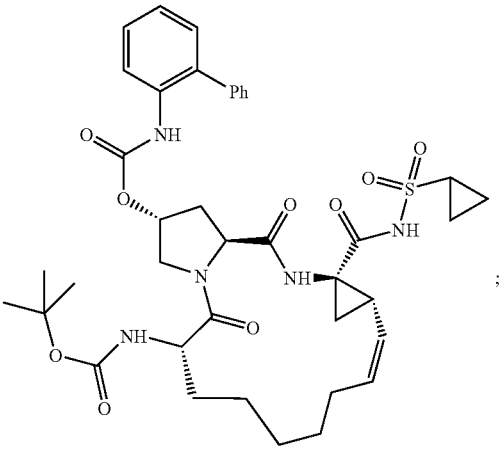

-continued

Compound 49

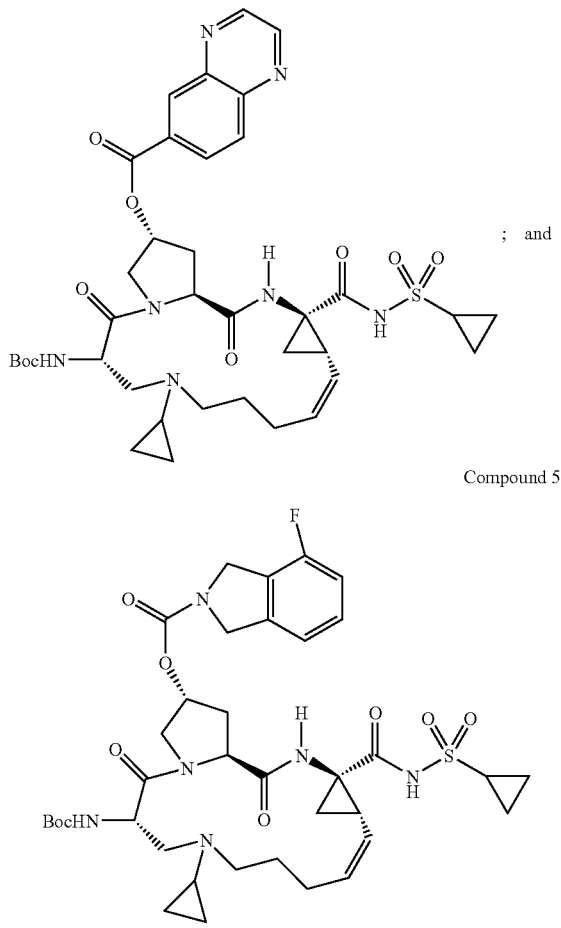

Compound 50

In another embodiment the present disclosure provides a composition comprising a compound of formula (I), or a pharmaceutically acceptable salt thereof, and a pharmaceutically acceptable carrier.

In another embodiment the present disclosure provides a composition comprising a compound of formula (I), or a pharmaceutically acceptable salt thereof, a pharmaceutically acceptable carrier, and at least one of an interferon and ribavirin. In another embodiment the interferon is selected from interferon alpha 2B, pegylated interferon alpha, consensus interferon, interferon alpha 2A, and lymphoblastiod interferon tau.

In another embodiment the present disclosure provides a composition comprising a compound of formula (I), or a pharmaceutically acceptable salt thereof, a pharmaceutically acceptable carrier, and one or two additional compounds having anti-HCV activity. In another embodiment the additional compounds having anti-HCV activity are independently selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In another embodiment the present disclosure provides a composition comprising a compound of formula (I), or a pharmaceutically acceptable salt thereof, a pharmaceutically acceptable carrier, and one or two additional compounds having anti-HCV activity. In another embodiment the additional compounds having anti-HCV activity are effective to inhibit the function of one or more targets independently selected from HCV metalloprotease, HCV serine protease, HCV polymerase, HCV helicase, HCV NS4B protein, HCV entry, HCV assembly, HCV egress, HCV NS5A protein, HCV NS5B protein, and IMPDH for the treatment of an HCV infection.

In another embodiment the present disclosure provides a method of inhibiting the function of HCV serine protease comprising contacting the HCV serine protease with a compound of formula (I), or a pharmaceutically acceptable salt thereof.

In another embodiment the present disclosure provides a method of treating an HCV infection in a patient, comprising administering to the patient a therapeutically effective amount of a compound of formula (I), or a pharmaceutically acceptable salt thereof.

In another embodiment the present disclosure provides a method of treating an HCV infection in a patient, comprising administering to the patient a therapeutically effective amount of a compound of formula (I), or a pharmaceutically acceptable salt thereof, and at least one of an interferon and ribavirin in another embodiment the interferon is selected from interferon alpha 2B, pegylated interferon alpha, consensus interferon, interferon alpha 2A, and lymphoblastiod interferon tau.

In another embodiment the present disclosure provides a method of treating an HCV infection in a patient, comprising administering to the patient a therapeutically effective amount of a compound of formula (I), or a pharmaceutically acceptable salt thereof, and administering one or two additional compounds having anti-HCV activity prior to, after, or simultaneously with the compound of formula (I), or the pharmaceutically acceptable salt thereof.

In another embodiment the present disclosure provides a method of treating an HCV infection in a patient, comprising administering to the patient a therapeutically effective amount of a compound of formula (I), or a pharmaceutically acceptable salt thereof, and administering one or two additional compounds having anti-HCV activity prior to, after, or simultaneously with the compound of formula (I), or the pharmaceutically acceptable salt thereof, wherein the additional compounds having anti-HCV activity are independently selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In another embodiment the present disclosure provides a method of treating an HCV infection in a patient, comprising administering to the patient a therapeutically effective amount of a compound of formula (I), or a pharmaceutically acceptable salt thereof, and administering one or two additional compounds having anti-HCV activity prior to, after, or simultaneously with the compound of formula (I), or the pharmaceutically acceptable salt thereof, wherein the additional compounds having anti-HCV activity are effective to inhibit one or more targets selected from HCV metalloprotease, HCV serine protease, HCV polymerase, HCV helicase, HCV NS4B protein, HCV NS5B protein, HCV entry, HCV assembly, HCV egress, HCV NS5A protein, and IMPDH for the treatment of an HCV infection.

In another aspect the present disclosure provides compounds of formula (I)

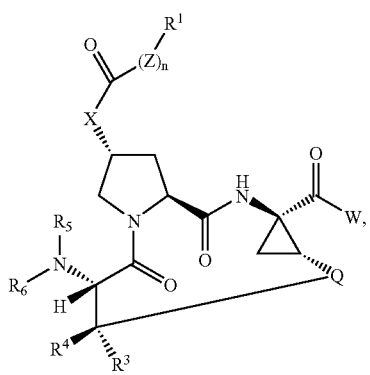

or a pharmaceutically acceptable salt thereof, wherein $R^1$ is selected from hydrogen, alkoxyalkyl, alkyl, aryl, arylalkyl, cyanoalkyl, cycloalkyl, (cycloalkyl)alkyl, dialkylaminoalkyl, haloalkoxyalkyl, haloalkyl, heterocyclyl, heterocylylalkyl, and hydroxyalkyl;

$R^3$ and $R^4$ are independently selected from hydrogen, alkoxyalkyl, alkyl, haloalkoxyalkyl, and haloalkyl;

$R^5$ is selected from hydrogen, alkyl and haloalkyl;

$R^6$ is selected from hydrogen, alkyl, alkoxycarbonyl, alkylaminocarbonyl, alkylcarbonyl, aminocarbonyl, aryloxycarbonyl, cycloalkyloxycarbonyl, dialkylaminocarbonyl, haloalkoxycarbonyl, haloalkyl, and heterocyclylcarbonyl;

Q is a $C_{3-9}$ saturated or unsaturated chain optionally containing from one to three heteroatoms independently selected from O, $S(O)_m$, and $NR^7$; wherein m is 0, 1, or 2, and $R^7$ is selected from hydrogen, alkoxy, alkoxycarbonyl, alkyl, alkylcarbonyl, alkylsulfonyl, aminocarbonyl, arylsulfonyl, cycloalkyl, (cycloalkyl)alkyl, cycloalkoxy, dialkylaminocarbonyl, and haloalkyl;

W is selected from alkoxy, hydroxy, and $-NHSO_2R^8$; wherein $R^8$ is selected from cycloalkyl, optionally substituted with alkyl, alkoxy, halo, haloalkyl, cyano, alkylcyano, or haloalkoxy; alkyl; aryl; (cycloalkyl)alkyl; heterocyclyl; and $-NR^aR^b$; wherein $R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl;

X is selected from O and NH;

n is 0 or 1; and

Z is selected from O and $NR^9$; wherein $R^9$ is selected from hydrogen, alkyl, aryl, arylalkyl, cycloalkyl, (cycloalkyl)alkyl, and heterocyclyl.

In another aspect of the invention, when Q is a $C_6$ chain not containing heteroatoms, more specifically a $C_6$ chain either saturated or unsaturated at the C7-C8 position, then the group;

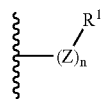

is not a substituted or unsubstituted heterocyclyl of the following formulas:

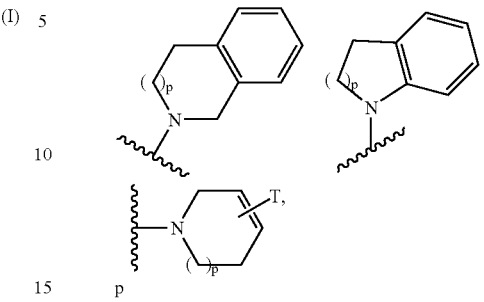

where p is 0 or 1 and T is a fused or appended aryl heteroaryl ring system.

In another aspect of the invention, Q contains at least one heteroatom. In this aspect of the invention, $R^1$ can be, for example, a heterocyclyl. Optionally, n can be 0. The heterocyclyl can be attached to the parent molecular moiety through a heteroatom. Preferably, when Q contains at least one heteroatom and $R^1$ is heterocyclyl, the heterocycyl is attached to the parent molecular moiety through a heteroatom in the heterocyclyl. Preferably, the heteroatom in Q is nitrogen.

In another aspect of the invention, $R^1$ is selected from alkyl, aryl, arylalkyl, cycloalkyl, (cycloalkyl)alkyl, heterocyclyl, and heterocyclylalkyl. Preferably, $R^1$ is selected from aryl, arylalkyl, heterocyclyl, and heterocyclylalkyl.

In another aspect of the invention, $R^1$ is a heterocyclyl containing at least two heteroatoms.

In another aspect of the invention, $R^3$ and $R^4$ are independently selected from hydrogen and alkyl.

In another aspect of the invention, $R^5$ is hydrogen.

In another aspect of the invention, $R^6$ is selected from alkoxycarbonyl, alkylaminocarbonyl, arylcarbonyl alkylcarbonyl, aminocarbonyl, cycloalkyloxycarbonyl, dialkylaminocarbonyl, and heterocyclylcarbonyl. Preferably, $R^6$ is selected from alkoxycarbonyl, cycloalkoxycarbonyl, alkylcarbonyl and alkylaminocarbonyl.

In another aspect of the invention, Q is a $C_{5-6}$ saturated or unsaturated chain optionally containing from one to two heteroatoms independently selected from O and $NR^7$, wherein $R^7$ is selected from hydrogen, alkoxy, alkoxycarbonyl, alkyl, alkylcarbonyl, cycloalkyl, (cycloalkyl)alkyl, cycloalkoxy, dialkylaminocarbonyl, and haloalkyl. Preferably, Q is a $C_6$ saturated or unsaturated chain optionally containing one heteroatom selected from O and $NR^7$, wherein $R^7$ is selected from hydrogen, alkoxy, alkoxycarbonyl, alkyl, cycloalkyl, dialkylaminocarbonyl, and haloalkyl.

In another aspect of the invention, W is $-NHSO_2R^8$; wherein $R^8$ is selected from cycloalkyl optionally substituted with alkyl, alkoxy, halo, haloalkyl, or cyano; alkyl; aryl; (cycloalkyl)alkyl; heterocyclyl; and $-NR^aR^b$; wherein $R^a$ and $R^b$ are independently selected from hydrogen, alkoxy, alkyl, cycloalkyl, and (cycloalkyl)alkyl.

In another aspect of the invention, $R^8$ is selected from cycloalkyl optionally substituted with alkyl and alkoxy; heterocyclyl; and $-NR^aR^b$; wherein $R^a$ and $R^b$ are independently selected from hydrogen, and alkyl.

In another aspect of the invention, Z is $NR^9$; wherein $R^9$ is selected from hydrogen, alkyl, aryl, arylalkyl, cycloalkyl, (cycloalkyl)alkyl, and heterocyclyl. Preferably, $R^9$ is hydrogen.

In another aspect of the invention, R¹ is selected from aryl and heterocyclyl, wherein the heterocyclyl is attached to the carbonyl group adjacent to R¹ through a carbon atom of the heterocyclyl ring.

In another aspect of the invention, there are provided compounds of formula (II)

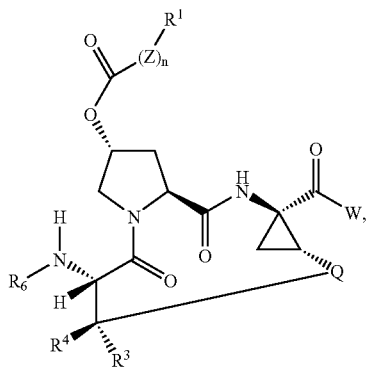

(II)

or a pharmaceutically acceptable salt thereof, wherein $R^1$ is selected from alkyl, aryl, arylalkyl, cycloalkyl, (cycloalkyl)alkyl, heterocyclyl, and heterocyclylalkyl;

$R^3$ and $R^4$ are independently selected from hydrogen and alkyl, $R^6$ is selected from alkoxycarbonyl, alkylaminocarbonyl, arylcarbonyl alkylcarbonyl, aminocarbonyl, cycloalkyloxycarbonyl, dialkylaminocarbonyl, and heterocyclylcarbonyl;

Q is a $C_{5-6}$ saturated or unsaturated chain optionally containing from one to two heteroatoms independently selected from O and $NR^7$, wherein $R^7$ is selected from hydrogen, alkoxy, alkoxycarbonyl, alkyl, alkylcarbonyl, cycloalkyl, (cycloalkyl)alkyl, cycloalkoxy, dialkylaminocarbonyl, and haloalkyl;

W is $-NHSO_2R^8$; wherein $R^8$ is selected from cycloalkyl optionally substituted with alkyl, alkoxy, halo, haloalkyl or cyano; alkyl; aryl; (cycloalkyl)alkyl; heterocyclyl; and $-NR^aR^b$; wherein $R^a$ and $R^b$ are independently selected from hydrogen, alkoxy, alkyl, cycloalkyl, and (cycloalkyl)alkyl;

n is 0 or 1; and

Z is $NR^9$; wherein $R^9$ is selected from hydrogen, alkyl, aryl, arylalkyl, cycloalkyl, (cycloalkyl)alkyl, and heterocyclyl.

In another aspect of the invention, there are provided compounds of formula (III)

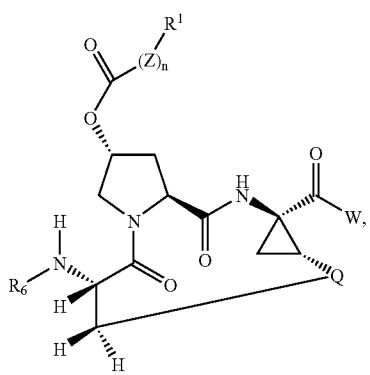

(III)

or a pharmaceutically acceptable salt thereof, wherein $R^1$ is selected from aryl, arylalkyl, heterocyclyl, and heterocyclylalkyl;

$R^6$ is selected from alkoxycarbonyl, cycloalkoxycarbonyl, alkylcarbonyl and alkylaminocarbonyl;

Q is a $C_6$ saturated or unsaturated chain optionally containing one heteroatom selected from O, and $NR^7$, wherein $R^7$ is selected from hydrogen, alkoxy, alkoxycarbonyl, alkyl, cycloalkyl, dialkylaminocarbonyl, and haloalkyl;

W is $-NHSO_2R^8$; wherein $R^8$ is selected from cycloalkyl optionally substituted with alkyl or alkoxy; heterocyclyl; and $-NR^aR^b$; wherein $R^a$ and $R^b$ are independently selected from hydrogen, and alkyl;

n is 0 or 1; and

Z is $NR^9$; wherein $R^9$ is selected from hydrogen and aryl.

In another aspect of the invention, there are provided compounds of formula (IV)

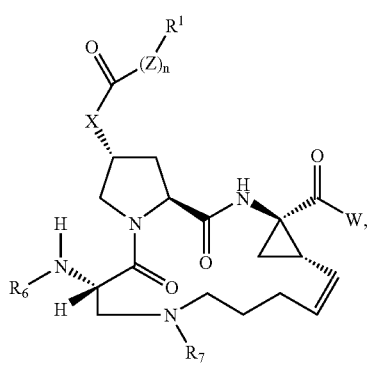

(IV)

or a pharmaceutically acceptable salt thereof, wherein $R^1$ is selected from alkyl, aryl, arylalkyl, cycloalkyl, (cycloalkyl)alkyl, heterocyclyl, and heterocyclylalkyl;

$R^6$ is selected from alkoxycarbonyl, cycloalkoxycarbonyl, alkylaminocarbonyl, arylcarbonyl, alkylcarbonyl, and dialkylaminocarbonyl;

$R^7$ is selected from hydrogen, alkoxy, alkoxycarbonyl, alkyl, alkylcarbonyl, aminocarbonyl, cycloalkyl, dialkylaminocarbonyl, and haloalkyl;

W is selected from alkoxy, hydroxy, and $-NHSO_2R^8$; wherein $R^8$ is selected from cycloalkyl optionally substituted with alkyl, alkoxy, halo, haloalkyl, arylalkyl, alkene, alkyne, cycloalkyl, dialkylaminocarbonyl, alkylaminocarbonyl, cycloalkyl(alkyl); aryl; heterocyclyl; and $-NR^aR^b$; wherein $R^a$ and $R^b$ are independently selected from hydrogen, alkoxy, alkyl, aryl, arylalkyl, cycloalkyl, heterocyclylalkyl, and haloalkyl;

X is O or NH;

n is 0 or 1; and

Z is $NR^9$; wherein $R^9$ is selected from hydrogen, alkyl, aryl, arylalkyl, cycloalkyl, (cycloalkyl)alkyl, and heterocyclyl.

In another aspect of the invention, there are provided compounds of formula (V)

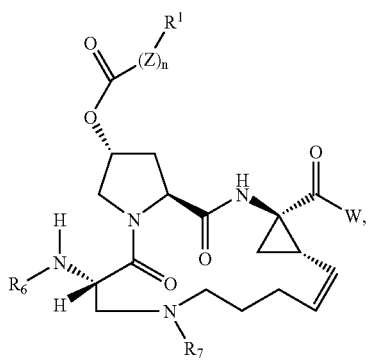

(V)

or a pharmaceutically acceptable salt thereof, wherein
$R^1$ is selected from aryl and heterocyclyl;
$R^6$ is selected from alkoxycarbonyl, cycloalkoxycarbonyl, alkylaminocarbonyl, and alkylcarbonyl;
$R^7$ is selected from hydrogen, alkoxy, alkoxycarbonyl, alkyl, cycloalkyl, and dialkylaminocarbonyl;
W is —$NHSO_2R^8$; wherein $R^8$ is selected from cycloalkyl optionally substituted with alkyl and alkoxy; heterocyclyl; and —$NR^aR^b$; wherein $R^a$ and $R^b$ are independently selected from hydrogen, and alkyl;
n is 0 or 1; and
Z is $NR^9$; wherein $R^9$ is selected from hydrogen and aryl.

In another aspect of the invention, there are provided compounds of formula (VI)

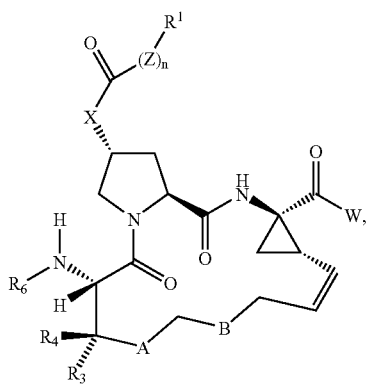

(VI)

or a pharmaceutically acceptable salt thereof, wherein
$R^1$ is selected from hydrogen, alkoxyalkyl, alkyl, aryl, arylalkyl, cyanoalkyl, cycloalkyl, (cycloalkyl)alkyl, dialkylaminoalkyl, haloalkoxyalkyl, haloalkyl, heterocyclyl, heterocyclylalkyl, and hydroxyalkyl;
$R^3$ and $R^4$ are independently selected from hydrogen, alkoxyalkyl, alkyl, haloalkoxyalkyl, and haloalkyl;
A and B are independently selected from $CH_2$, and O; provided that both A and B cannot be O;
$R^6$ is selected from hydrogen, alkyl, alkoxycarbonyl, cycloalkylamino alkylaminocarbonyl, arylcarbonyl, alkylcarbonyl, aminocarbonyl, aryloxycarbonyl, cycloalkyloxycarbonyl, dialkylaminocarbonyl, haloalkoxycarbonyl, haloalkyl, and heterocyclylcarbonyl;

W is selected from alkoxy, hydroxy, and —$NHSO_2R^8$; wherein $R^8$ is selected from cycloalkyl optionally substituted with alkyl, alkoxy, halo, haloalkyl, cyano, cyanoalkyl, arylalkyl, alkene, alkyne, cycloalkyl, dialkylaminocarbonyl, alkylaminocarbonyl, arylaminocarbonyl, arylcarbonyl, cycloalkyl(alkyl), or heteroarylalkyl; alkyl; aryl; cycloalkyl; (cycloalkyl)alkyl; heterocyclyl; and —$NR^aR^b$; wherein $R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl;
X is selected from O and NH;
n is 0 or 1; and
Z is selected from O and $NR^9$; wherein $R^9$ is selected from hydrogen, alkyl, aryl, arylalkyl, cycloalkyl, (cycloalkyl)alkyl, and heterocyclyl: provided that when A and B are both $CH_2$, the group;

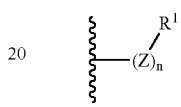

is not a substituted or unsubstituted heterocyclyl of the following formulas:

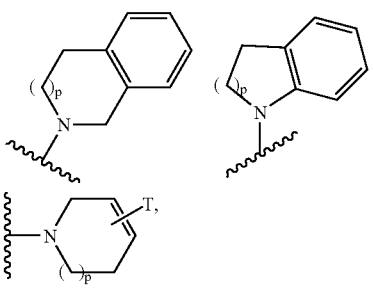

where p is 0 or 1 and T is a fused or appended aryl heteroaryl ring system.

In another aspect of the invention, there are provided compounds of formula (VII)

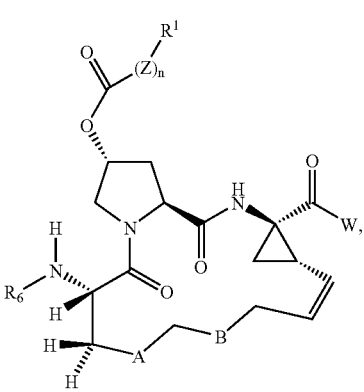

(VII)

or a pharmaceutically acceptable salt thereof, wherein
$R^1$ is selected from aryl and heterocyclyl;
A and B are independently selected from $CH_2$, and O; provided that both A and B cannot be O;

R[6] is selected from alkoxycarbonyl, cycloalkoxycarbonyl, alkylaminocarbonyl, and alkylcarbonyl;

W is —NHSO$_2$R[8]; wherein R[8] is selected from cycloalkyl optionally substituted with alkyl and alkoxy; heterocyclyl; and —NR$^a$R$^b$; wherein R$^a$ and R$^b$ are independently selected from hydrogen, and alkyl;

n is 0 or 1; and

Z is NR[9]; wherein R[9] is selected from hydrogen and aryl: provided that when A and B are both CH$_2$, the group;

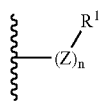

is not a substituted or unsubstituted heterocyclyl of the following formulas:

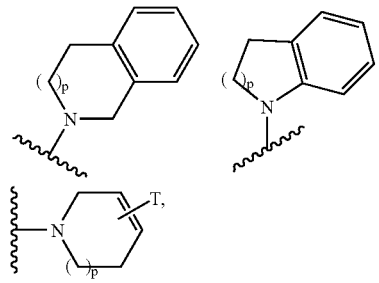

where p is 0 or 1 and T is a fused or appended aryl heteroaryl ring system.

In another aspect of the invention, there are provided compounds of formula (VIII)

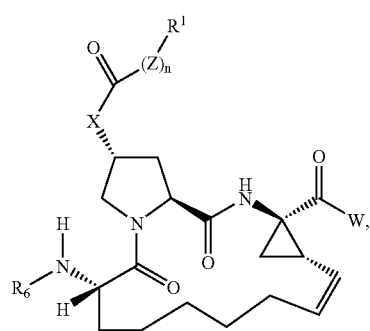

(VIII)

or a pharmaceutically acceptable salt thereof, wherein

R[1] is selected from hydrogen, alkoxyalkyl, alkyl, aryl, arylalkyl, cyanoalkyl, cycloalkyl, (cycloalkyl)alkyl, dialkylaminoalkyl, haloalkoxyalkyl, haloalkyl, heterocyclyl, heterocyclylalkyl, and hydroxyalkyl;

R[6] is selected from hydrogen, alkyl, alkoxycarbonyl, alkylaminocarbonyl, alkylcarbonyl, aminocarbonyl, aryloxycarbonyl, cycloalkyloxycarbonyl, dialkylaminocarbonyl, haloalkoxycarbonyl, haloalkyl, and heterocyclylcarbonyl;

W is selected from alkoxy, hydroxy, and —NHSO$_2$R[8]; wherein R[8] is selected from cycloalkyl, optionally substituted with alkyl, alkoxy, halo, haloalkyl, cyano, alkylcyano, or haloalkoxy; alkyl; aryl; (cycloalkyl)alkyl; heterocyclyl; and —NR$^a$R$^b$; wherein R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl;

X is selected from O and NH;

n is 0 or 1; and

Z is selected from O and NR[9]; wherein R[9] is selected from hydrogen, alkyl, aryl, arylalkyl, cycloalkyl, (cycloalkyl)alkyl, and heterocyclyl: provided that the group;

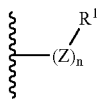

is not a substituted or unsubstituted heterocyclyl of the following formulas:

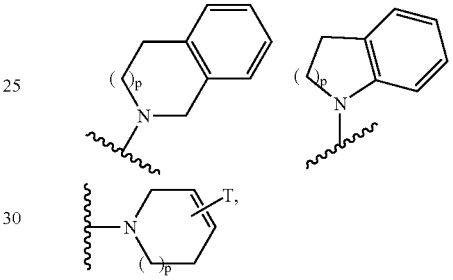

where p is 0 or 1 and T is a fused or appended aryl heteroaryl ring system.

In another aspect of the invention, there are provided compounds of formula (IX)

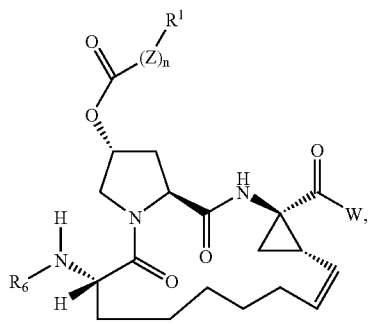

(IX)

or a pharmaceutically acceptable salt thereof, wherein

R[1] is selected from aryl and heterocyclyl;

R[6] is selected from alkoxycarbonyl, cycloalkoxycarbonyl, alkylaminocarbonyl, and alkylcarbonyl;

W is —NHSO$_2$R[8]; wherein R[8] is selected from cycloalkyl optionally substituted with alkyl and alkoxy; heterocyclyl; and —NR$^a$R$^b$; wherein R$^a$ and R$^b$ are independently selected from hydrogen and alkyl;

n is 0 or 1; and

Z is NR[9]; wherein R[9] is selected from hydrogen and aryl: provided that the group;

is not a substituted or unsubstituted heterocyclyl of the following formulas:

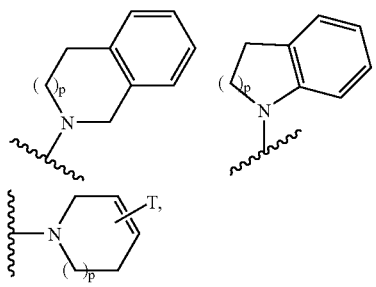

where p is 0 or 1 and T is a fused or appended aryl heteroaryl ring system.

Unless otherwise specifically noted herein, the terms set forth below will have the following definitions.

It should be understood that the compounds encompassed by the present disclosure are those with chemical stability suitable for administration as pharmaceutical agents.

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylaminocarbonyl," as used herein, refers to —C(O)NR$^x$R$^y$; wherein one of R$^x$ and R$^y$ is hydrogen and the other is an alkyl group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "aminocarbonyl," as used herein, refers to —C(O)NH$_2$.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkenyl, alkoxy, alkoxycarbonyl, alkyl, a second aryl group, arylalkyl, aryloxy, cyano, cyanoalkyl, halo, haloalkoxy, haloalkyl, heterocyclyl, heterocyclylalkyl, nitro, and oxo; wherein the second aryl group, the aryl part of the arylalkyl and the aryloxy, the heterocyclyl, and the heterocyclyl part of the heterocyclylalkyl can be further optionally substituted with one, two, three, four, or five substituents independently selected from alkenyl, alkoxy, alkyl, cyano, halo, haloalkoxy, haloalkyl, nitro, and oxo.

The term "arylalkyl," as used herein, refers to an alkyl group substituted with one, two, or three aryl groups.

The term "aryloxy," as used herein, refers to an aryl group attached to the parent molecular moiety through an oxygen atom.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The term "carbonyl," as used herein, refers to —C(O)—.

The term "cyano," as used herein, refers to —CN.

The term "cyanoalkyl," as used herein, refers to an alkyl group substituted with one, two, or three cyano groups.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl. The cycloalkyl groups of the present disclosure can be optionally substituted with one, two, three, or four substituents independently selected from alkenyl, alkoxy, alkyl, halo, haloalkoxy, and haloalkyl.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkyloxycarbonyl," as used herein, refers to a cycloalkyloxy group attached to the parent molecular moiety through a carbonyl group.

The term "dialkylamino," as used herein, refers to —NR$^x$R$^y$, wherein R$^x$ and R$^y$ are the same or different alkyl groups.

The term "dialkylaminoalkyl," as used herein, refers to an alkyl group substituted by one, two, or three dialkylamino groups.

The term "dialkylaminocarbonyl," as used herein, refers to —C(O)NR$^x$R$^y$, wherein R$^x$ and R$^y$ are the same or different alkyl groups. Optionally, R$^x$ and R$^y$ can combine to form a ring.

The term "dialkylaminocarbonylalkyl," as used herein, refers to an alkyl group substituted with one, two, or three —C(O)NR$^x$R$^y$ groups.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxyalkyl," as used herein, refers to an alkyl group substituted by one, two, or three haloalkoxy groups.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four to seven-membered, preferably four- to six-membered, aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure can be optionally substituted with one, two, three, four, or five substituents independently selected from alkenyl, alkoxy, alkyl, aryl, arylalkyl, aryloxy, cyano, cyanoalkyl, halo, haloalkoxy, haloalkyl, a second heterocyclyl group, heterocyclylalkyl, nitro, and oxo; wherein the aryl, the aryl part of the arylalkyl and the aryloxy, the second heterocyclyl, and the heterocyclyl part of the heterocyclylalkyl can be further optionally substituted with one, two, three, four, or five substituents independently selected from alkenyl, alkoxy, alkyl, cyano, halo, haloalkoxy, haloalkyl, nitro, and oxo.

The term "heterocyclylalkyl," as used herein, refers to an alkyl group substituted with one, two, or three heterocyclyl groups.

The term "heterocyclylcarbonyl," as used herein, refers to a heterocyclyl group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "—NR$^a$R$^b$," as used herein, refers to two groups, R$^a$ and R$^b$, which are attached to the parent molecular moiety through a nitrogen atom. R$^a$ and R$^b$ are independently selected from alkyl, aryl, arylalkyl, cycloalkyl, (cycloalkyl)alkyl, heterocyclyl, and heterocyclylalkyl.

The term "nitro," as used herein, refers to —NO$_2$.

The term "oxo," as used herein, refers to =O.

The term "sulfonyl," as used herein, refers to —SO$_2$—.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

The term "compounds of the disclosure", and equivalent expressions, are meant to embrace compounds of formula (I), and pharmaceutically acceptable enantiomers, diastereomers, salts, and solvates, e.g. hydrates, thereof. Similarly, references to intermediates, are meant to embrace their salts, and solvates, where the context so permits.

As used herein, the term "small molecule compound" means a compound having a molecular weight of less than 1,500 daltons, preferably less than 1000 daltons.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

In referencing the compounds of the present disclosure, the numbering of positions on the compounds is as shown below:

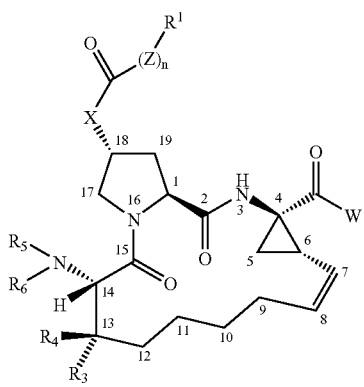

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I, Transactions of the Royal Society London series (1970), B257, 249-264].

The following figure shows the subsite designations for the compounds of the present disclosure.

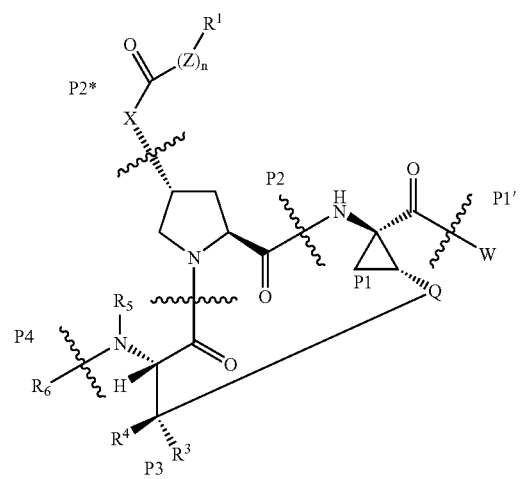

Asymmetric centers exist in the compounds of the present disclosure. For example, the compounds may include P1 cyclopropyl element of formula

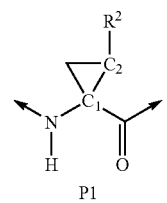

wherein $C_1$ and $C_2$ each represent an asymmetric carbon atom at positions 1 and 2 of the cyclopropyl ring. Not withstanding other possible asymmetric centers at other segments of the compounds, the presence of these two asymmetric centers means that the compounds can exist as racemic mixtures of diastereomers, such as the diastereomers wherein $R^2$ is configured either syn to the amide or syn to the carbonyl as shown below.

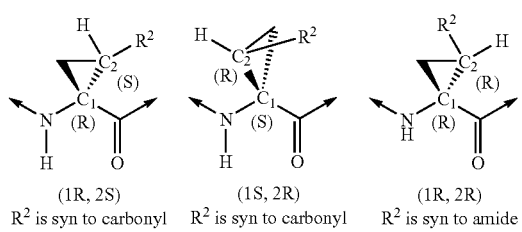

-continued

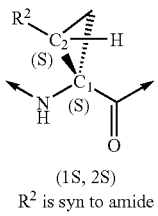

(1S, 2S)
R² is syn to amide

It should be understood that the disclosure encompasses all stereochemical isomeric forms, or mixtures thereof, which possess the ability to inhibit HCV protease. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like.

Tablets are formulated, for example, by preparing a powder mixture, granulating or slugging, adding a lubricant and disintegrant, and pressing into tablets. A powder mixture is prepared by mixing the compound, suitable commminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

In another aspect of the invention, there is provided a pharmaceutical composition comprising a compound of the invention and a pharmaceutically acceptable carrier, further comprising at least one of an interferon and ribavirin.

In another aspect of the invention, there is provided a composition comprising a compound of the invention and a pharmaceutically acceptable carrier, further comprising a second compound having anti-HCV activity. In another aspect of the invention, the second compound having anti- HCV activity is an interferon. Preferably, the interferon is selected from interferon alpha 2B, pegylated interferon alpha, consensus interferon, interferon alpha 2A, and lymphoblastiod interferon tau. In another aspect of the invention, the second compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine. In another aspect of the invention, the second compound having anti-HCV activity is a small molecule compound. Preferably, the second compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In another aspect of the invention, there are provided methods of inhibiting the function of HCV serine protease comprising contacting the HCV serine protease with a compound of the invention.

In another aspect of the invention, there are provided methods of treating an HCV infection in a patient, comprising administering to the patient a therapeutically effective amount of a compound of the invention. Preferably, the compound is effective to inhibit the function of the HCV serine protease. An aspect of the invention further comprises administering a second compound having anti-HCV activity prior to, after, or simultaneously with a compound of the invention.

Certain illustrative HCV inhibitor compounds which can be administered with the compounds of the present disclosure include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Type of Inhibitor or Target | Source Company |
| --- | --- | --- |
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |

TABLE 1-continued

| Brand Name | Type of Inhibitor or Target | Source Company |
|---|---|---|
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| SCH-503034 | serine protease inhibitor | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The starting materials useful to synthesize the compounds of the present disclosure are known to those skilled in the art and can be readily manufactured or are commercially available.

The compounds of the present invention can be manufactured by methods known to those skilled in the art. The following methods set forth below are provided for illustrative purposes and are not intended to limit the scope of the claimed invention. For example, compounds of the present invention having the structure of Formula I can be synthesized, as shown in scheme 1. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

As shown in scheme 1, intermediates of the present invention such as dipeptide 1, can be used for the preparation of compounds of Formula 1. In the first step of this process the Boc protected nitrogen of 1 is deprotected using an acid such as HCl in a solvent such as ether, to provide the corresponding free amine 2. Amine 2 can be subsequently coupled to amino acid 3 using a coupling agent such as HATU in a solvent such as dichloromethane to provide the tripeptide intermediate 4. It should be noted that in some cases intermediates like 3 are commercially available, and alternatively such compounds can be readily prepared in racemic or chiral fashion by methods known in the art. A key transformation in the construction of compounds of Formula 1 is the macrocyclization process wherein intermediates of general structure 4 are converted into intermediates of general structure 5. In the general example cited, the conversion of intermediate 4 into 5 can be affected by an intramolecular olefin metathesis reaction. This class of reactions is well established in the art and as such, a number of olefin-metathesis-catalysts have been developed and are commercially available. For example the conversion of diene 4 to macrocycle 5 could be affected by the treatment of 4 with a sufficient quantity of Grubb's first-generation olefin metathesis catalyst, in a solvent such as dichloromethane or dichloroethane. In some examples for the conversion of 4 to 5, it may be necessary to heat the reaction mixture in order to effect this cyclization process. Intermediate 5 is then coverted to compounds of Formula 1 such as 7 by a two step process. In the first step of this process, the ester functionality of intermediate 5 is hydrolyzed to the corresponding carboxylic 6. This transformation can be accomplished by a saponification reaction wherein 5 is treated with a base such as lithium hydroxide in a mixture of THF, methanol and water. The resulting acid 6 can be converted to a compound of Formula 1 by a simple coupling reaction with a sulfonamide derivative as shown. For example, it is well established in the art that treatment of a carboxylic acid like 6, with CDI in a solvent such as methylene chloride, generates in situ a reactive intermediate which when treated with a sulfonamide provides for 7, a compound of Formula 1.

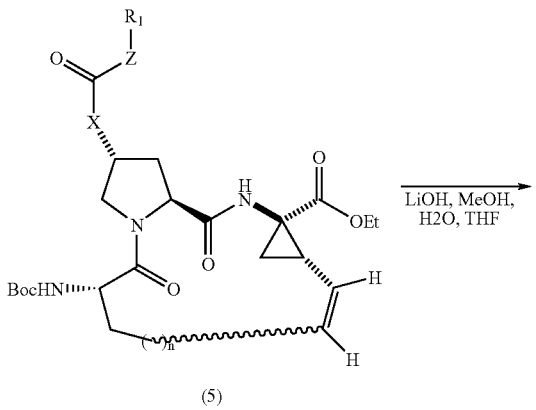

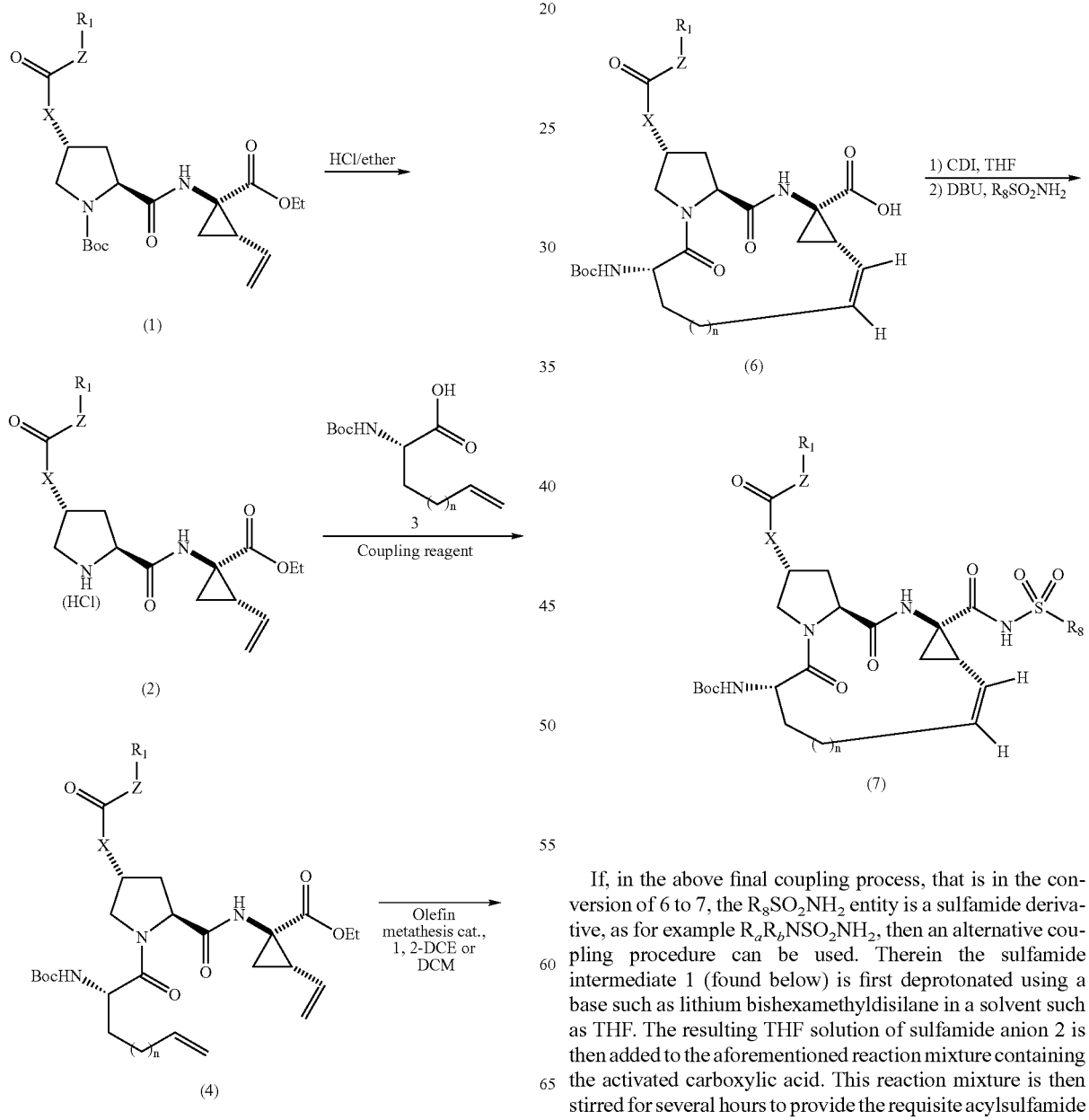

If, in the above final coupling process, that is in the conversion of 6 to 7, the $R_8SO_2NH_2$ entity is a sulfamide derivative, as for example $R_aR_bNSO_2NH_2$, then an alternative coupling procedure can be used. Therein the sulfamide intermediate 1 (found below) is first deprotonated using a base such as lithium bishexamethyldisilane in a solvent such as THF. The resulting THF solution of sulfamide anion 2 is then added to the aforementioned reaction mixture containing the activated carboxylic acid. This reaction mixture is then stirred for several hours to provide the requisite acylsulfamide 7.

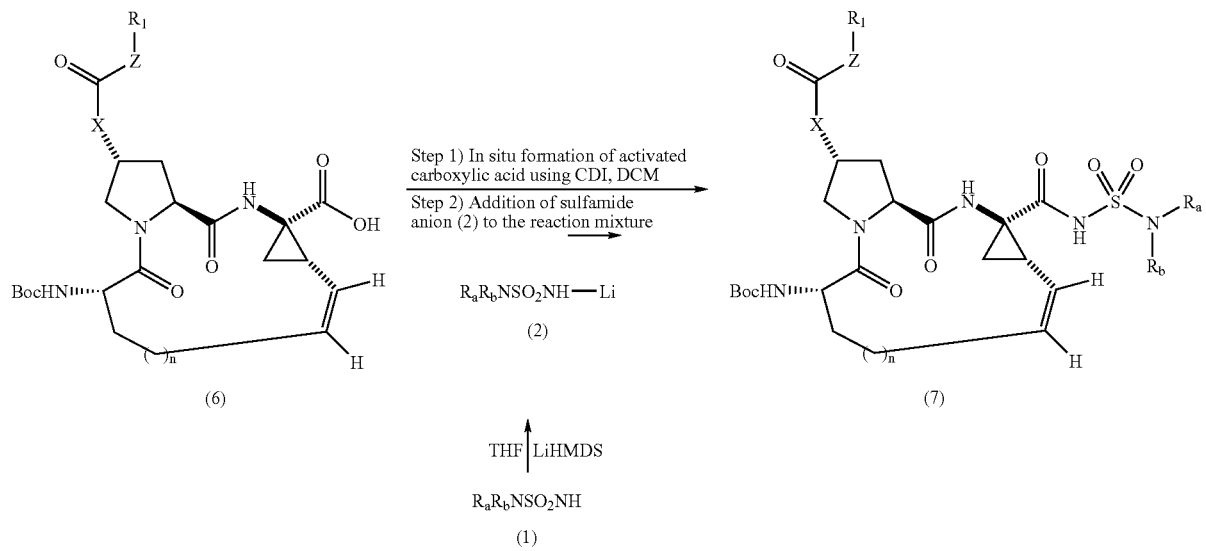

An additional process wherein compounds of Formula I can be prepared is outlined below (Scheme 2). Therein, the P2* functionality, defined herein as the functional group attached to the proline C4-moiety X, is incorporated after the P1-P3 macrocyclization step. However, it should be noted that the process of incorporating of P2* into the molecule can be executed at any suitable stage of the synthesis. In the present, nonlimiting scheme, (Scheme 2) the proline substituent X is protected using a suitable protecting group. This group is then carried through several steps in the synthesis as shown, and removed after the cyclization process to provide an intermediate like 5, which is then converted into a compound of Formula I (6).

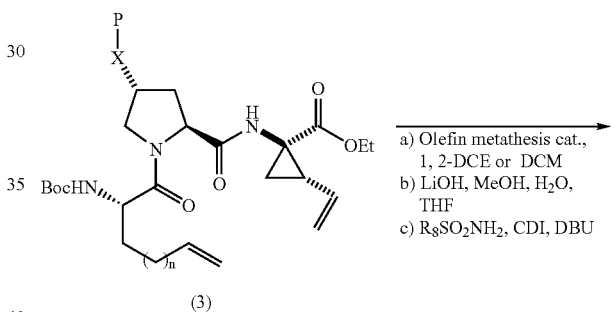

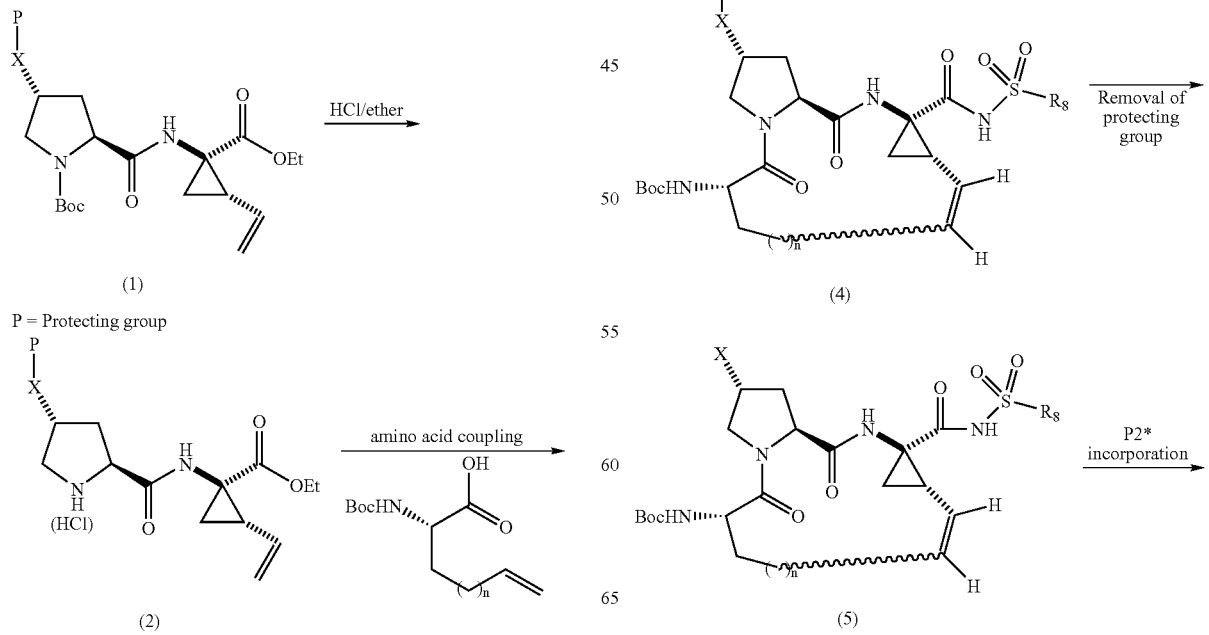

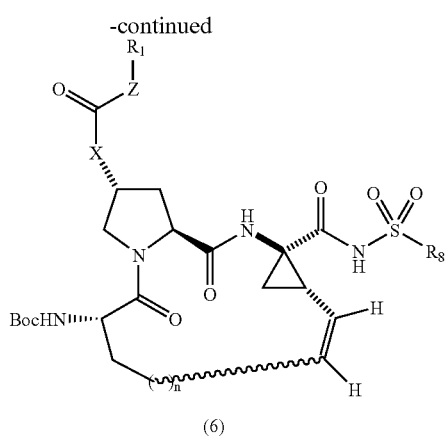

(6)

The conversion of compounds like 5 to compounds like 6, requires the incorporation of P2*. This coupling process can be achieved by a number of established methods known to one skilled in the art the specifics of which depend on the nature of the X group. For example, as shown in scheme 3, if X is an alcohol as in 5a then P2* can be tethered to this functionality by simple acylation reactions. Such reactions could employ acid chlorides or isocyanates or alkylchloroformates to provide esters 6a or carbamates 6b or carbonates 6c respectively.

Scheme 3

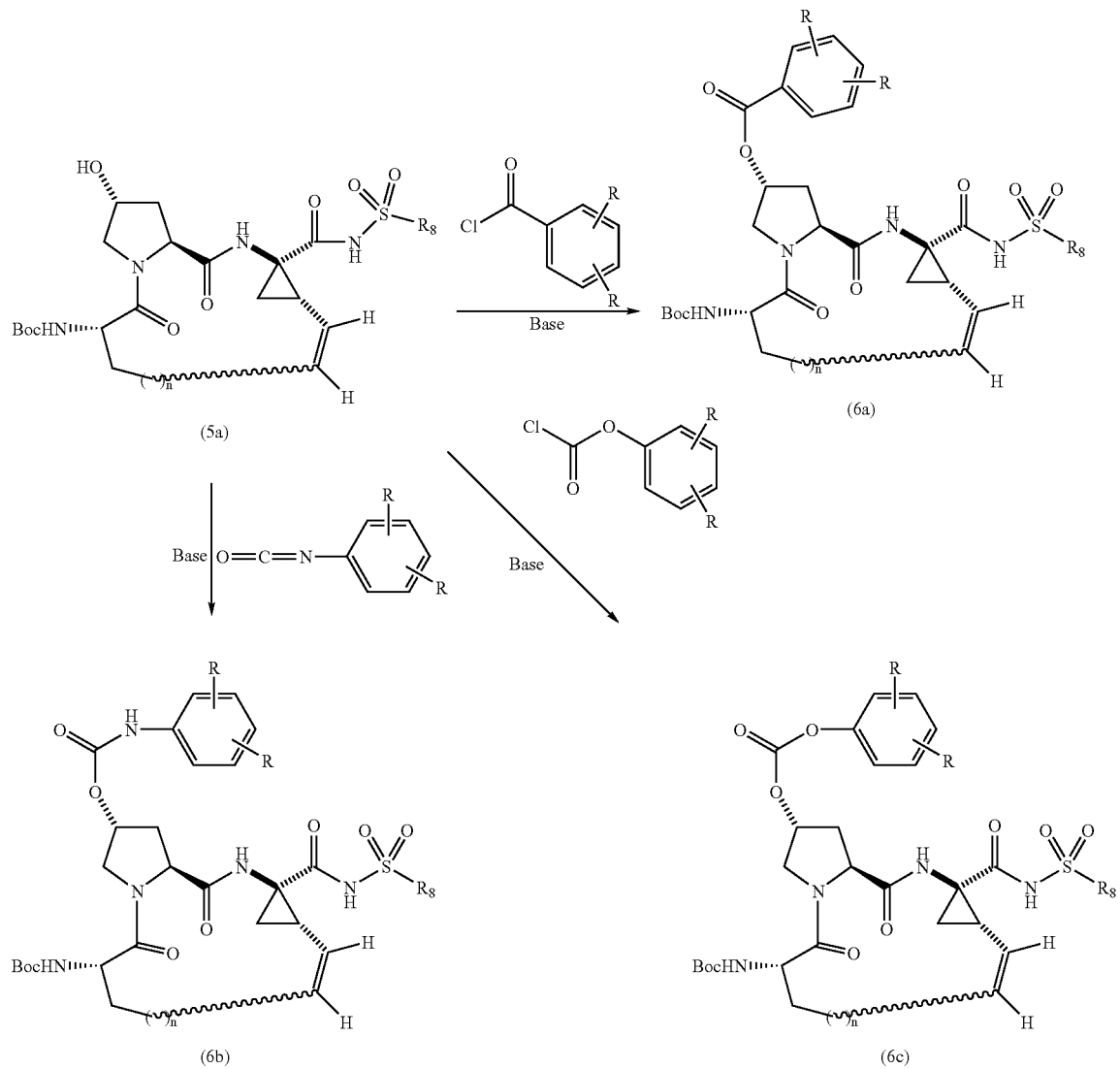

Alternatively, if X is an amine group as in 5b of Scheme 4, then the process for the construction of P2* can be achieved by a number of established methods for the acylation of amines. For example, intermediates like 5b can be converted to amides 7a, ureas 7b, and carbamates 7c of Formula 1 via a simple acylation step as shown.

As an alternative to the above coupling reactions, compounds of Formula 1 can be prepared by the process shown below (Scheme 5), wherein the peptide derivative functions as the acylating agent. For example, an activated carbonate derivative 5c upon treatment with an amine should provide the corresponding carbamate. Such reactions can be con-

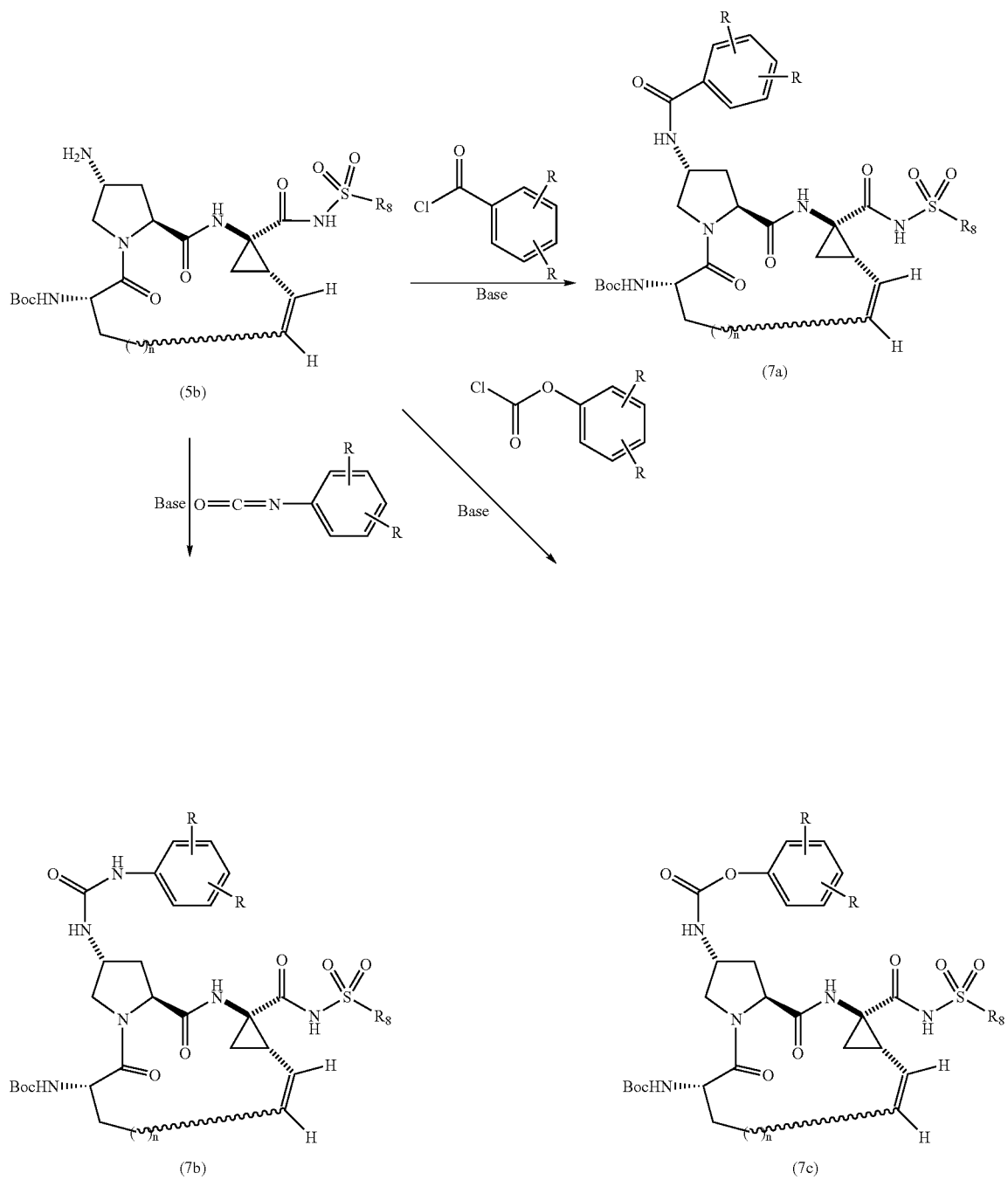

ducted in the presence of a mild base and in a solvent such as dicholoromethane. It may be necessary to heat such a reaction and in such cases a solvent such as dichloroethane or THF or toluene can be used and the reaction heated to reflux.

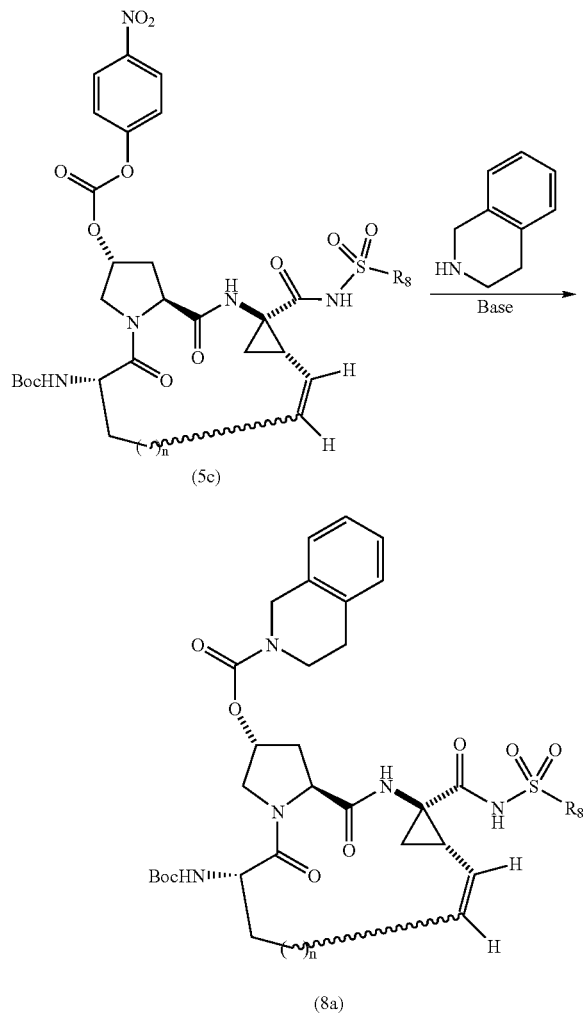

One skilled in the art would recognize that the incorporation of P2* into the molecule can be carried out at any stage in the assembly of the peptide backbone. This is illustrated below for the conversion of intermediates like 1 and 3 into compounds of Formula 1.

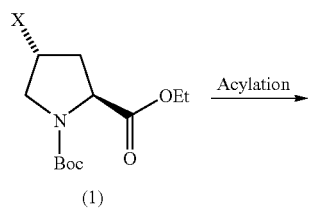

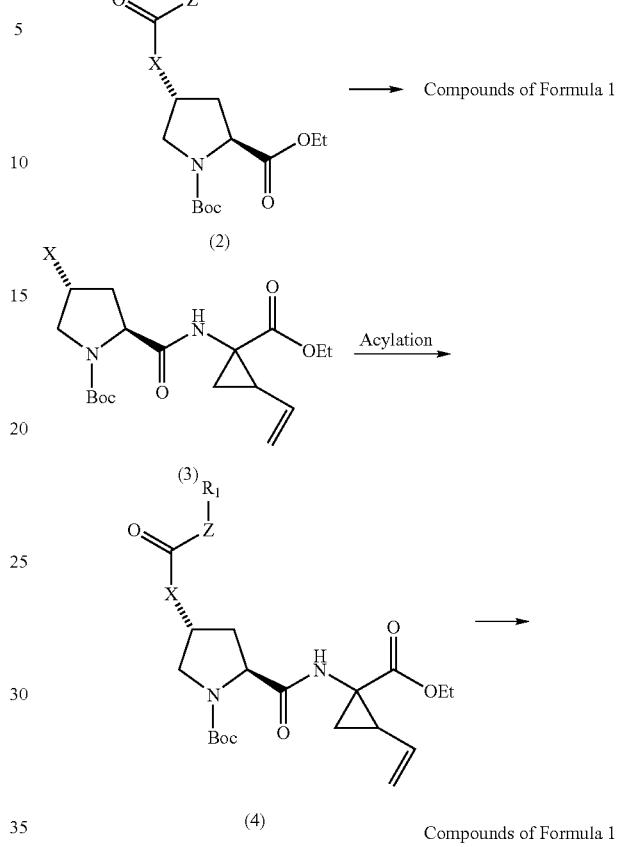

In the construction of compounds of Formula I, the P1' terminus is incorporated into the molecules using one of the general processes outlined above and described in more detail below. In some examples the P1' elements, that is the cycloalkylsulfonamides, alkyl sulfonamides, heteroarylsulfonamides or sulfamides are commercially available or can be prepared from the corresponding alkyl- or cycloalkyl-sulfonyl chloride by treating said sulfonyl chloride with ammonia. Alternatively, these sulfonamides can be synthesized using the general process outlined in Scheme 6. Therein commercially available 3-chloropropylsulfonyl chloride (1) is converted to a suitable protected sulfonamide as for example by treatment with tert-butyl amine. The sulfonamide 2 obtained is then converted to the corresponding cycloalkylsulfonamide 3 by treatment with two equivalents of a base such as butyl lithium in a solvent such as THF at low temperature. The resulting cycloalkylsulfonamide can be deprotected by treatment with an acid to provide the desired unprotected cycloalkylsulfonamide 4. Said P1' fragment 4 can be incorporated into compounds of Formula I. Additionally, the cycloalkyl ring of intermediates like 4 can be further functionalized. For example, treatment of intermediate 3 with a base such as butyl lithium followed by the addition of an electrophile such as an alkyl halide should provide intermediates like 5, wherein the C1 position of the cycloalkyl ring is functionalized. Reactions of this type can be conducted in solvents such as THF. In such a reaction it may be necessary to add two or more equivalents of base to intermediate 3. Moreover, the temperature of such a reaction will likely need to be carefully monitored wherein the THF solution of 3 is cooled to −78 C. prior to the addition of base and this is described in detail herein.

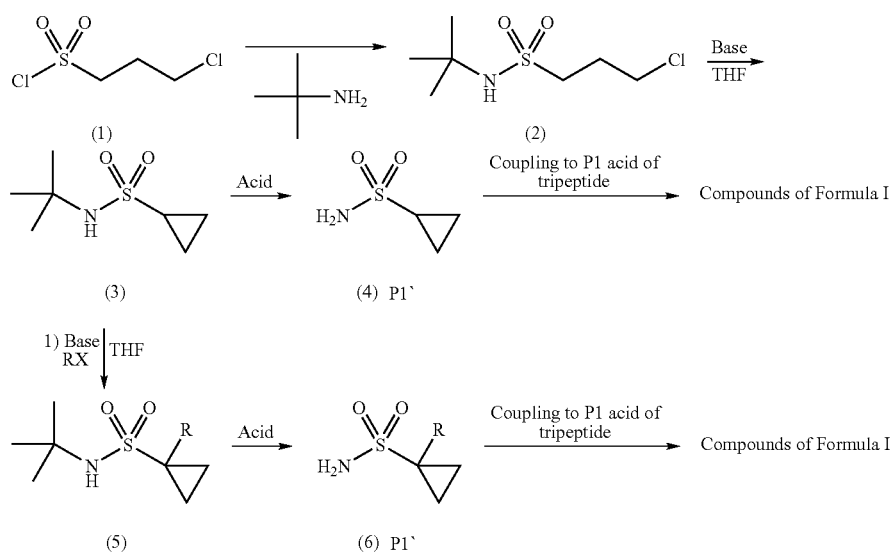

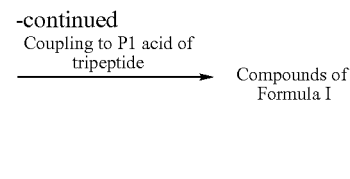

As an alternative to the t-butyl protecting group used in the above scheme (eg. intermediate 2 of scheme 6) a Boc group can be employed as shown below (Scheme 7). Said Boc group can be incorporated by treatment of an intermediate like 2 with Boc anhydride in the presence of a base such as triethylamine in conjunction with catalytic DMAP. The acylsulfonamide 3 obtained is then converted to the corresponding cycloalkylacylsulfonamide 4 by treatment with two equivalents of a base such as butyl lithium in a solvent such as THF at low temperature. The resulting cycloalkylacylsulfonamide 4 can be deprotected by treatment with an acid to provide the desired unprotected cycloalkylsulfoamide. Said P1' fragment can be incorporated into compounds of Formula I.

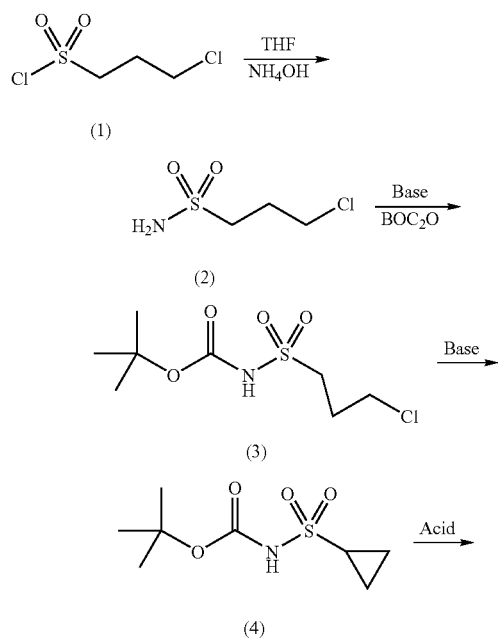

In the preparation of compounds of Formula 1, dipeptide intermediates like 2 shown below can be prepared by the coupling of hydroxyproline derivative 1 with cyclopropyl amino acid B as shown. This coupling reaction can be carried out using reagents such as HATU or HBTU and in solvents such as methylene chloride or DMF or THF.

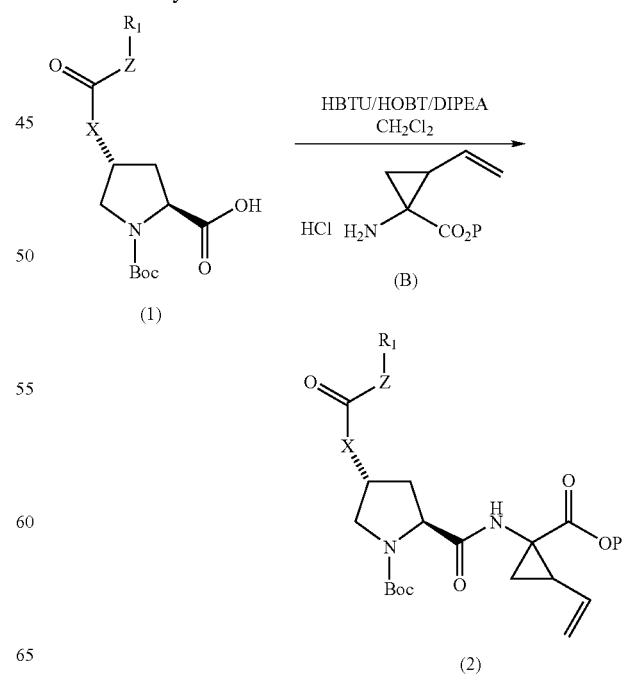

Intermediate B can be synthesized as shown in scheme 8.

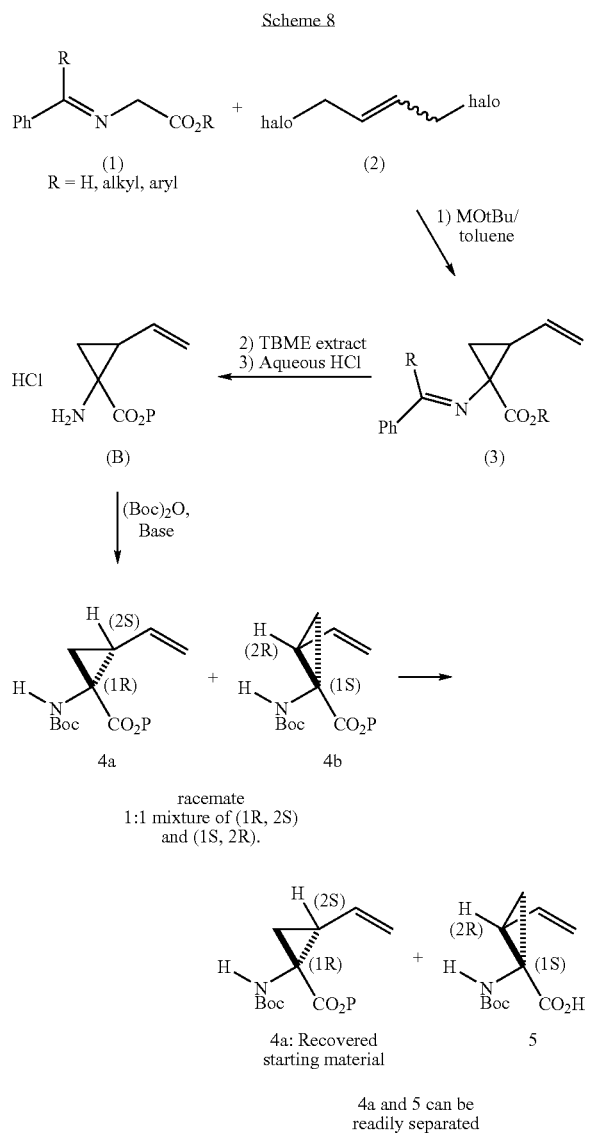

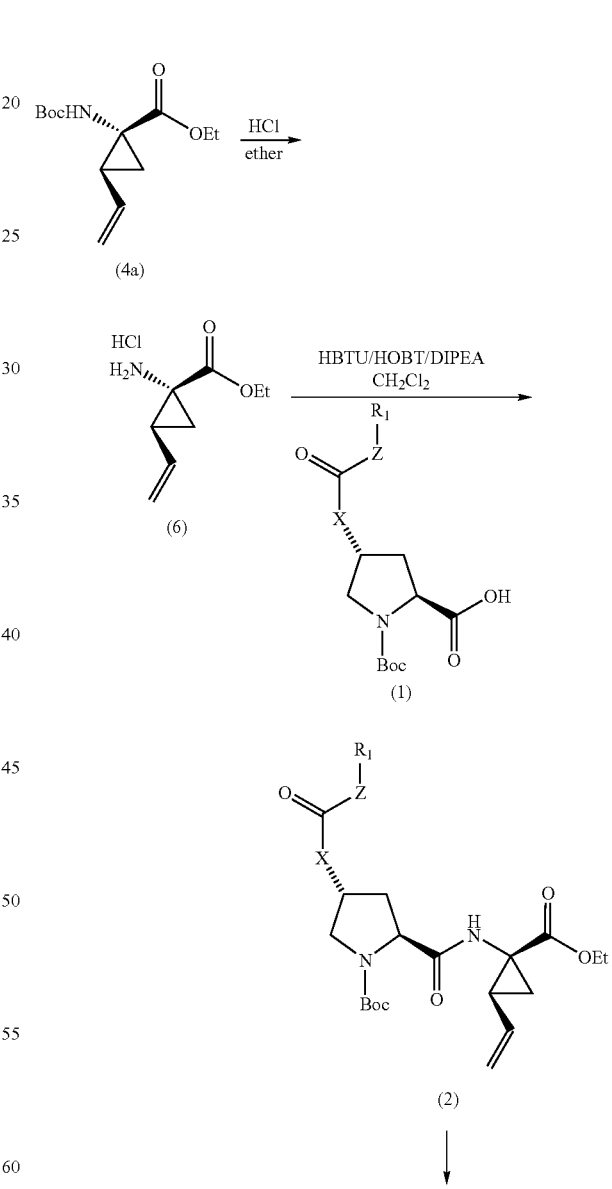

Treatment of commercially available, or readily synthesized imine 1 with 1,4-dihalobutene 2 in presence of a base provides the imine 3. Acid hydrolysis of 3 then provides B as a mixture of diastereoisomers. It is preferred that for compounds 3 and B that the vinyl group is syn to the ester. The amine moiety of B can protected using a Boc group to provide the fully protected amino acid 4a/4b. This intermediate is a racemate, a 1:1 mixture of enantiomers, and each enantiomer is shown in the above scheme. Racemate 4a/4b can be resolved by an enzymatic process wherein the ester moiety of 4 is cleaved to provide the corresponding carboxylic acid. Without being bound to any particular theory, it is believed that this reaction is selective in that one of the enantiomers, that is 4b, with the absolute stereochemistry designated (1S, 2R) undergoes the reaction at a much greater rate than its mirror image, 4a, providing for a kinetic resolution of racemate 4a/4b. Hence, in the course of this enzyme catalyzed ester cleavage, 4b will be readily converted to the corresponding acid 5, whereas 4a will remain as unreacted starting material. Once the reaction is terminated, the carboxylic acid 5 and recovered starting material 4a, can be separated by rountine methods such as aqueous extraction methods or chromatography. As shown below, intermediate 4a can be readily converted into compounds of Formula 1 by the methods described herein. For example, removal of the Boc group from intermediate 4a can be accomplished by subjecting 4a to an acid such as HCl in a solvent such as ether, to provide the corresponding amine hydrochloride 6. Intermediate 6 can then be coupled to a functionalized proline moiety 1 to provide the P1-P2 dipeptide 2. Intermediates like 2 can be converted to compounds of Formula 1 by the methods described herein.

Compounds of Formula 1 can also be converted into other compounds of Formula I as described herein. An example of such a process is shown in Scheme 9, wherein a compound of Formula I (1) which bears a Boc group at the P4 position is converted into a compound of Formula I (3) wherein said compound bears a urea group at the P4 position. The conversion of 1 to 3 can be carried out in a two step process the first of which is the conversion of 1 to amine 2 by treatment of 1 with an acid such as TFA in a solvent such as methylene chloride. The resulting amine TFA salt can be treated with an isocyanate in the presence of one equivalent of base to provide a compound of Formula I (3) wherein the P3 moiety is capped with a urea. As previously noted one skilled in the art will recognize that intermediate 2 can be used as starting material for the preparation of compounds of Formula I wherein the P3 group is capped with an amide or a carbamate. The construction of said compounds of Formula I can be achieved using standard conditions for the formation of said P4 functionalities from amines.

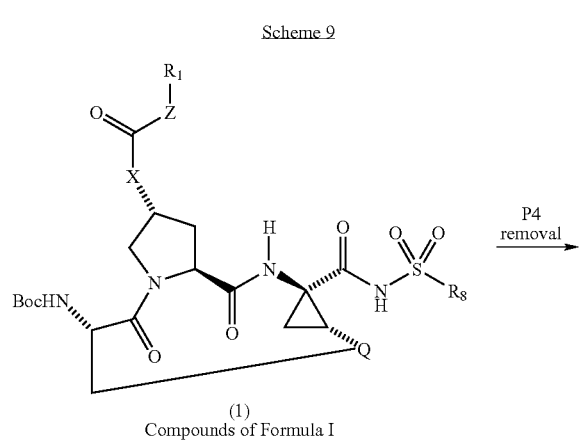

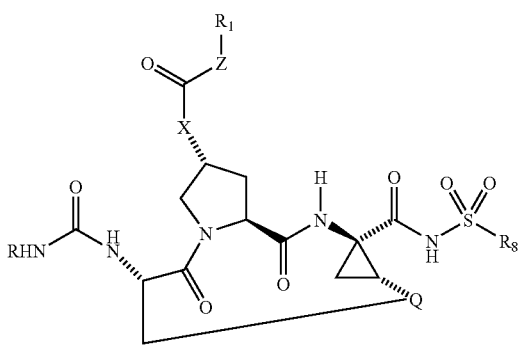

Compounds of Formula I (3)

Compounds of Formula 1 which house a nitrogen as part of the Q element can be prepared and further modified using chemistry described herein and additionally chemistry well established in the art. For example intermediate 1 of Scheme 10 can be converted to Compounds of Formula 1 using the above described acylation chemistry. For example 1 upon treatment with a carbamoyl chloride should provide the corresponding carbamate 3. In the execution of this reaction it may be necessary to heat the reaction mixture and/or add a base to the reaction mixture. As an alternative procedure for the construction of intermediate 3, the alcohol functionality in 1 can be converted into an activated carbonate by simple acylation of 1 using p-nitrophenylchloroformate in the presence of a base such as diisopropylethylamine. It may be necessary to add a catalytic amount of DMAP to enhance the rate of such a reaction. Intermediate 2 can then be converted into compound 3 by treatment with tetrahydroisoquinoline (a) as shown in a solvent such as THF or dichloroethane. In the execution of such a reaction it may be necessary to heat the reaction mixture to enhance the reaction rate. In addition in the conversion of 2 to 3 it may be necessary to activate the amine (a) as a means to generate a more reactive nucleophile. This can be accomplished by deprotonation of the amine, which in this example is tetrahydroisoquinoline, with a base such a butyl lithium to provide intermediate (b). This lithium amide (b) can be added to intermediate 2 for the formation of 3.

One skilled in the art will readily recognize that 1 upon treatment with acid chlorides, in the presence of a base such as pyridine and in a solvent such as dichloromethane, should provide for the formation of esters. For example, treatment of 1 with benzoylchloride in the presence of excess pyridine in a solvent such as dichloromethane should provide for the formation of ester 4. In such an example it may be necessary to heat the reaction mixture to effect the formation of 4. In addition, a catalyst such a DMAP may be required for such a conversion.

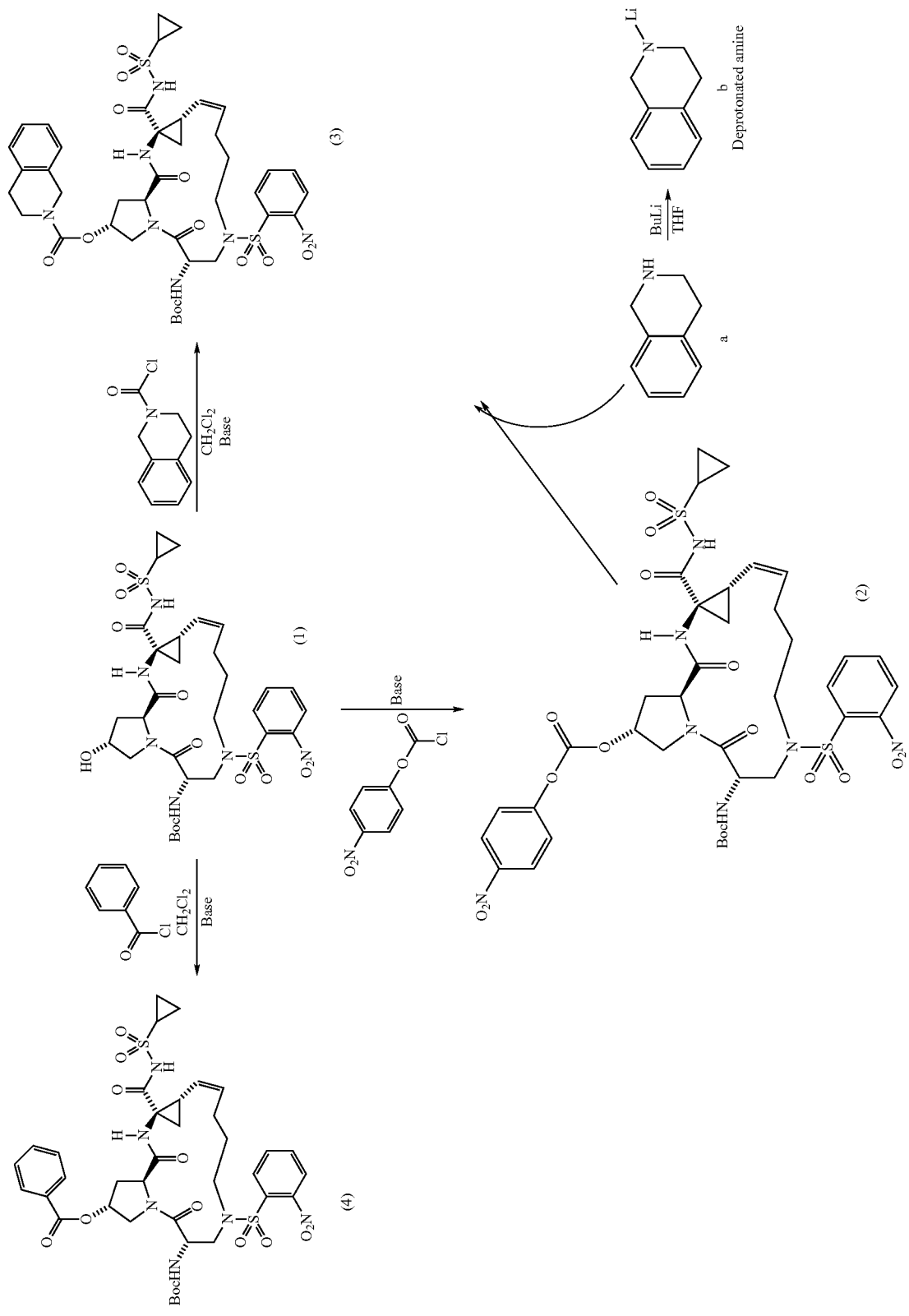
Scheme 10

Intermediate 3 of scheme 10 can be further modified wherein the sulfonamide group is replaced with an amide or carbamate or amine derivative (see Scheme 11). For example, the sulfonamide group can be readily removed by treatment of 3 with phenylthiol in a solvent such as acetonitrile and in the presence of a base such as potassium carbonate to provide the amine 4. This compound can be converted to other compounds of Formula I by simple acylation chemistry which should provide for the formation of amides, ureas or carbamates. Alternatively one skilled in the art would recognize that the secondary amine of compound 4 can be converted to the corresponding tertiary amine by reductive amination. For example, as shown, treatment of 4 with sodium cyanoborohydride in the presence of acetic acid and the hemiethylketal of cyclopropanone, in a solvent such as dichoroethane should provide the corresponding cyclopropylamine derivative 5. One skilled in the art would recognize that the hemiketal reagent could be replaced with an aldehyde such as isobutyrylaldehyde.

One skilled in the art will also recognize that amine 4, can readily be converted to amides or alternatively ureas or alternatively carbamates, by the treatment of 4 with the requisite acid chlorides, carbamoylchlorides or alkylchoroformates, respectively. In the example cited below 4 is acylated with dimethylcarbamoylchloride in a solvent such as dichloromethane and optionally in the presence of a base such as diisopropylamine, to provide the dimethylurea derivative 6. In the execution of such a reaction it may be necessary to add DMAP as a catalyst.

Scheme 11
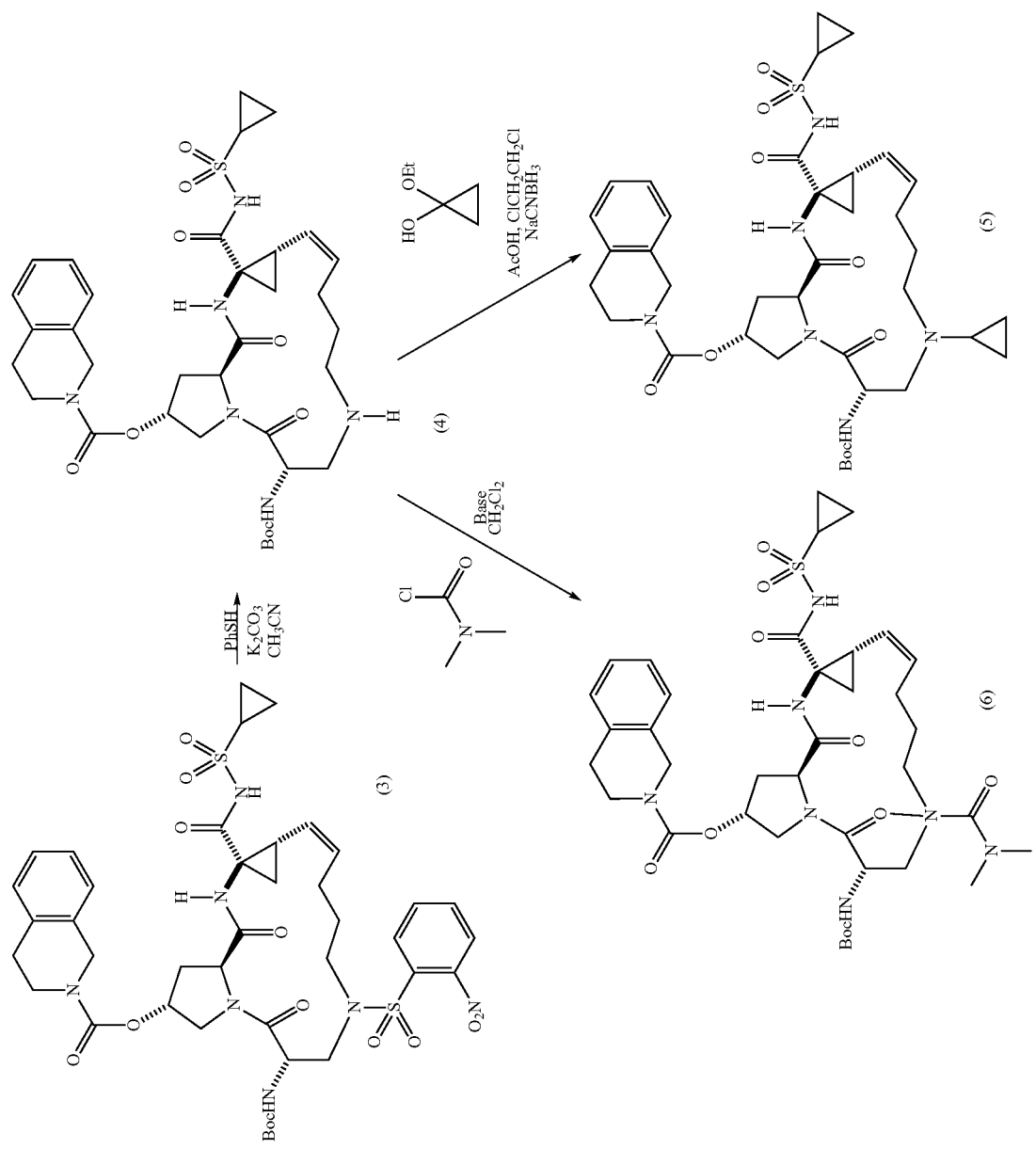

Intermediate 1 of Scheme 10 can be prepared by the process outline in Scheme 12. Therein, amino acid 1 is coupled with P2-P1 dipeptide 2, using agents such as HATU in conjunction with an amine bases such as morpholine, and in a solvent such as DMF. The resulting tripeptide 3, is then converted to the macrocycle 4 using a ring closing metathesis reaction. There are a number of reagents developed for this process as for example the ruthenium species shown, which is commonly referred to as the "Grubbs Second Generation catalyst". Subjecting 3 to such a ring closing metathesis reagent should provide the desired macrocycle 4. This reaction can be conducted in solvents such as methylene chloride, dichloroethane, or benzene. Moreover, in some examples it may be necessary to heat the reaction vessel to affect cyclization or to drive the reaction to completion.

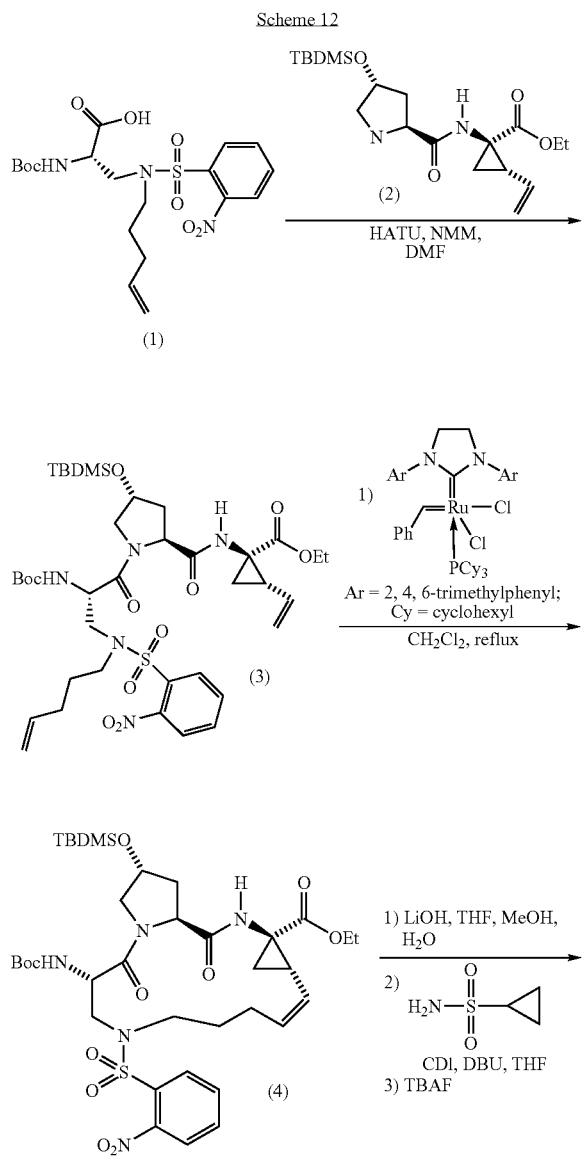

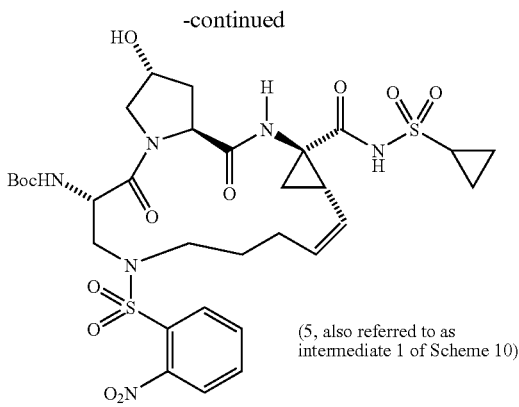

(5, also referred to as intermediate 1 of Scheme 10)

EXAMPLES

The specific examples that follow illustrate the syntheses of the compounds of the present invention, and are not to be construed as limiting the scope of the claims which follow. The methods may be adapted to variations in order to produce compounds embraced by this invention but not specifically disclosed. Further, variations of the methods to produce the same compounds in somewhat different manner will also be evident to one skilled in the art.

Chemical abbreviations commonly used to identify chemical compounds disclosed herein include Bn: benzyl; Boc: tert-butyloxycarbonyl {Me$_3$COC(O)}; BSA: bovine serum albumin; CDI: carbonyldiimidazole; DBU: 1,8-diazabicy-clo [5.4.0]-undec-7-ene; CH$_2$Cl$_2$=DCM: methylene chloride; TBME: tert-butyl methyl ether; DEAD: diethylazodicarboxylate; DIAD: diisopropylazodicarboxylate; DIEA: diisopropylethylamine; DIPEA: diisopropylethylamine; 4-DMAP: 4-dimethylaminopyridine; DCC: 1,3-dicyclohexylcarbodiimide; DMF: dimethylformamide; DMSO: dimethylsulfoxide; DPPA: diphenylphosphoryl azide; Et: ethyl; EtOH: ethanol; EtOAc: ethyl acetate; Et$_2$O: diethyl ether; Grubb's Catalyst: bis(tricyclohexylphosphine)benzylidene ruthenium (IV) dichloride; Grubb's 2$^{nd}$ Generation Catalyst: tricyclohexylphosphine[1,3-bis(2,4,6-trimethylphenyl)-4,5-dihydroimidazol-2-ylidene][benzylidene]ruthenium (IV) dichloride; HATU: [O-(7-azabenzotriazol-1-yl)-N,N,N',N'-tetramethyluronium hexafluorophosphate; HBTU: [O-(1H-benzotriazol-1-yl)-N,N,N',N'-tetramethyluronium hexafluorophosphate; HOBT, 1-hydroxybenzotriazole; HOAT, 1-hydroxy-7-azabenzotriazole; HPLC: high performance liquid chromatography; MS: mass spectrometry; Me: methyl; MeOH: methanol; NMM: N-methylmorpholine; NMP: N-methylpyrrolidine; Pr: propyl; PPA: polyphosphoric acid; TBAF: tetra-n-butylammonium fluoride; 1,2-DCE or DCE: 1,2-dichloroethane; TFA: trifluoroacetic acid; THF: tetrahydrofuran. Solution percentages express a weight to volume relationship, and solution ratios express a volume to volume relationship, unless stated otherwise. Nuclear magnetic resonance (NMR) spectra were recorded either on a Bruker 300, 400 or 500 megahertz (MHz) spectrometer; the chemical shifts (δ) are reported in parts per million. Flash chromatography was carried out on silica gel (SiO$_2$) according to Still's flash chromatography technique (*J. Org. Chem.* 1978, 43, 2923). Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+). Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million.

The examples, compounds and chemical intermediates of the present invention, described in the following examples, were prepared according to the following methods.

Example 1

Preparation of Sulfamides

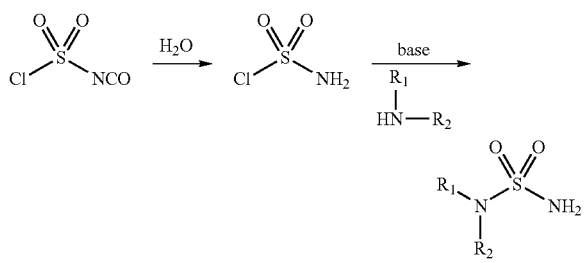

The intermediate sulfamoyl chloride was prepared by addition of water (1 equiv) in THF to a cold (-20° C.) stirred solution of chlorosulfonyl isocyanate (1 equiv) in THF and the resulting solution allowed to warm to 0° C. To this solution was added anhydrous Et$_3$N (1 equiv) followed by requisite secondary amine (1 equiv). The reaction mixture was warmed to room temperature, then filtered and the filtrate was rotary evaporated to afford the desired sulfamides. Said sulfamide was then coupled to a carboxylic acid to provide the desired acylsulfamide.

Example 2

Specific Procedure for the Preparation of an Acylsulfamide Intermediate

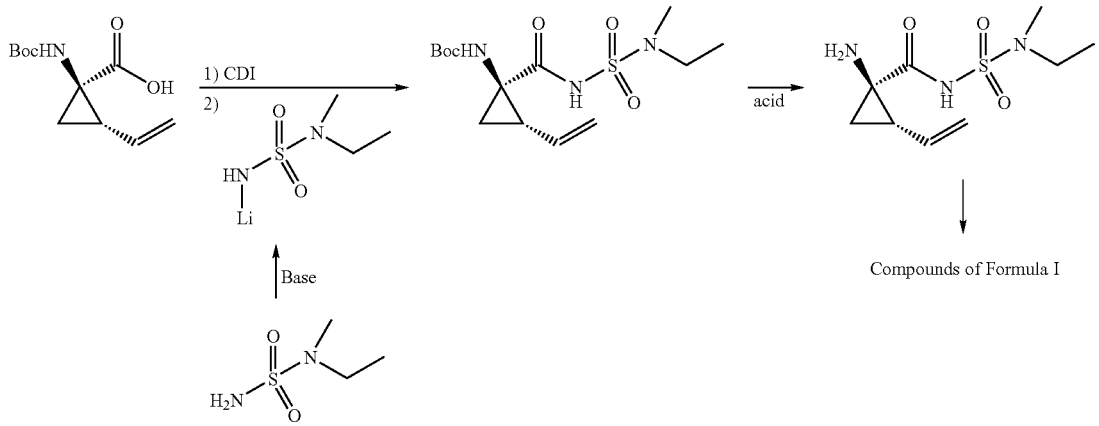

To a solution of (1R,2S) 1-tert-butoxycarbonylamino-2-vinyl-cyclopropanecarboxylic acid (217 mg, 1.194 mmol) in THF (5 mL), CDI (290 mg, 1.791 mmol) was added and the reaction mixture was heated under reflux for 45 min. In another round-bottomed flask, LiHMDS (1.0 M solution in hexanes, 2.4 mL, 2.4 mmol) was added to a solution of N-ethylmethylsulfamide (330 mg, 2.388 mmol) in THF (5 mL) and the reaction mixture was stirred at rt for 1 h. Two reaction mixtures were added together and stirred at rt for 2 h. Water was added to quench the reaction and the reaction solution was extracted with EtOAc. The oraganic layer was separated and dried over MgSO$_4$. Evaporation of solvent gave crude product which was purified by Prep. HPLC to afford desired N-acylsulfamide. N-acylsulfamide was then dissolved in 4N HCl solution in dioxane (2 mL) and stirred at rt for 4 h.

Evaporation of solution give brownish oil as HCl salt. (112 mg, 33% yield). $^1$H NMR (400 Mz, CD$_3$OD) δ 1.16 (t, J=7.21Hz, 3H), 1.68 (dd, J=10.03, 7.83Hz, 1H), 2.15 (m, 1H), 2.37 (m, 1H), 2.89 (s, 3H), 3.30 (m, 2H), 5.31 (d, J=10.27Hz, 1 H), 5.42 (d, J=17.12Hz, 3H), 5.68 (m, 1H). LC-MS (retention time: 0.883 min.), MS m/z 270 (M+Na$^+$).

Example 3

Preparation of racemic (1R,2S)/(1S,2R)-1-amino-2-vinylcyclopropane carboxylic acid ethyl ester hydrochloride (Method A and Method B)

The named compound was made racemic by each of the following methods A and B.

Method A

Preparation of N-Benzyl Imine of Glycine Ethyl Ester

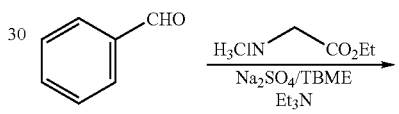

-continued

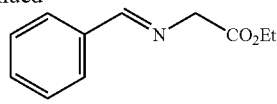

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous NaHCO₃ (1 L) and brine (1 L). The solution was dried over MgSO₄, concentrated in vacuo to afford 392.4 g of the N-benzyl imine product as a thick yellow oil that was used directly in the next step. $^1$H NMR (CDCl₃, 300 MHz) δ 1.32 (t, J=7.1Hz, 3H), 4.24 (q, J=7.1Hz, 2H), 4.41 (d, J=1.1Hz, 2H), 7.39-7.47 (m, 3H), 7.78-7.81 (m, 2H), 8.31 (s, 1H).

Preparation of racemic
N-Boc-(1R,2S)/(1S,2R)-1-amino-2-vinylcyclopropane
carboxylic acid ethyl ester

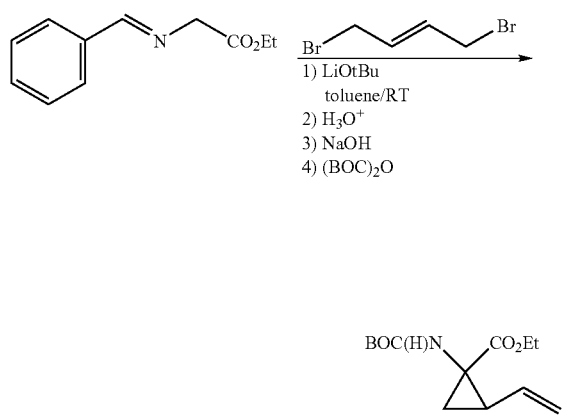

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO₄) and concentrated to a volume of 1 L. To this solution of free amine, was added BOC₂O or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over MgSO₄ and concentrated in vacuo to afford 80 g of crude material. This residue was purified by flash chromatography (2.5 Kg of SiO₂, eluted with 1% to 2% MeOH/CH₂Cl₂) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDC₃, 300 MHz) δ 1.26 (t, J=7.1Hz, 3H), 1.46 (s, 9H), 1.43-1.49 (m, 1H), 1.76-1.82 (br m, 1H), 2.14 (q, J=8.6Hz, 1H), 4.18 (q, J=7.2Hz, 2H), 5.12 (dd J=10.3, 1.7Hz, 1H), 5.25 (br s, 1H), 5.29 (dd, J=17.6, 1.7 Hz, 1H), 5.77 (ddd, J=17.6, 10.3, 8.9Hz, 1H); MS m/z 254.16 (M−1).

Preparation of Racemic (1R,2S)/(1S,2R)
1-amino-2-vinylcyclopropane carboxylic acid ethyl
ester hydrochloride

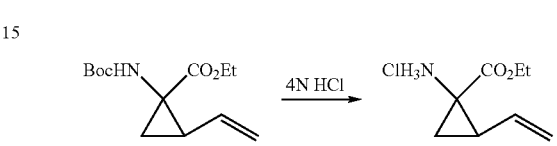

N-Boc-(1R,2S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quanitative yield (7 g, 100%). $^1$H NMR (methanol-d₄) δ 1.32 (t, J=7.1, 3H), 1.72 (dd, J=10.2, 6.6Hz, 1H), 1.81 (dd, J=8.3, 6.6Hz, 1H), 2.38 (q, J=8.3Hz, 1H), 4.26-4.34 (m, 2H), 5.24 (dd, 10.3, 1.3Hz, 1H) 5.40 (d, J=17.2, 1H), 5.69-5.81 (m, 1H).

Method B

Preparation of Racemic
N-Boc-1-amino-2-vinylcyclopropane carboxylic acid
ethyl ester hydrochloride To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et$_2$O (530 mL), 1N aq. HCl solution (106 mL, 106 mmol) added and the resulting biphasic mixture stirred for 3.5 h at rt. The layers were separated and the aqueous layer was washed with Et$_2$O (2×) and basified with a saturated aq. NaHCO$_3$ solution. The desired amine was extracted with Et$_2$O (3×) and the combined organic extract was washed with brine, dried (MgSO$_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Example 4

Resolution of N-Boc-(1R,2S)/(1S,2R)-1-amino-2-vinylcyclopropane carboxylic acid ethyl ester

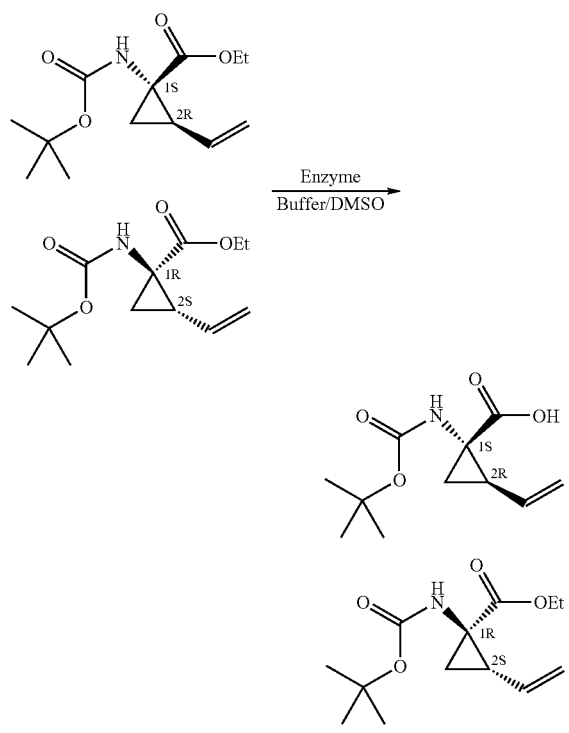

racemate: 1:1 mixture of (1R, 2S) and (1S, 2R)

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO$_3$ (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% @ 210 nanomolar ("nM"), containing no acid; 100% enantiomeric excess ("ee").

The aqueous layer from the extraction process was then acidified to pH 2 with 50% H$_2$SO$_4$ and extracted with MTBE (2×2 L). The MTBE extract was washed with water (3×100 mL) and evaporated to give the acid as light yellow solid (42.74 g; purity: 99% @ 210 nM, containing no ester).

|  | ester | acid |
|---|---|---|
| High Resolution Mass Spec | (+) ESI, C13H22NO4, [M + H]$^+$, cal. 256.1549, found 256.1542 | (−) ESI, C11H16NO4, [M − H]$^−$, cal. 226.1079, found 226.1089 |

NMR observed chemical shift
Solvent: CDCl$_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J=9.0Hz) | 34.1 | 2.17 (q, J=9.0Hz) | 35.0 |
| 3a | 1.76 (br) | 23.2 | 1.79 (br) | 23.4 |
| 3b | 1.46 (br) |  | 1.51, (br) |  |
| 4 | — | 170.8 | — | 175.8 |
| 5 | 5.74 (ddd, J=9.0, 10.0, 17.0 Hz) | 133.7 | 5.75 (m) | 133.4 |
| 6a | 5.25 (d, J=17.0Hz) | 117.6 | 5.28 (d, J=17.0Hz) | 118.1 |
| 6b | 5.08 (dd, J=10.0, 1.5Hz) |  | 5.12 (d, J=10.5Hz) |  |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J=7.5Hz) | 14.2 | — | — |

Resolution B

To 0.5 mL 100 millimolar ("mM") Heps•Na buffer (pH 8.5) in a well of a 24 well plate (capacity: 10 ml/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("μl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Resolution C

To 0.5 ml 100 mM Heps•Na buffer (pH 8.5) in a well of a 24 well plate (capacity: 10 mL/well), 0.1 ml of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 μl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Samples analysis was carried out in the following manner:

1) Sample preparation: About 0.5 ml of the reaction mixture was mixed well with 10 volume of EtOH. After centrifugation, 10 μl of the supernatant was injected onto HPLC column.

2) Conversion determination:

Column: YMC ODS A, 4.6×50 millimeter ("mm"), S-5 μm

Solvent: A, 1 mM HCl in water; B, MeCN

Gradient: 30% B for 1 min; 30% to 45% B over 0.5 min; 45% B for 1.5 min; 45% to 30% B over 0.5 min.

Flow rate: 2 m/min

UV Detection: 210 nM

Retention time: acid, 1.2 min; ester, 2.8 min.

3) Enantio-excess determination for the ester:

Column: CHIRACEL OD-RH, 4.6×150 mm, S-5 μm

Mobile phase: MeCN/50 mM $HClO_4$ in water (67/33)

Flow rate: 0.75 ml/min.

UV Detection: 210 nM.

Retention time:

(1S,2R)-1-amino-2-vinylcyclopropane carboxylic acid 5.2 min;

Racemate (1R,2S)/(1S,2R)-1-amino-2-vinylcyclopropane carboxylic acid ethyl ester 18.5 min and 20.0 min;

(1R,2S)-1-amino-2-vinylcyclopropane carboxylic acid ethyl ester 18.5 min.

Resolution D

5 L of 0.3 M sodium phosphate buffer (pH 8) was maintained at 38° C. in a 20 Liter jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funel. The reaction temperature was then adjusted to 48° C. After 21 hours, enantio-excess of the ester reached 99.3%. Heating was stopped at 24 hour and the reaction was slowly cooled down to room temperature (about 25° C.) and stirred overnignt. pH of the reaction mixture was adjusted to 8.5 with 10 N NaOH and the mixture was extracted with MTBE (2×4 L). The combined MTBE extract was washed with 5% $NaHCO_3$ (3×400 ml) and water (3×400 ml), and evaporated to give enantiomerically pure N-Boc-(1R,2S)/-1-amino-2-vinylcyclopropane carboxylic acid ethyl ester as light yellow crystal (259 g; purity: 96.9% @ 210 nM, containing no acid; 100% ee).

Resolution E

10 L of 0.1 M sodium phosphate buffer (pH 8) was maintained at 40° C. in a 20 Liter jacked reactor, stirred at 360 rpm. 1.5 liters of Alcalase 2.4 L (Novozymes North America Inc.) was added to the reactor. When temperature of the mixture closed to 38° C., pH was adjusted to 8.0 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 1 hour via an addition funnel. The reaction temperature was then adjusted to 40° C. After 3 hours, pH was adjusted to 8.0 with 10 N NaOH. After 21 hours, the reaction was cooled down to 25° C. pH of the reaction mixture was adjusted to 8.5 with 10 N NaOH and the mixture was extracted with MTBE (2×5 L). The combined MTBE extract was washed with 5% $NaHCO_3$ (3×500 ml) and water (3×200 ml), and evaporated to give 110 gram of yellow oil. The oil was set at room temperature under house vacuum and gave enantiomerically pure N-Boc-(1R,2S)/-1-amino-2-vinylcyclopropane carboxylic acid ethyl ester as colorless long rod crystal (101 g; purity: 97.9% @ 210 nM, containing no acid; 100% ee).

The crystal structure enantiomerically pure N-Boc-(1R,2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of
N-Boc-(1R,2S)-1-amino-2-vinylcyclopropane
carboxylic acid ethyl ester

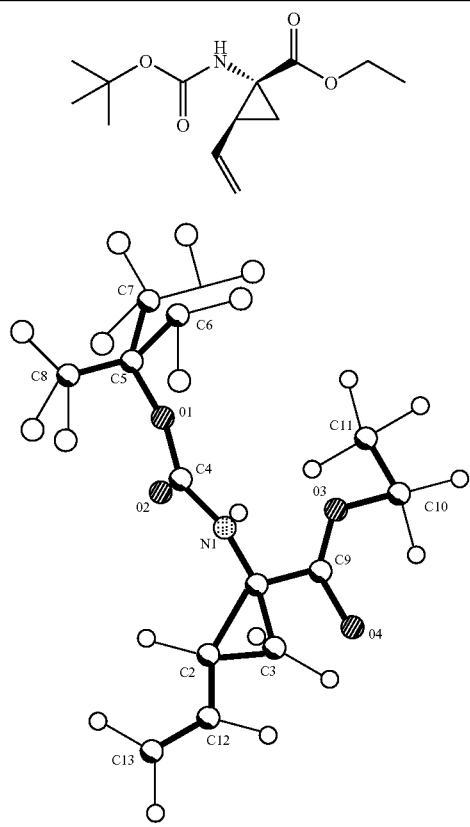

Crystal Data:

Chemical formula: $C_{13}H_{21}N_1O_4$
Crystal system: Orthorhombic
Space Group: $P2_12_12_1$
α = 5.2902(1) Å    α = 90°
b = 13.8946(2) Å   β = 90°
c = 19.9768(3) Å   γ = 90°
v = 1468.40(4) Å³
Z = 4    $d_x$ = 1.155 g cm⁻³
No. of reflections for lattice parameters: 6817
θ range for lattice parameters (°): 2.2-65.2
Absorption coefficient (mm⁻¹): 0.700

Experimental:

Crystallization

Crystal source: MTBE
Crystal description: Colorless rod
Crystal size (mm): 0.12 × 0.26 × 0.30
Data Collection Temperature (K): 293
$θ_{max}$ (°): 65.2 (Cu Kα)
No. of reflections measured: 7518
No. of independent reflections: 2390 ($R_{int}$ = 0.0776)
No. of observed reflection (1 ≧ 2 σ): 2284
Absorption correction ($T_{min}$-$T_{max}$): 0.688-1.000

Resolution F

5 L of 0.2 M sodium borate buffer (pH 9) was maintained at 45° C. in a 20 liter jacked reactor, stirred at 400 rpm. Three liter of DI water and four liters of Savinase 16 L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 min, via an addition funnel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hour, temperature was lowered to 35° C. At 42 hour, temperature was raised to 48° C. and pH was adjusted to 9.0 with 10 N NaOH. Heating was stopped at 48 hour and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% $NaHCO_3$ (6×300 ml) and water (3×300 ml), and evaporated to give enantiomerically pure N-Boc-(1R,2S)/-1-amino-2-vinylcyclopropane carboxylic acid ethyl ester as light yellow crystal (101A g; purity: 95.9% @ 210 nM, containing no acid; 98.6% ee).

Example 5

Step 1: Preparation of ethyl 1 (R)-amino-2(S)-vinylcyclopropane carboxylate hydrochloride

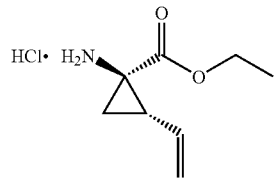

Ethyl 1(R)-tert-butoxycarbonylamino-2(S)-vinylcyclopropanecarboxylate (8.5 g, 33.3 mmol) was stirred under an $N_2$ atmosphere with 200 mL of 4N HCl/dioxane (Aldrich) at rt for 3 h. The solvent was removed under reduced pressure keeping the temperature below 40 C. This gave 6.57 g (~100%) of ethyl 1(R)-amino-2(S)-vinylcyclopropanecarboxylate hydrochloride as a light tan solid. ¹H NMR (300 MHz, $CD_3OD$) δ 1.31 (t, J=7.0Hz, 3H), 1.69-1.82 (m, 2H), 2.38 (q, J=8.8Hz, 1H), 4.29 (q, J=7.0Hz, 2H), 5.22 (d, J=10.3Hz, 1H), 5.40 (d, J=17.2Hz, 1H), 5.69-5.81 (m, 1H). MS m/z 156 (M⁺+1).

Step 2: Preparation of ethyl 1(R)-[1-tert-butoxycarbonyl-4(R)-hydroxypyrrolidine-2(S)-carboxamido]-2(S)-vinylcyclopropanecarboxylate

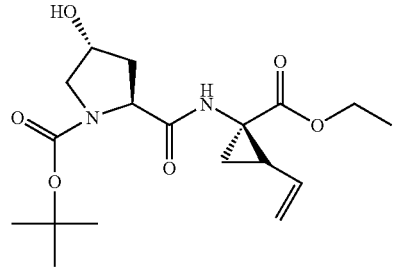

A stirred slurry of Boc-L-4-hydroxyproline (N-Boc (2S, 4R)-hydroxyproline) (10 g, 43.3 mmol) in 400 mL of methylene chloride was treated sequentially with N-methyl morpholine (9.3 mL, 84.7 mmol), HATU (19.5 g, 51.3 mmol), and ethyl 1(R)-amino-2(S)-vinylcyclopropanecarboxylate hydrochloride (9.1 g, 47.5 mmol). The gold homogeneous solution was stirred at rt under N₂ for 18 h, and then concentrated in vacuo to give a brown oil. This was partitioned between ethyl acetate and sat. aq. NaHCO₃. The organic phase was washed with brine, dried (MgSO₄), and concentrated in vacuo to give 15 g (94%) of ethyl 1(R)-[1-tert-butoxycarbonyl-4(R)-hydroxypyrrolidine-2(S)-carboxamido]-2(S)-vinylcyclopropanecarboxylate as a off-white solid: LC-MS (Xterra HPLC column: 3.0×50 mm length. Gradient: 100% Solvent A/0% Solvent B to 0% Solvent A/100% Solvent B. Gradient time: 3 min. Hold time: 1 min. Flow rate: 5 mL/min. Detector Wavelength: 220 nM. Solvent A: 10% MeOH/90% H₂O/0.1% TFA. Solvent B: 10% H₂O/90% MeOH/0.1% TFA.) (Retention time: 2.09 min), MS m/z 369 (M⁺+1).

Step 3: Preparation of ethyl 1(R)-[4(R)-hydroxypyrrolidine-2(S)-carboxamido]-2-(S)-vinylcyclopropanecarboxylate hydrochloride

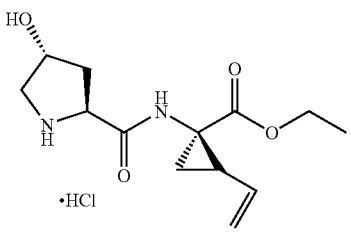

A stirred slurry of ethyl 1(R)-[1-tert-butoxycarbonyl-4(R)-hydroxypyrrolidine-2(S)-carboxamido]-2(S)-vinylcyclopropanecarboxylate (5.0 g, 13.6 mmol) was treated with 4N HCl/dioxane (20 mL) for 3 h. The reaction mixture was concentrated in vacuo to give 4.5 g (97%) of ethyl 1(R)-[4(R)-hydroxypyrrolidine-2(S)-carboxamido]-2(S)-vinylcyclopropanecarboxylate hydrochloride as a white solid: ¹H NMR (300 MHz, CD₃OD) δ 1.26 (t, J=7.14Hz, 3H), 1.46 (dd, J=9.70, 5.31Hz, 1 H), 1.80 (dd, J=8.23, 5.31Hz, 1H), 2.00-2.15 (m, 1H), 2.18-2.30 (m, 1H), 2.45 (dd, J=13.36, 7.50Hz, 1H), 3.36-3.48 (m, 1H), 4.11-4.24 (m, 2H), 4.44 (dd, J=10.25, 7.68Hz, 1H), 4.58-4.65 (m, 1H), 4.84-4.94 (m, 1H), 5.17 (d, J=1.83 Hz, 1H), 5.27-5.42 (m, 1H), 5.67-5.89 (m, 1H).

Example 6

Preparation of Cyclopropylsulfonamide Methods A and B

Method A

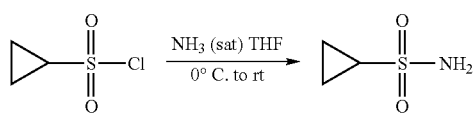

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1-2 mL of solvent remained, applied on to 30 g plug of SiO₂ (eluted with 30% to 60% EtOAc/Hexanes) to afford 3.45 g (100%) of cyclopropyl sulfonamide as a white solid. ¹H NMR (Methanol-d₄) δ 0.94-1.07 (m, 4H), 2.52-2.60 (m, 1H); ¹³C NMR (methanol-d₄) δ 5.92, 33.01.

Method B

Step 1: Preparation of N-tert-Butyl-(3-chloro)propylsulfonamide

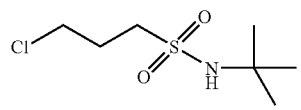

tert-Butylamine (3.0 mol, 315.3 mL) was dissolved in THF (2.5 L). The solution was cooled to −20° C. 3-Chloropropanesulfonyl chloride (1.5 mol, 182.4 mL) was added slowly. The reaction mixture was allowed to warm to rt and stirred for 24 h. The mixture was filtered, and the filtrate was concentrated in vacuo. The residue was dissolved in CH₂Cl₂ (2.0 L). The resulting solution was washed with 1 N HCl (1.0 L), water (1.0 L), brine (1.0 L) and dried over Na₂SO₄. It was filtered and concentrated in vacuo to give a slightly yellow solid, which was crystallized from hexane to afford the product as a white solid (316.0 g, 99%).

¹H NMR (CDCl₃) δ 1.38 (s, 9H), 2.30-2.27 (m, 2H), 3.22 (t, J=7.35Hz, 2H), 3.68 (t, J=6.2Hz, 2H), 4.35 (b, 1H).

Step 2: Preparation of Cyclopropanesulfonic acid tert-butylamide

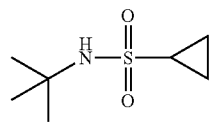

To a solution of N-tert-butyl-(3-chloro)propylsulfonamide (2.14 g, 10.0 mmol) in THF (100 mL) was added n-BuLi (2.5 M in hexane, 8.0 mL, 20.0 mmol) at −78° C. The reation mixture was allowed to warm up to room temperature over period of 1 h. The volatiles were removed in vacuo. The residue was partitioned between EtOAC and water (200 mL, 200 mL). The separated organic phase was washed with brine, dried over Na₂SO₄, filtered and concentrated in vacuo. The residue was recrystallized from hexane to yield the desired product as a white solid (1.0 g, 56%). ¹H NMR (CDCl₃) δ 0.98-1.00 (m, 2H), 1.18-1.19 (m, 2H), 1.39 (s, 9H), 2.48-2.51 (m, 1H), 4.19 (b, 1H).

Step 3: Preparation of cyclopropylsulfonamide

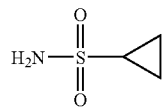

A solution of cyclopropanesulfonic acid tert-butylamide (110.0 g, 0.62 mol) in TFA (500 mL) was stirred at room temperature for 16 h. The volatile was removed in vacuo. The residue was recrystallized from EtOAC/hexane (60 mL/240 mL) to yield the desired product as a white solid (68.5 g, 91%).

$^1$H NMR (DMSO-d$_6$) δ 0.84-0.88 (m, 2H), 0.95-0.98 (m, 2H), 2.41-2.58 (m, 1H), 6.56 (b, 2H).

Example 7

Preparation of N-tert-butyl-(1-methyl)cyclopropylsulfonamide

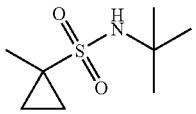

Step 1a Preparation of N-tert-butyl-(3-chloro)propylsulfonamide

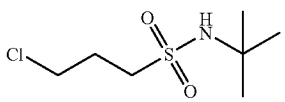

As shown above.

Step 1b. Preparation of N-tert-Butyl-(1-methyl)cyclopropylsulfonamide

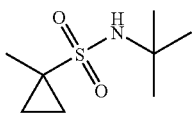

A solution of N-tert-butyl-(3-chloro)propylsulfonamide (4.3 g, 20 mmol) was dissolved in dry THF (100 mL) and cooled to –78° C. To this solution was added n-BuLi (17.6 mL, 44 mmol, 2.5 M in hexane) slowly. The dry ice bath was removed and the reaction mixture was allowed to warm to rt over a period of 1.5 h. This mixture was then cooled to –78° C., and a solution of n-BuLi (20 mmol, 8 mL, 2.5 M in hexane) was added. The reaction mixture was warmed to rt, recooled to –78° C. over a period of 2 h and a neat solution of methyl iodide (5.68 g, 40 mmol) added. The reaction mixture was allowed to warm to rt overnight, quenched with saturated NH$_4$Cl (100 mL) at rt. It was extracted with EtOAc (100 mL). The organic phase was washed with brine (100 mL), dried (MgSO$_4$), and concentrated in vacuo to give a yellow oil which was crystallized from hexane to afford the product as a slightly yellow solid (3.1 g, 81%): $^1$H NMR (CDCl$_3$) δ 0.79 (m, 2H), 1.36 (s, 9H), 1.52 (m, 2H), 1.62 (s, 3H), 4.10 (bs, 1H).

Step 1c: Preparation of 1-methylcyclopropylsulfonamide

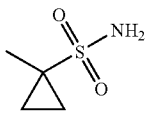

A solution of N-tert-butyl-(1-methyl)cyclopropylsulfonamide (1.91 g, 10 mmol) was dissolved in TFA (30 mL), and the reaction mixture stirred at rt for 16 h. The solvent was removed in vacuo to give a yellow oil which was crystallized from EtOAc/hexane (1:4, 40 mL) to yield Example 3, 1-methylcyclopropylsulfonamide, as a white solid (1.25 g, 96%):

$^1$H NMR (CDCl$_3$) δ 0.84 (m, 2H), 1.41 (m, 2H), 1.58 (s, 3H), 4.65 (bs, 2H). Anal. Calcd. For C$_4$H$_9$NO$_2$S: C, 35.54; H, 6.71; N, 10.36. Found: C, 35.67; H, 6.80; N, 10.40.

Example 8

Preparation of 1-Benzylcyclopropylsulfonamide

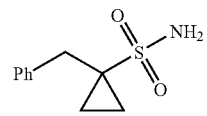

Steps 1b: Preparation of N-tert-Butyl-(1-benzyl)cyclopropyl-sulfonamide

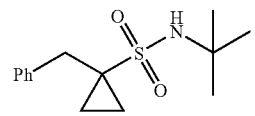

This compound was obtained in 60% yield using the procedure described for the synthesis of N-tert-butyl-(1-methyl)cyclopropylsulfonamide except 1.05 equivalents of benzyl bromide were used, followed by trituration with 10% EtOAc in hexane: $^1$H NMR (CDCl$_3$) δ 0.92 (m, 2H), 1.36 (m, 2H), 1.43 (s, 9H), 3.25 (s, 2H), 4.62 (bs, 1H), 7.29-7.36 (m, 5H).

Steps 1c: Preparation of 1-Benzylcyclo-propylsulfonamide

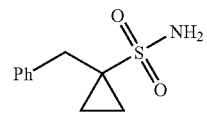

This compound 1-benzylcyclopropylsulfonamide, was obtained in 66% yield from N-tert-butyl(1-benzyl)cyclopropylsulfonamide using the procedure described for the synthesis of 1-methylcyclopropylsulfonamide, followed by recrystallization from the minimum amount of 10% EtOAc in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

Example 9

Preparation of 1-Propylcyclopropylsulfonamide

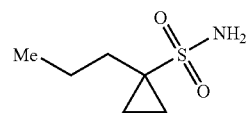

Steps 1b: Preparation of N-tert-Butyl-(1-benzyl)cyclopropyl-sulfonamide

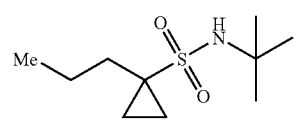

This compound was prepared using the process desribed for the preparation of 1-methylcyclopropylsulfonamide except propyl halide was utilized in place of methyl iodide in the second step of this process.

Example 10

Preparation of N-tert-Butyl-(1-allyl)cyclopropylsulfonamide

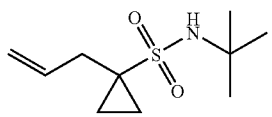

This compound, N-tert-Butyl-(1-allyl)cyclopropylsulfonamide, was obtained in 97% yield according to the procedure described in the synthesis of N-tert-Butyl-(1-methyl)cyclopropylsulfonamide except 1.25 equivalents of allyl bromide were used as electrophile. The compound was taken directly into the next reaction without purification: $^1$H NMR (CDCl$_3$) δ 0.83 (m, 2H), 1.34 (s, 9H), 1.37 (m, 2H), 2.64 (d, J=7.3Hz, 2H), 4.25 (bs, 1H), 5.07-5.10 (m, 2H), 6.70-6.85 (m, 1H).

Preparation of 1-allylcyclopropylsulfonamide

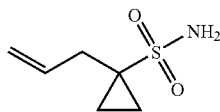

This compound, 1-allylcyclopropylsulfonamide, was obtained in 40% yield from N-tert-butyl-(1-allyl)cyclopropylsulfonamide according to the procedure described in the synthesis of 1-Methylcyclopropylsulfonamide. The compound was purified by column chromotography over SiO$_2$ using 2% MeOH in CH$_2$Cl$_2$ as the eluent: $^1$H NMR (CDCl$_3$) δ 0.88 (m, 2H), 1.37 (m, 2H), 2.66 (d, J=7.0Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

Example 11

Preparation of N-tert-Butyl-[1-(1-hydroxy)cyclohexyl]-cyclopropylsulfonamide

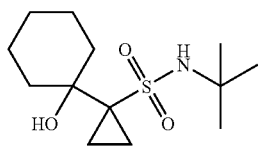

This compound was obtained in 84% yield using to the procedure described for the synthesis of N-tert-Butyl-(1-methyl)cyclopropylsulfonamide except 1.30 equivalents of cyclohexanone were used, followed by recrystallization from the minimum amount of 20% EtOAc in hexane: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (bs, 1H), 4.55 (bs, 1H).

Example 12

Preparation of 1-(1-cyclohexenyl)cyclopropyl-sulfonamide

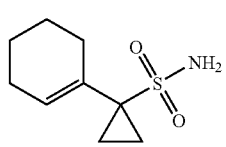

This compound, 1-(1-cyclohexenyl)-cyclopropylsulfonamide was obtained in 85% yield from N-tert-butyl-[1-(1-hydroxy)cyclohexyl]-cyclopropylsulfonamide $^1$H NMR (DMSO-d$_6$) δ 0.82 (m, 2H), 1.28 (m, 2H), 1.51 (m, 2H), 1.55 (m, 2H), 2.01 (s, 2 H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$−1).

Example 13

Preparation of N-tert-Butyl-(1-benzoyl)cyclopropyl-sulfonamide

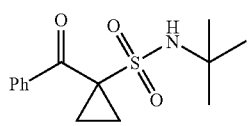

This compound was obtained in 66% yield using the procedure described for the synthesis of N-tert-Butyl-(1-methyl)cyclopropylsulfonamide except 1.2 equivalents of methyl benzoate was used as the electrophile. The compound was purified by column chromatography over SiO$_2$ using 30% to 100% CH$_2$Cl$_2$ in hexane: $^1$H NMR (CDCl$_3$) δ 1.31 (s, 9H), 1.52 (m, 2H), 1.81 (m, 2H), 4.16 (bs, 1H), 7.46 (m, 2H), 7.57 (m, 1H), 8.05 (d, J=8.5Hz, 2H).

Preparation of 1-benzoylcyclo-propylsulfonamide

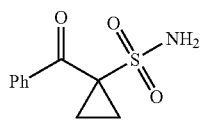

This compound 1-benzoylcyclopropyl-sulfonamide, was obtained in 87% yield from N-tert-butyl(1-benzoyl)cyclopropylsul-fonamide using the procedure described for the synthesis of 1-Methylcyclopropylsulfonamide, followed by recrystallization from the minimum amount of EtOAc in hexane: $^1$H NMR (DMSO-d$_6$) δ 1.39 (m, 2H), 1.61 (m, 2H), 7.22

(s, 2H), 7.53 (t, J=7.6Hz, 2H), 7.65 (t, J=7.6Hz, 1H), 8.06 (d, J=8.2Hz, 2H); $^{13}$C NMR (DMSO-d$_6$) δ 12.3, 48.4, 128.1, 130.0, 133.4, 135.3, 192.0.

Example 14

Preparation of N-tert-Butyl-(1-phenylaminocarboxy)-cyclopropylsulfonamide

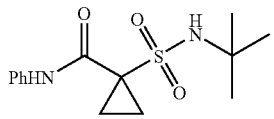

This compound was obtained in 42% yield using the procedure described for the synthesis of N-tert-Butyl-(1-methyl) cyclopropylsulfonamide using 1 equivalent of phenylisocyanate, followed by recrystallization from the minimum amount of EtOAc in hexane $^1$H NMR (CDCl$_3$) δ 1.38 (s, 9H), 1.67-1.71 (m, 4H), 4.30 (bs, 1H), 7.10 (t, J=7.5Hz, 1H), 7.34 (t, J=7.5Hz, 2H), 7.53 (t, J=7.5Hz, 2H).

Example 15

Preparation of cyclopropylsulfonylamine tert-butyl carbamate, a key intermediate in the preparation of C1-substituted cyclopropylsulfonamides

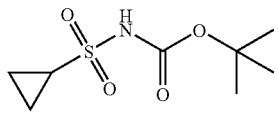

Step 1: Preparation of 3-chloropropylsulonamide

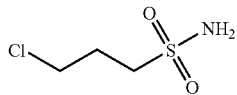

A solution of 3-chloropropanesulfonyl chloride (55 g, 310.7 mmol) was dissolved in THF (200 mL) and added dropwise over 30 minutes to a solution of NH$_4$OH (200 mL) cooled to 0° C. The reaction mixture was warmed to room temperature, stirred 1 hour, and the aqueous layer partioned multiple time with dichloromethane (4×500 mL). The combined dichloromethane layer was washed with 1N HCl (150 mL), water (150 mL), dried over MgSO$_4$, filtered, and concentrated in vacuo. The crude solid was recrystallized from the minimum amount of dichloromethane in hexanes to afford 3-chloropropylsulfonamide as a white solid (45.3 g, 93%). $^1$H NMR (CDCl$_3$) δ 2.34 (m, 2H), 3.32 (t, J=7.3Hz, 2H), 3.70 (t, J=6.2Hz, 2H), 4.83 (s, 2H); $^{13}$C NMR (CDCl$_3$) δ 27.10, 42.63, 52.57.

Step 2: Preparation of 3-chloropropylsulfonylamine tert-butylcarbamate

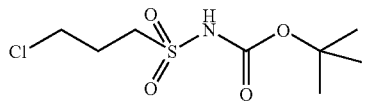

To a solution of 3-chloropropylsulfonamide (30.2 g, 191.5 mmol), triethylamine (30.2 mL, 217.0 mmol), and 4-DMAP (2.40 g, 19.6 mmol) in dichloromethane (350 mL) cooled to 0° C. was added slowly dropwise a solution of di-tert-butyl-dicarbonate (47.2 g, 216.9 mmol) in dichloromethane (250 mL) over 30 minutes. The reaction mixture was allowed to warm to room temperature, stirred an additional 3 hours and was partioned with 1N HCl (300 mL), water (300 mL), brine (300 mL), dried over MgSO$_4$, filtered, and concentrated in vacuo to afford the crude product. This material was triturated with 70 mL of 5% dichloromethane in hexanes to afford 3-chloropropylsulfonylamine tert-butylcarbamate as an off white solid (47.2 g, 96%): $^1$H NMR (CDCl$_3$) δ 1.51 (s, 9H), 2.33 (m, 2H), 3.60 (t, J=7.3Hz, 2H), 3.68 (t, J=6.21Hz, 2H); $^{13}$C NMR (CDCl$_3$) δ 26.50, 27.95, 42.37, 50.40, 84.76, 149.53.

Step 3: Preparation of cyclopropylsulfonylamine tert-butyl carbamate

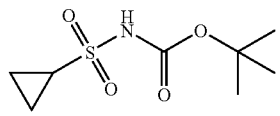

A solution of n-butyl lithium (74.7 mL, 119.5 mmol, 1.6M in hexane) was dissolved in dry THF (105 mL) and cooled to −78° C. under a Argon atmosphere. To this solution was added a solution of 3-chloropropylsulfonylamine tert-butyl-carbamate (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried (MgSO$_4$), filtered, and concentrated in vacuo to afford the cyclopropylsulfonylamine tert-butyl carbamate as a waxy off-white solid (12.08 g, 100%): $^1$H NMR (CDCl$_3$) δ 1.10 (m, 2H), 1.34 (m, 2H), 1.50 (s, 9H), 2.88 (m, 1H), 7.43 (s, 1H). $^{13}$C NMR (CDCl$_3$) δ 6.21, 28.00, 31.13, 84.07, 149.82.

Example 16

Preparation of 1-methoxy-methylcyclopropy-sulfonamide

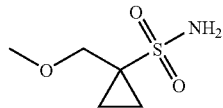

Step 1: Preparation of 1-methoxymethylcyclopropylsulfonylamine tert-butylcarbamate

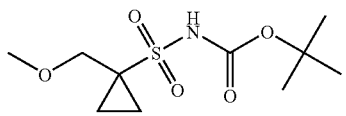

To a solution of cyclopropylsulfonylamine tert-butyl carbamate (1.0 g, 4.5 mmol) dissolved in THF (30 mL) cooled to −78° C., was added n-butyl lithium (6.4 mL, 10.2 mmol, 1.6M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried (MgSO$_4$), filtered, and concentrated to afford 1-methoxymethylcyclopropylsulfonylamine tert-butylcarbamate, as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

Step 2: Preparation of 1-methoxymethylcyclopropysulfonamide

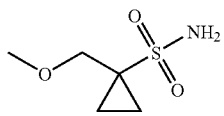

A solution of 1-methoxymethylcyclopropylsulfonylamine tert-butylcarbamate (1.14 g, 4.30 mmol) was dissolved in a solution of 50% TFA/dichloromethane (30 mL) and was stirred at room temperature for 16 hours. The solvent was removed in vacuo and the residue chromatographed over 80 g of SiO$_2$ (eluting with 0% to 60% ethyl acetate/hexanes to 1-methoxymethylcyclopropylsulfonamide as a white solid (0.55 g, 77% overall over two steps): $^1$H NMR (CDCl$_3$) δ 0.95 (m, 2H), 1.44 (m, 2H), 3.36 (s, 3H), 3.65 (s, 2H), 4.85 (s, 2H); $^{13}$C NMR (CDCl$_3$) δ 11.17, 40.87, 59.23, 74.80; LRMS m/z 183 (M$^+$+NH$_4$).

Example 17

Preparation of 1-cyclopropylmethylcyclopropylsulfonamide

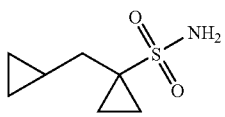

Step 1: Preparation of 1-cyclopropylmethylcyclopropylsulfonylamine tert-butylcarbamate

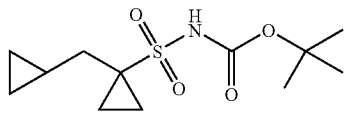

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate, except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0Hz, 2H).

Step 2: Preparation of 1-cyclopropylmethylcyclopropylsuftonamide

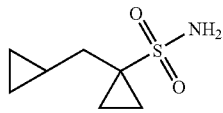

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromatography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

Example 18

Preparation of 1-propylcarbamoylcyclopropanesulfonamide

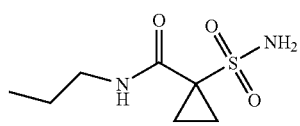

Step 1: Preparation of 1-propylcarbamoylcyclopropanesulfonamide tert-butylcarbamate

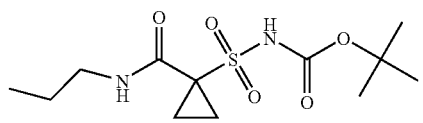

This compound was obtained in a crude 100% yield according to the procedure described for the synthesis of 1-methoxymethylcyclopropylsulfonylamine tert-butyl-carbamate except that 1.10 equivalents of n-propyl isocyanate was used as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0Hz, 2H).

Step 2: Preparation of
1-propylcarbamoylcyclopropanesulfonamide

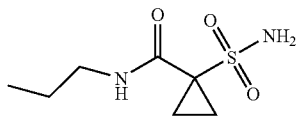

This compound was obtained in an optimized 50% yield from 1-propylcarbamoylcyclopropanesulfonamide tert-butylcarbamate according to the procedure described for the synthesis of 1-methoxymethylcyclopropylsulfonamide, except that no chromatography was used as the material was recrystallized from the minimum amount of dichloromethane/hexanes: $^1$H NMR (CDCl$_3$) δ 0.15 (m, 2H), 0.51 (m, 2H), 1.01 (m, 2H), 1.34 (m, 3H), 1.86 (d, J=7.0Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

Example 19

Preparation of 1-(3,5-dimethylisoxazol-4yl)carbamoylcyclopropanesulfonamide

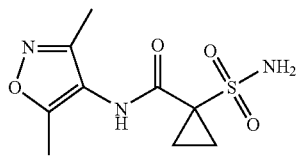

Step 1: Preparation of 1-(3,5-dimethylisoxazol-4-yl) carbamoylcyclopropanesulfonamide tert-butylcarbamate

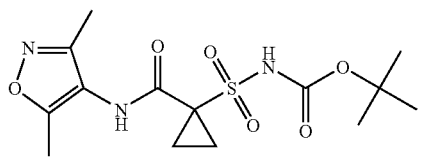

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

Step 2: Preparation of 1-(3,5-dimethylisoxazol-4-yl) carbamoylcyclopropanesulfonamide

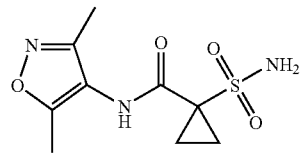

This compound was obtained in 50% yield (580 mg) from 1.62 g (4.52 mmol) of 1-(3,5-dimethylisoxazol-4-yl)carbamoylcyclo-propanesulfonamide tert-butylcarbamate using 30 mL (120 mmol) of 4N HCl/dioxanes, stirring overnight, concentration and chromatography over a Biotage 40M column (eluting with 0% to 5% methanol/dichloromethane: $^1$H NMR (methanol-d$_4$) δ 1.57 (m, 2H), 1.61 (m 2H), 2.15 (s, 3H), 2.30 (s, 3H), 4.84 (s, 3H); $^{13}$C NMR (methanol-d$_4$) δ 9.65, 10.94, 15.01, 46.11, 114.82, 159.45, 165.55, 168.15; LRMS m/z 260 (M$^+$+H).

Example 20

Preparation of cyclobutylsulfonamide from cylobutylbromide

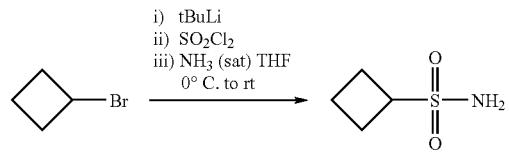

To a solution of 5.0 g (37.0 mmol) of cyclobutyl bromide in 30 mL of anhydrous diethyl ether (Et$_2$O) cooled to –78° C. was added 44 mL (74.8 mmol) of 1.7M tert-butyl lithium in pentanes and the solution slowly warmed to –35° C. over 1.5 h. This mixture was cannulated slowly into a solution of 5.0 g (37.0 mmol) of freshly distilled sulfuryl chloride in 100 mL of hexanes cooled to –40° C., warmed to 0° C. over 1 h and carefully concentrated in vacuo. This mixture was redissolved in Et$_2$O, washed once with some ice-cold water, dried (MgSO$_4$) and concentrated carefully. This mixture was redissolved in 20 mL of THF, added dropwise to 500 mL of saturated NH$_3$ in THF and was allowed to stir overnite. The mixture was concentrated in vacuo to a crude yellow solid and was recrystallized from the minimum amount of CH$_2$Cl$_2$ in hexanes with 1-2 drops of MeOH to afford 1.90 g (38%) of cyclobutylsulfonamide as a white solid. $^1$H NMR (CDCl$_3$) δ 1.95-2.06 (m, 2H), 2.30-2.54 (m, 4H), 3.86 (p, J=8Hz, 1H), 4.75 (brs, 2H); $^{13}$C NMR (CDCl$_3$) δ 16.43, 23.93, 56.29. HRMS m/z (M–H)$^-$ calcd for C$_4$H$_8$NSO$_2$: 134.0276, found 134.0282.

Example 21

Preparation of cyclopentyl sulfonamide

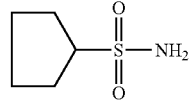

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 h and was then carefully concentrated in vacuo. This mixture was redissolved in Et₂O (200 mL), washed once with some ice-cold water (200 mL), dried (MgSO₄) and concentrated carefully. This mixture was redissolved in 35 mL of THF, added dropwise to 500 mL of saturated NH₃ in THF and was allowed to stir overnite. The mixture was concentrated in vacuo to a crude yellow solid, the residue filtered through 50 g of silica gel using 70% EtOAc-hexanes as the eluent and the solution was then concentrated. The residue was recrystallized from the minimum amount of CH₂Cl₂ in hexanes with 1-2 drops of MeOH to afford 2.49 g (41%) of cyclopentylsulfonamide as a white solid. $^{1}$H NMR (CDCl₃) δ 1.58-1.72 (m, 2H), 1.74-1.88 (m, 2H), 1.94-2.14 (m, 4H), 3.48-3.59 (m, 1H), 4.80 (bs, 2H); $^{13}$C NMR (CDCl₃) δ 25.90, 28.33, 63.54; MS m/e 148 (M−H)⁻.

Example 22

Preparation of cyclohexyl sulfonamide

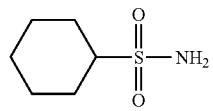

A solution of 18.5 mL (37.0 mmol) of 2M cyclohexylmagnesium chloride (TCI Americas) in ether was added dropwise to a solution of 3.0 mL (37.0 mmol) freshly distilled sulfuryl chloride in 100 mL of hexanes cooled to −78° C. The mixture was warmed to 0° C. over 1 h and was then carefully concentrated in vacuo. This mixture was redissolved in Et₂O (200 mL), washed once with some ice-cold water (200 mL), dried (MgSO₄) and concentrated carefully. This mixture was redissolved in 35 mL of THF, added dropwise to 500 mL of saturated NH₃ in THF and was allowed to stir overnite. The mixture was concentrated in vacuo to a crude yellow solid, the residue filtered through 50 g of silica gel using 70% EtOAc-hexanes as the eluent and was concentrated. The residue was recrystallized from the minimum amount of CH₂Cl₂ in hexanes with 1-2 drops of MeOH to afford 1.66 g (30%) of cyclohexyl-sulfonamide as a white solid: $^{1}$H NMR (CDCl₃) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5Hz, 1H), 4.70 (bs, 2H); $^{13}$C NMR (CDCl₃) δ 25.04, 25.04, 26.56, 62.74; MS m/e 162 (M−1)⁻.

Example 23

Preparation of Neopentylsulfonamide

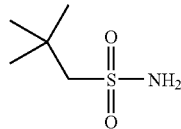

Following the procedure for the preparation of cyclohexylsulfonamide, 49 mL (37 mmol) of 0.75M neopentylmagnesium chloride (Alfa) in diethyl ether was converted to 1.52 g (27%) of neopentylsulfonamide as a white solid. $^{1}$H NMR (CDCl₃) δ 1.17 (s, 9H), 3.12 (s, 2H), 4.74 (brs, 2H); $^{13}$C NMR (CDCl₃) δ 29.46, 31.51, 67.38; MS m/e 150 (M−1)⁻.

Example 24

Preparation of cyclobutylcarbinylsutfonamide

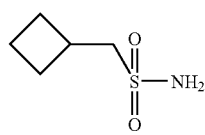

A solution of 12.3 g (83 mmol) of cyclobutylcarbinyl bromide (Aldrich) and 13.7 g (91 mmol) of sodium iodide in 150 mL of acetone was refluxed overnight and then cooled to room temperature. The inorganic solids were filtered off and the acetone and cyclopropylcarbinyl iodide (8.41 g, 46%) distilled off at ambient and 150 torr at 80° C., respectively.

A solution of 4.0 g (21.98 mmol) of cyclobutyl carbinyl iodide in 30 mL of anhydrous diethyl ether (diethyl ether) cooled to −78° C. was cannulated into a solution of 17 mL (21.98 mmol) of 1.3M sec-butyl lithium in cyclohexanes and the solution was stirred for 5 minutes. To this mixture was cannulated a solution of 3.0 g (21.98 mmol) of freshly distilled sulfuryl chloride in 110 mL of hexanes cooled to −78° C., the mixture warmed to room temperature over 1 hour and was then carefully concentrated in vacuo. This mixture was redissolved in diethyl ether, washed once with some ice-cold water, dried (MgSO₄), filtered, and concentrated carefully. This mixture was redissolved in 30 mL of THF, added dropwise to 500 mL of saturated NH₃ in THF and was allowed to stir overnight. The mixture was concentrated in vacuo to a crude yellow solid and was recrystallized from the minimum amount of dichloromethane in hexanes with 1-2 drops of methanol to afford 1.39 g (42%) of cyclobutyl carbinylsulfonamide as a white solid. $^{1}$H NMR (CDCl₃) δ 1.81-2.03 (m, 4H), 2.14-2.28 (m, 2H), 2.81-2.92 (m, 1H), 3.22 (d, J=7Hz, 2H), 4.74 (brs, 2); $^{13}$C NMR (CDCl₃) δ 19.10, 28.21, 30.64, 60.93; MS m/e 148 (M−1)⁻.

Example 25

Preparation of cyclopropylcarbinylsulfonamide

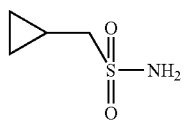

Using the procedure employed for the preparation of cyclobutylcarbinylsulfonamide, cyclopropylcarbinylsulfonamide was prepared from cyclopropylcarbinyl bromide (Aldrich) (see also JACS 1981, p. 442-445). $^{1}$H NMR (CDCl₃) δ 0.39-0.44 (m, 2H), 0.67-0.76 (m, 2H), 1.13-1.27

(m, 1H), 3.03 (d, J=7.3 Hz, 2H), 4.74 (brs, 2H); $^{13}$C NMR (CDCl$_3$) δ 4.33, 5.61, 59.93; MS m/e 134 (M−1).

Example 26

Preparation of 2-thiophenesulfonamide

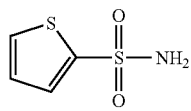

Prepared from 2-thiophenesulfonyl chloride (purchased from Aldrich) using the method of *Justus Liebigs Ann. Chem.*, 501, 1933, p. 174-182.

Example 27

Preparation of 4-bromobenzenesulfonamide

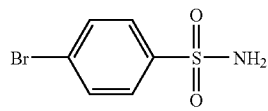

4-Bromophenylsulfonamide was prepared by treatment of commercially available 4-bromosulfonyl chloride with saturated ammonia in THF.

Example 28

Preparation of cyclopropanesulfonic acid (1-(R)-amino-2-(S)-vinyl-cyclopropanecarbonyl)amide HCl salt

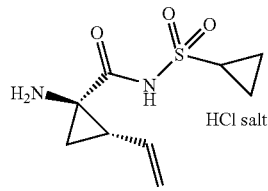

Step 1: Preparation of 1(R)-tert-butoxycarbonylamino-2(S)-vinyl-cyclopropanecarboxylic acid

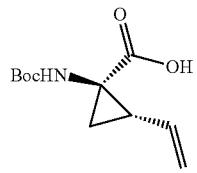

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature and quenched with 1N NaOH (15 mL) and water (20 mL). The resulting mixture was washed with ethyl acetate (20 mL), and the organic phase was extracted with 20 mL 0.5N NaOH. The combined aqueous phases were acidified with 1N HCl until pH 4 and extracted with ethyl acetate (3×40 mL). The combined organic extracts were washed with brine, dried (MgSO$_4$), filtered and concentrated to yield the title compound as a white solid (2.62 g, 87%). $^1$H NMR: (DMSO-d$_6$) δ 1.22-1.26 (m, 1H), 1.37 (s, 9H), 1.50-1.52 (m, 1H), 2.05 (q, J=9Hz, 1H), 5.04 (d, J=10Hz, 1H), 5.22 (d, J=17Hz, 1H), 5.64-5.71 (m, 1H), 7.18, 7.53 (s, NH (rotamers), 12.4 (br s, 1H)); MS m/z 228 (M$^+$+H).

Step 2: Preparation of cyclopropanesulfonic acid (1-(R)-tert-butoxycarbonylamino-2-(S)-vinylcyclopropanecarbonyl)-amide

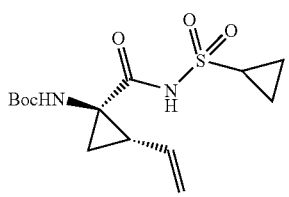

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1N HCl to pH 1 and THF was concentrated in vacuo. The suspension was extracted with ethyl acetate (2×50 mL) and the combined organic extracts were dried (Na$_2$SO$_4$), filtered, and concentrated. Purification by recystallization from hexanes-ethyl acetate (1:1) afforded the title compound (2.4 g) as a white solid. The mother liquor was purified by a Biotage 40S column (eluted 9% acetone in dichloromethane) to give a second batch of the title compound (1.1 g). Both batches were combined (total yield 92%). $^1$H NMR (DMSO-d$_6$) δ 0.96-1.10 (m, 4H), 1.22 (dd, J=5.5, 9.5Hz, 1H), 1.39 (s, 9H), 1.70 (t, J=5.5Hz, 1H), 2.19-2.24 (m, 1H), 2.90 (m, 1H), 5.08 (d, J=10Hz, 1H), 5.23 (d, J=17Hz, 1H), 5.45 (m, 1H), 6.85, 7.22 (s, NH (rotamers); MS m/z 331 (M$^+$+H).

Step 3: Preparation of cyclopropanesulfonic acid (1-(R)-amino-2-(S)-vinyl-cyclopropanecarbonyl) amide HCl salt

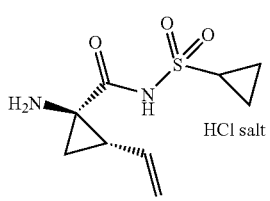

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1N HCl in diethyl ether (20 mL) and concentrated in vacuo. This procedure was repeated once. The resulting mixture was triturated from pentane and filtered to give the title compound as a hygroscopic, off-white solid (2.60 g, 92%). $^1$H NMR: (DMSO-$d_6$) δ 1.01-1.15 (m, 4H), 1.69-1.73 (m, 1H), 1.99-2.02 (m, 1H), 2.38 (q, J=9Hz, 1H), 2.92-2.97 (m, 1H), 5.20 (d, J=11 Hz, 1H), 5.33 (d, J=17Hz, 1H), 5.52-5.59 (m, 1H), 9.17 (br s, 3H); MS m/z 231 (M$^+$+H).

Example 29

Preparation of (1S,4R,6S,14S,18R)-7-cis-14-tert-butoxycarbonylamino-18-hydroxy-2,15-dioxo-3,16-diazatricyclo[14.3.0.0$^{4,6}$]nonadec-7-ene-4-carboxylic acid, Example 29

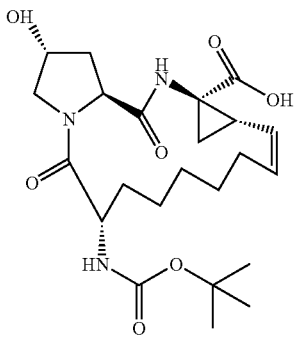

Example 29

Step 1: Preparation of 1-(2(S)-tert-Butoxycarbonylamino-non-8-enoyl)-4(R)-hydroxy-pyrrolidine-2(5)-carboxylic acid methyl ester

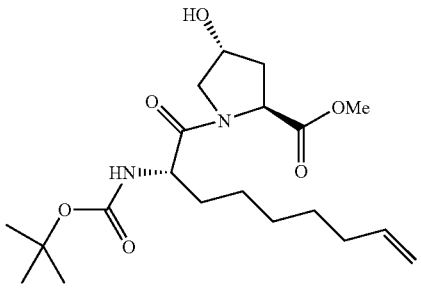

A solution of 2(S)-tert-butoxycarbonylamino-8-nonenoic acid (purchased from RSP Amino Acids)(3.5 g, 12.9 mmol) in 200 mL of DCM was treated sequentially with 4(R)-hydroxy-pyrrolidine-2(S)-carboxylic acid methyl ester hydrochloride (2.15 g, 11.8 mmol), N-methyl morpholine (4.25 mL, 38.6 mmol), and HATU (5.37 g, 14.1 mmol). The reaction mixture was stirred at rt under N$_2$ for 3 days, and then concentrated in vacuo. The residue was partitioned between ethyl acetate and pH 4 buffer (biphthalate). The organic phase was washed with sat. aq. NaHCO$_3$, dried (MgSO$_4$), and concentrated in vacuo to give the crude product. Flash chromatography (50% ethyl acetate/hexane to 100% ethyl acetate) gave 4.7 g (~100%) of 1-(2(S)-tert-Butoxycarbonylamino-non-8-enoyl)-4(R)-hydroxy-pyrrolidine-2(S)-carboxylic acid methyl ester as a colorless oil: $^1$H NMR (500 MHz, CD$_3$OD) δ 1.33-1.50 (m, 8H), 1.46 (s, 9H), 1.57 (m, 1H), 1.72 (m, 1H) 2.08 (m, 2 H), 2.28 (m, 1H), 3.72 (s, 3H,) 3.75-3.87 (m, 2H), 4.36 (m, 1H), 4.51 (bs, 1H), 4.57 (t, J=8.2Hz, 1H), 4.95 (d, J=10.4Hz, 1H), 5.01 (m, 1H), 5.83 (m, 1H); MS H); MS m/z 399 (M$^+$+1).

Step 2: Preparation of 1-{[1-(2(S)-tert-Butoxycarbonylamino-non-8-enoyl)-4-(R)-hydroxy-pyrrolidine-2(S)carbonyl]-(1R)-amino}-2(5)-vinyl-cyclopropanecarboxylic acid ethyl ester

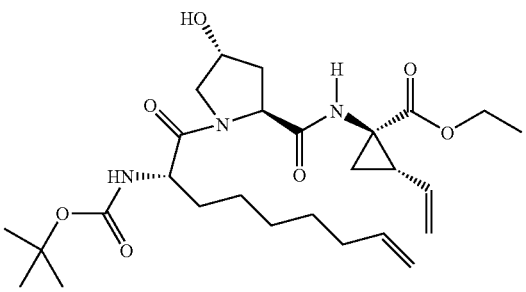

1-(2(S)-tert-Butoxycarbonylamino-non-8-enoyl)-4(R)-hydroxy-pyrrolidine-2(S)-carboxylic acid methyl ester (4.7 g, 11.8 mmol) was dissolved in THF (80 mL), methanol (20 mL), and water (40 mL). Powdered lithium hydroxide (5.6 g, 233 mmol) was added. The light yellow slurry was stirred at rt under N$_2$ for 16 h, and then concentrated in vacuo. The residue was partioned between ether and water. The ether phase was discarded, and the aqueous phase was treated with 1N HCl until the pH was 4. This acidic solution was extracted with EtOAc (3×). The combined EtOAc extracts were dried (MgSO$_4$) and concentrated in vacuo to give 4.36 g (96%) of 1-(2(S)-tert-butoxycarbonylamino-8-nonenoyl)-4(R)-hydroxy-pyrrolidine-2(S)-carboxylic acid as a white solid. This acid was then dissolved in 150 mL of DMF and (1R,2S)-1-amino-2-vinylcyclopropane carboxylic acid ethyl ester hydrochloride (2.61 g, 13.6 mmol), N-methyl morpholine (2.5 mL, 22.6 mmol), and HATU (5.2 g, 13.7 mmol) was added. The reaction mixture was stirred at rt under N$_2$ for 16 h, and then concentrated in vacuo. The residue was partitioned between ethyl acetate and pH 4 buffer (biphthalate). The organic phase was washed with sat. aq. NaHCO$_3$, dried (MgSO$_4$), and concentrated in vacuo to give the crude product. Flash chromatography (60%-80% ethyl acetate/hexane) gave 6.0 g (98%) of 1-{[1-(2-(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester as a white solid: $^1$H NMR (500 MHz, CD$_3$OD) δ 1.25 (t, J=7.2Hz, 3H), 1.33-1.80 (m, 10H), 1.46 (s, 9H), 2.09 (m, 3H), 2.25 (m, 2H), 3.76 (m, 2H), 4.14 (m, 2H), 4.27 (dd, J=8.5, 5.2 Hz, 1H), 4.50 (m, 2H), 4.94 (d, J=10.1Hz, 1H), 5.01 (dd, J=17.1, 1.8Hz, 1H), 5.11 (dd, J=10.4, 1.8Hz, 1H), 5.30 (d, J=15.6Hz, 1H), 5.80 (m, 2H), 8.57 (s, 1H); MS m/z 522 (M$^+$+1).

Step 3: Preparation of (1S,4R,6S,14S,18R)-7-cis-14-tert-butoxycarbonylamino-18-hydroxy-2,15-dioxo-3,16-diazatricyclo[14.3.0.0^{4,6}]nonadec-7-ene-4-carboxylic acid ethyl ester

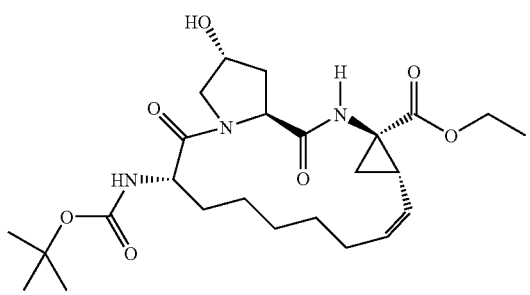

A solution of 1-{[1-(2(S)-tert-Butoxycarbonyl-amino-non-8-enoyl)-4(R)-hydroxy-pyrrolidine-2(S)carbonyl]-(1R)-amino}-2(S)-vinylcyclopropane-carboxylic acid ethyl ester (800 mg, 1.53 mmol) in 2 L of methylene chloride was flushed with $N_2$ for 0.5 h. Then tricyclohexylphosphine[1,3-bis(2,4,6-trimethyl-phenyl)-4,5-dihydroimidazol-2-ylidene][benzylidene]-ruthenium (IV) dichloride (Strem) (64 mg, 0.075 mmol) was added, and the mixture was flushed with $N_2$ for another 10 min. The light orange homogeneous solution was refluxed for 2 h to give a dark orange solution. The reaction mixture was cooled to rt and concentrated in vacuo to give an orange oil. Flash chromatography (ethyl acetate) gave 460 mg (61%) of (1S,4R,6S,14S,18R)-7-cis-14-tert-butoxycarbonylamino-18-hydroxy-2,15-dioxo-3,16-diazatricyclo[14.3.0.0^{4,6}]-nonadec-7-ene-4-carboxylic acid ethyl ester as a gray solid. $^1$H NMR (500 MHz, CDCl$_3$) δ 1.19 (t, J=7.2Hz, 3H), 1.42 (s, 9H), 1.22-1.8 (m, 8H), 1.87 (m, 2H), 2.03-2.22 (m, 4H), 2.63 (m, 1H), 3.65 (m, 1H), 4.09 (m, 3 H), 4.45 (m, 1H), 4.56 (s, 1H), 4.82 (m, 1H), 5.23 (m, 1H), 5.51 (s, 1H), 7.16 (s, 1 H); MS m/z 494 (M$^+$+1).

Step 4: (1S,4R,6S,14S,18R)-7-cis-14-tert-butoxycarbonylamino-18-hydroxy-2,15-dioxo-3,16-diazatricyclo[14.3.0.0^{4,6}]-nonadec-7-ene-4-carboxylic acid

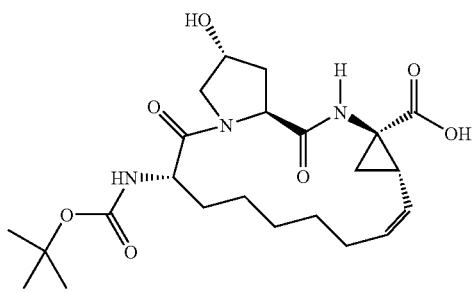

To a solution of (1S,4R,6S,14S,18R)-7-cis-14-tert-butoxycarbonylamino-18-hydroxy-2,15-dioxo-3,16-diazatricyclo[14.3.0.0^{4,6}]-nonadec-7-ene-4-carboxylic acid ethyl ester (493 mg, 1.0 mmol) in THF (4 mL), methanol (1 mL), and water (2 mL), was added powdered lithium hydroxide (480 mg, 20 mmol), and the light yellow slurry stirred at rt under $N_2$ for 16 h. The mixture was then concentrated in vacuo and the residue partioned between ether and water. The ether phase was discarded, and the aqueous phase was treated with 1 N HCl until pH 4. This acidic solution was extracted with EtOAc three times. The combined EtOAc extracts were dried (MgSO$_4$) and concentrated in vacuo to give 460 mg (98%) of Example 18, (1S,4R,6S,14S,18R)-7-cis-14-tert-butoxycarbonylamino-18-hydroxy-2,15-dioxo-3,16-diazatricyclo[14.3.0.0^{4,6}]-nonadec-7-ene-4-carboxylic acid as a gray solid. $^1$H NMR (500 MHz, CD$_3$OD) δ ppm 1.26 (t, J=7.2Hz, 3H), 1.35-1.52 (m, 15H), 1.57-1.68 (m, 3H), 1.79 (m, 1H), 2.04 (m, 1H), 2.16-2.41 (m, 3H), 3.80 (dd, J=10.7, 4.3 Hz, 1H), 3.88 (m, 1H), 4.38 (dd, J=8.9, 3.1Hz, 1H), 4.55 (m, 2H), 5.39 (t, J=9.8 Hz, 1H), 5.58 (m, 1H); MS m/z 466 (M$^+$+1).

Example 30

Preparation of (4-Cyclopropanesulfonylaminocarbonyl-18-hydroxy-2,15-dioxo-3,16-diaza-tricyclo[14.3.0.0^{4,6}]nonadec-7-en-14-yl)-carbamic acid tert-butyl ester

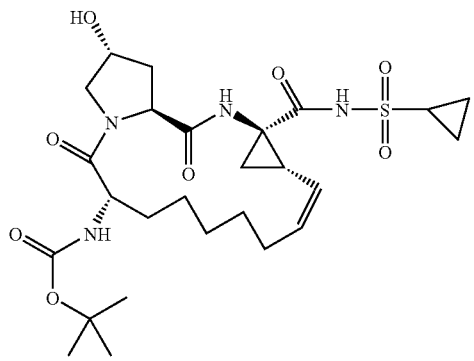

Example 30

Step 1: Preparation of 1-{[1-(2-tert-Butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester

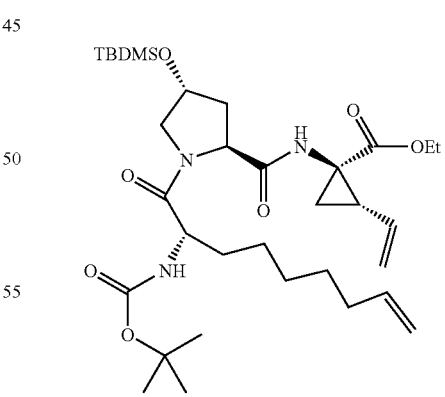

To a mixture of 1-{[1-(2(S)-tert-Butoxycarbonylamino-non-8-enoyl)-4(R)-hydroxy-pyrrolidine-2(S)carbonyl]-(1R)-amino}-2(S)-vinyl-cyclopropanecarboxylic acid ethyl ester (1.5 g, 2.87 mmoL) in 10 mL of DMF was added imidazole (0.25 g, 3.67 mmoL) and tert-butyl-dimethylsilyl chloride (516 mg, 3.44 mmoL). The mixture was stirred at rt for two days. The reaction mixture was then concentrated in vacuo, and the residue was dissolved in ethyl acetate. This solution was washed with water, dried over magnesium sulfate, and concentrated in vacuo to obtain a crude solid. Purification by flash chromatography (eluting with 20% ethyl acetate in hexane) gave 1.43 g (78%) of 1-{[1-(2-tert-butoxycarbonylamino-non-8-enoyl)-4-(tert-butyl-dimethyl-silanyloxy)-pyrrolidine-2-carbonyl]-amino}-2-vinylcyclopropanecarboxylic acid ethyl ester as a white solid.

$^1$H NMR (300 MHz, CD$_3$OD) δ 0.10 (s, 6H), 0.89 (s, 9H), 1.22 (m, 3H), 1.31-1.48 (m, 16H), 1.50-1.75 (m, 3H), 2.06 (m, 3H), 2.11-2.33 (m, 2H), 3.70 (m, 2H), 4.03-4.19 (m, 2H), 4.21 (m, 1H), 4.45 (t, J=7.87Hz, 1H), 4.59 (m, 1H), 4.91 (d, J=9.15 Hz, 1H), 4.98 (d, J=17.20Hz, 1H), 5.08 (dd, J=10.25, 1.83Hz, 1H), 5.27 (dd, J=17.38, 1.65Hz, 1H), 5.65-5.87 (m, 2H); MS m/z 636 (M$^+$+1).

Step 2: Preparation of 14-tert-Butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid, ethyl ester

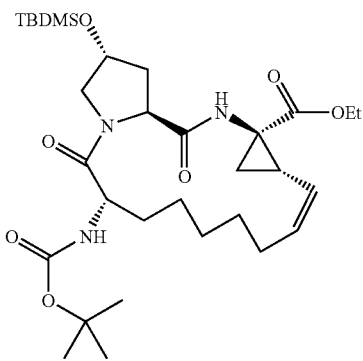

To a solution of 1-{[1-(2-tert-butoxycarbonylamino-non-8-enoyl)-4-(tert-butyl-dimethyl-silanyloxy)-pyrrolidine-2-carbonyl]-amino}-2-vinyl-cyclopropanecarboxylic acid ethyl ester (1.63 g, 2.56 mmoL) in 640 mL of methylene chloride was added 215 mg (0.26 mmoL) of tricyclohexylphosphine[1,3-bis(2,4,6-tri[benzylidene]ruthenium(IV) dichloride. The mixture was heated at reflux for 15 min. The residue was concentrated in vacuo, and then purified by flash chromatography eluting with 30% ethyl acetate/hexane. To further decolorize the sample, the crude product was chromatographed a second time eluting with 50% ether in hexane to give 1.5 g (96%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid ethyl ester as a white solid. $^1$H NMR (500 MHz, CD$_3$Cl) δ 0.06 (s, 3 H), 0.07 (s, 3H), 0.86 (s, 9H), 1.18-1.24 (m, 6H), 1.34-1.64 (m, 14H), 1.86-1.96 (m, 3H), 2.02-2.09 (m, 1H), 2.11-2.17 (m, 1H), 2.19-2.28 (m, 1H), 2.57-2.63 (m, 1H), 3.50-3.54 (m, 1H), 3.71 (dd, J=10.22, 6.26Hz, 1H), 4.06-4.17 (m, 2H), 4.52-4.58 (m, 2H), 4.75 (d, J=8.55Hz, 1H), 5.21 (t, J=9.92Hz, 1H), 5.35 (d, J=7.63Hz, 1H), 5.45-5.50 (m, 1H), 6.94 (s, 1H); MS m/z 608 (M$^+$+1).

Step 3: Preparation of 14-tert-butoxycarbonylamino-18-(tert-butyl-dimethyl-silanyloxy)-2,15-dioxo-3,16-diaza-tricyclo[14.3.0.0$^{4,6}$]nonadec-17-ene-4-carboxylic acid

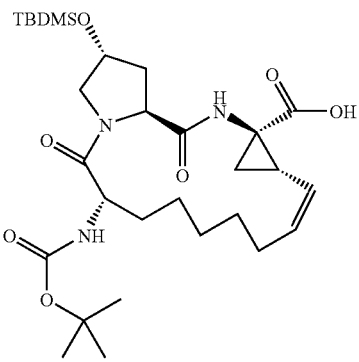

To a solution of 14-tert-butoxycarbonylamino-18-(tert-butyl-dimethyl-silanyloxy)-2,15-dioxo-3,16-diaza-tricyclo [14.3.0.0$^{4,6}$]nonadec-7-ene-4-carboxylic acid ethyl ester (1.5 g, 2.47 mmoL) in a mixed solvent system of THF (4 mL), methanol (1 mL), and water (2 mL), was added powdered lithium hydroxide monohydrate (1.0 g, 50 mmoL). The light yellow slurry was stirred at rt under N$_2$ for 4 h. The mixture was then concentrated in vacuo, and the residue partioned between ether and water. The ether phase was discarded, and the aqueous phase was treated with 1 N HCl until reaching pH 4. This acidic solution was extracted with EtOAc (3×). The combined EtOAc extracts were dried (MgSO$_4$), and concentrated in vacuo to give 1.2 g (84%) of 14-tert-butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid as an off-white solid. $^1$H NMR (300 MHz, CD$_3$OD) 0.12 (s, 6H), 0.89 (s, 9H), 1.23-1.64 (m, 17H), 1.70-1.87 (m, 1H), 1.90-2.49 (m, 6H), 3.70-3.80 (m, 1H), 3.83-3.90 (m, 1H), 4.28-4.36 (m, 1H), 4.47-4.55 (m, 1H), 4.65 (s, 1H), 5.30-5.39 (m, 1H), 5.53-5.62 (m, 1H); MS m/z 580 (M$^+$+1).

Step 4: Preparation of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester

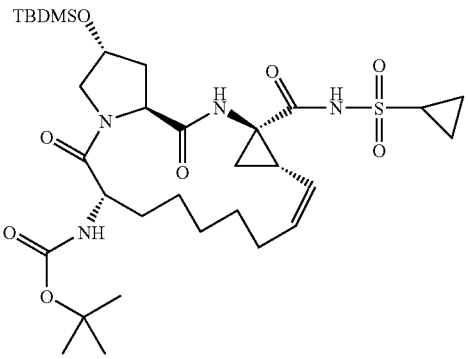

14-tert-Butoxycarbonylamino-18-(tert-butyl-dimethyl-silanyloxy)-2,15-dioxo-3,16-diaza-tricyclo[14.3.0.0$^{4,6}$]nonadec-7-ene-4-carboxylic acid (500 mg, 0.86 mmoL) was dissolved in 25 mL of THF and treated with CDI (180 mg, 1.12 mmoL). (Care was taken to avoid moisture by using oven dried glassware and maintaining a dry N2 atmosphere). After refluxing the reaction mixture for 2 h, it was cooled to rt and treated sequentially with cyclopropylsulfonamide (135 mg, 1.12 mmoL) and DBU (170 mg, 1.12 mmoL). The reaction mixture was stirred for 4 h at rt, and the THF was removed by rotary evaporation. The residue was partitioned between ethyl acetate and pH 4 buffer. The organic phase was dried (MgSO4) and concentrated in vacuo to give the crude product. It was then purified by flash chromatography (eluting with 33% ethyl acetate in hexane) to give 300 mg (51%) of [18-(tert-butyl-dimethyl-silanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester as a white solid. $^1$H NMR (300 MHz, CD$_3$OD) δ 1H 0.07 (s, 3H), 0.08 (s, 3H), 0.85 (s, 9H), 0.87-1.49 (m, 21H), 1.73-1.95 (m, 3H), 2.08-2.16 (m, 1H), 2.25-2.36 (m, 2H), 2.42-2.56 (m, 1H), 2.85-2.93 (m, 1H), 3.65-3.74 (dd, J=10.61, 3.66Hz, 1H), 3.89 (d, J=10.25Hz, 1H), 4.34 (m, J=9.70, 9.70Hz, 1H), 4.43 (t, J=7.87Hz, 1H), 4.57 (s, 1H), 4.94-5.01 (m, 1H), 5.10 (d, J=8.78Hz, 1H), 5.66-5.75 (m, 1H), 6.55 (s, 1 H), 10.13 (s, 1H); MS m/z 683 (M$^+$+1).

Step 5: Preparation of Example 19, (4-Cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester

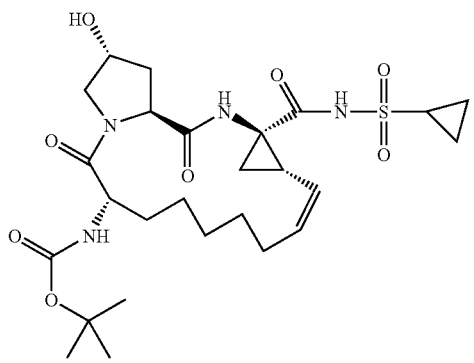

Example 30

To a mixture of [18-(tert-butyl-dimethylsilanyloxy)-4-cyclopropanesulfonylaminocarbonyl-2,15-dioxo-3,16-diaza-tricyclo[14.3.0.0$^{4,6}$]nonadec-7-en-14-yl]-carbamic acid tert-butyl ester (330 mg, 0.48 mmoL) in 25 mL of THF was added tetrabutylammonium floride (150 mg, 0.54 mmoL). The reaction mixture was stirred at rt for 18 h, and then the THF was removed by rotary evaporation. The residue was partitioned between ethyl acetate and water. The organic phase was dried (MgSO$_4$) and concentrated in vacuo to give the crude product. It was then purified by triturating with hexane to yield 200 mg (73%) of (4-cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester, Example 19, as a white solid. $^1$H NMR (500 MHz, CD$_3$Cl) δ 1.87-1.64 (m, 21H), 1.70-1.98 (m, 3 H), 2.15-2.56 (m, 5H), 2.85-2.94 (m, 1H), 3.71 (d, J=13.91Hz, 1H), 4.10-4.26 (m, 2H), 4.51 (t, J=7.87Hz, 1H), 4.62 (s, 1H), 4.98 (m, 1H), 5.06 (d, J=8.78Hz, 1H), 5.64-5.71 (m, 1H), 6.72 (s, 1H), 10.24 (s, 1H); MS m/z 569 (M$^+$+1).

The following macrocyclic alcohol intermediates were prepared employing the procedures described in examples 29 and 30:

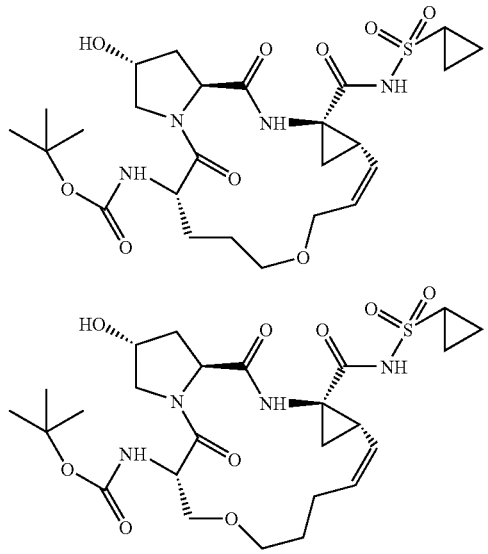

The following macrocyclic alcohol intermediates could be prepared employing the procedures described in examples 29 and 30:

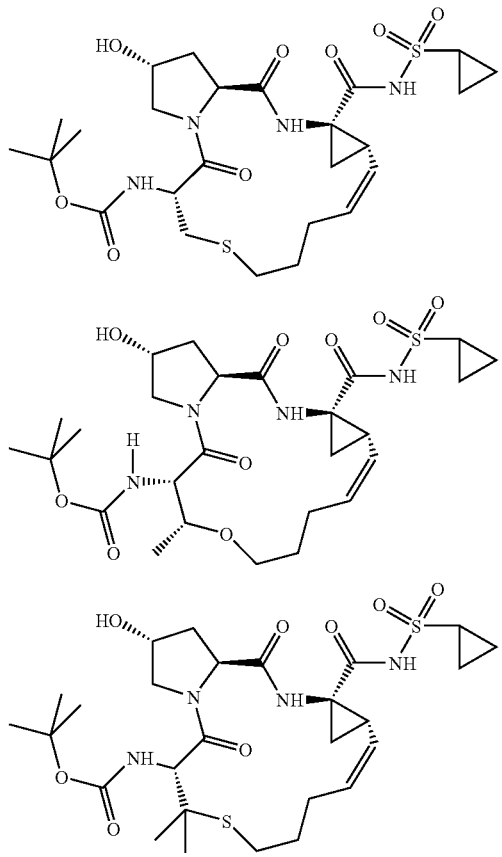

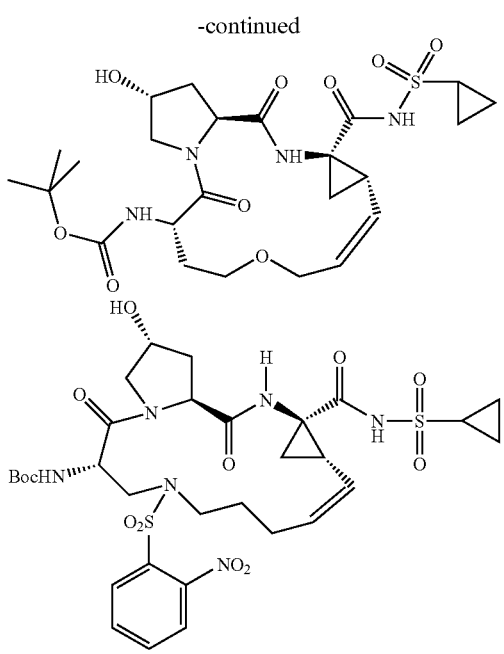

Example 31

Preparation of Example 31, 2(S)-tert-butoxycarbonylamino-3-pent-4-enylsulfanylpropionic acid

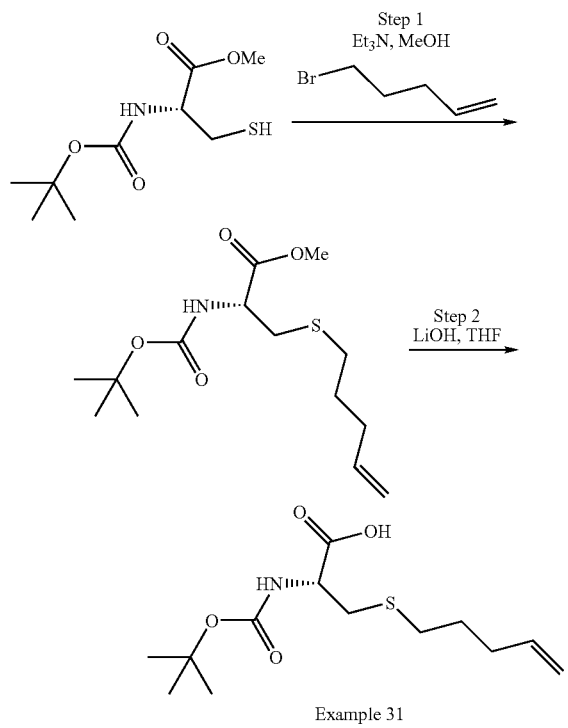

Example 31

Step 1: To a solution of N-Boc-cysteine methyl ester (3.36 g, 0.014 mol) in methanol (166 mL) at RT was added triethylamine (10.8 mL) and 1-bromopent-4-ene (3.19 g, 21 mmol, 1.5 equivalents) and the resulting solution was stirred at room temperature overnight. The mixture was then concentrated in vacuo and the resulting residual mixture was purified using flash chromatography (hexane, ethyl acetate gradient) to provide 1.76 g (41%) of the desired thioether. $^1$H NMR (500 MHz, CDCl$_3$) δ 1.43 (s, 9H), 1.64 (m, 2H), 2.11 (m, 2H), 2.51 (m, 2H), 2.95 (m, 2H), 3.75 (s, 3H), 4.51 (m, 1H), 4.95-5.03 (m, 2H), 5.34 (m, 1H), 5.80 (1H, m); MS m/z 304(M$^+$+1).

Step 2: The thioether product of step 1 (9.51 g, 31.4 mmol) was added to a mixture of 1M LiOH in water (200 mL) and THF (200 mL) and the resulting mixture was stirred at room temperature overnight. The reaction mixture was then acidified using 1N hydrochloric acid and the resulting mixture was extracted several times with ethyl acetate. The extracts were combined, dried over magnesium sulfate, and concentrated in vacuo to provide the desired acid, Example 20, which was used as is in the next reaction.

Example 32

Preparation of Example 32, N-tert-Butoxycarbonyl-3-(4-pentenylthio)-L-valine

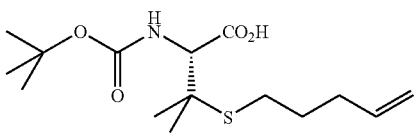

Example 32

Step 1: Preparation of N-tert-butoxycarbonyl-3-(4-pentenylthio)-L-valine, methyl ester

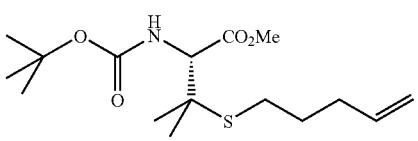

To a solution of 7.12 g (48 mmol, 1.0 eq) of L-penicillamine in 100 mL of 1,4-dioxane and 25 mL of water at room temperature was added 9.60 mL (96 mmol, 2.0 eq) of 10N aqueous sodium hydroxide solution, followed by the dropwise addition of 12.00 mL (101 mmol, 2.1 eq) of 5-bromo-1-pentene over several minutes. The resulting mixture was stirred at room temperature for 68 hours. At this point 12.50 g (57 mmol, 1.2 eq) of di-tert-butyl dicarbonate was added, and the mixture was stirred at room temperature for another 6 hours. The mixture was concentrated under vacuum, and the residue was dissolved in water. The aqueous mixture was washed with diethyl ether, adjusted to pH 3 employing 1N hydrochloric acid, and then extracted with ethyl acetate. The combined extracts were washed with brine, dried over anhydrous magnesium sulfate, filtered, and concentrated under vacuum.

The crude product (12.20 g) was dissolved in 120 mL of anhydrous dimethylsulfoxide. To this solution was added 10.50 g (76 mmol) of potassium carbonate and 4.70 mL (76 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2-10% ethyl acetate/hexane) provided 8.54 g of N-tert-butoxycarbonyl-3-(4-pentenylthio)-L-valine, methyl ester as a colorless oil. NMR (300 MHz, CDCl$_3$): δ 5.76 (d of d of t, 1 H, J=17.2, 10.3, 6.6Hz), 5.35 (br d, 1H, J=9.0Hz), 5.05-4.94 (m, 2H), 4.27 (br d, 1H, J=9.0Hz), 3.73 (s, 3H), 2.52 (m, 2H), 2.13 (quart., 2H, J=7.3Hz), 1.61 (quint., 2H, J=7.3Hz), 1.43 (s, 9H), 1.35 (s, 3H), 1.33 (s, 3H).

Step 2: Preparation of Example 32, N-tert-Butoxycarbonyl-3-(4-pentenylthio)-L-valine

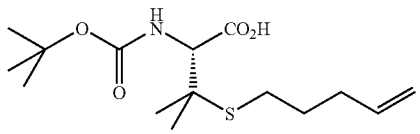

Example 32

To a solution of 8.52 g (25.7 mmol) of N-tert-butoxycarbonyl-3-(4-pentenylthio)-L-valine, methyl ester in 200 mL of tetrahydrofuran at room temperature was added a solution of 1.10 g (26.2 mmol) of lithium hydroxide monohydrate in 50 mL of water. The resulting mixture was stirred at room temperature for 65 hours. To the reaction mixture then was added 28 mL of 1.00N hydrochloric acid. The mixture was diluted with diethyl ether, washed with water (3×) and brine, dried over anhydrous sodium sulfate, filtered, and concentrated under vacuum to afford 8.10 g of N-tert-butoxycarbonyl-3-(4-pentenylthio)-L-valine as a colorless oil. NMR (300 MHz, CDCl$_3$): δ 5.75 (d of d of t, 1H, J=17.2, 10.3, 6.6 Hz), 5.40 (br s, 1H), 5.05-4.94 (m, 2H), 4.28 (br s, 1H), 2.56 (m, 2H), 2.13 (quart., 2H, J=7.3Hz), 1.63 (quint., 2H, J=7.3Hz), 1.44 (s, 9H), 1.39 (s, 3H), 3 H).

Example 33

Preparation of Example 33, 5-Allyloxy-2(S)-(tert-butoxycarbonylamino)pentanoic acid

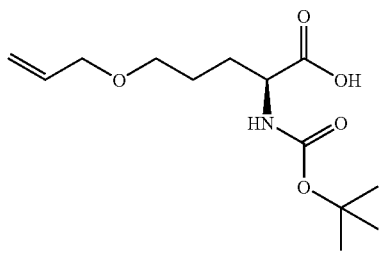

Example 33

Step 1: Preparation of Isopropyl pyrrolidin-5-one-2(S)-carboxylate

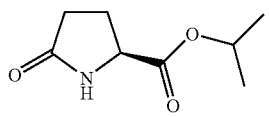

A solution of L-pyroglutamic acid (Aldrich, 25.0 g, 195 mmol) and para-toluenesulfonic acid mono hydrate (3.71 g, 19.5 mmol) was refluxed in isopropanol (40 mL) under nitrogen for 6 hours using a Dean-Stark trap variation (condensate returned through a Soxhlet extractor filled with 4 Å molecular sieves). After cooling to room temperature, the reaction was diluted with ether, washed with saturated aqueous sodium bicarbonate and then saturated aqueous NaCl, dried (MgSO$_4$) and evaporated to give a colorless syrup. It crystallized upon setting. Triturating the crystalline residue in hexane provided 31.9 g (96%) of isopropyl pyrrolidin-5-one-2(S)-carboxylate as white prisms: $^1$H NMR (300 MHz, Chloroform-D) δ 6.35 (br s, 1 H), 5.04 (sept. 1H, J=6.2Hz), 4.18 (dd, 1H, J=8.4, 5.3Hz), 2.51-2.28 (m, 3H), 2.27-2.12 (m, 1H), 1.24 (d, 6H, J=6.2Hz). LCMS m/z 172 (M+H)$^+$.

Step 2: Preparation of Isopropyl 1-(tert-butoxycarbonyl)-pyrrolidin-5-one-2(S)-carboxylate

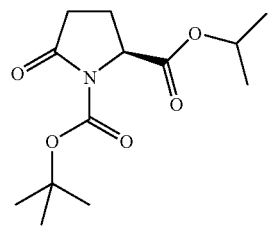

A solution of isopropyl pyrrolidin-5-one-2(S)-carboxylate (product of step 26A, 31.9 g, 188 mmol), di-tert-butyl dicarbonate (48.6 g, 225 mmol) and DMAP (2.30 g, 8.8 mmol) in acetonitrile (300 mL) was stirred at room temperature under N$_2$ for 30 minutes. The reaction was evaporated to about 100 mL, diluted with ether, washed with 1N HCl then saturated aqueous NaCl, dried (MgSO$_4$) and evaporated to give isopropyl 1-(tert-butoxycarbonyl)pyrrolidin-5-one-2(S) carboxylate as a light yellow oil, 50.1 g (99%): $^1$H NMR (300 MHz, Chloroform-D) δ 5.06 (sept. 1H, J=6.2Hz), 4.53 (dd, 1H, J=9.5, 2.9Hz), 2.66-2.40 (m, 2H), 2.36-2.22 (m, 1H), 2.03-1.93 (m, 1H), 1.47 (s, 9H), 1.26 (d, 3H, J=6.2Hz), 1.24 (d, 3H, J=6.2Hz). LCMS m/z 272 (M+H)$^+$.

Step 3: Preparation of Isopropyl 2(S)-(tert-butoxycarbonylamino)-5-hydroxypentanoate

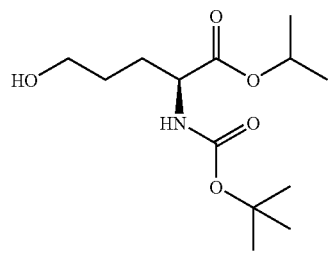

To a solution of isopropyl 1-(tert-butoxycarbonyl)pyrrolidin-5-one-2(S)-carboxylate (product of step 26B, 49.5 g, 183 mmol) in methanol (300 mL) was added sodium borohydride (10.0 g, 263 mmol) in ~1 g portions over 1.5 hours. The reaction was stirred under nitrogen for another 10 minutes. It was diluted with water, extracted with ether, combined organic fractions washed with saturated aqueous NaCl, dried (MgSO$_4$) and evaporated to give a light yellow oil. Flash chromatography (silica gel, 20-30% ethyl acetate/hexane) gave 31.8 g (64%) of isopropyl 2(S)-(tert-butoxycarbonylamino)-5-hydroxypentanoate as a colorless syrup: $^1$H NMR (300 MHz, Chloroform-D) δ 5.16 (br d, 1H, J=7.3Hz), 5.03

(sept., 1H, J=6.2Hz), 4.28 (br d, 1H, J=6.2Hz), 3.67 (br dd, J=10.2, 5.5Hz), 1.94-1.79 (m, 2H), 1.76-1.67 (m, 1H), 1.66-1.56 (m, 2H), 1.43 (s, 9H), 1.25 (d, 3H, J=6.2Hz), 1.23 (d, 3H, J=6.2Hz). LCMS m/z 276 (M+H)+.

Step 4: Preparation of Isopropyl-5-allyloxy-2(S)-(tert-butoxycarbonylamino)pentanoate

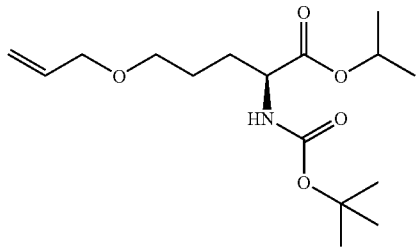

A degassed mixture of isopropyl 2(S)-(tert-butoxycarbonylamino)-5-hydroxypentanoate (product of step 26C, 17.6 g, 63.9 mmol), allyl methyl carbonate (24.0 ml, 213 mmol), Pd$_2$(dba)$_3$ (1.62 g, 1.78 mmol) and BINAP (4.42 g, 7.10 mmol) in THF (150 mL) was refluxed under nitrogen for 3 hours. After cooling to room temperature, the reaction was diluted with ether, filtered through celite and evaporated giving a dark brown syrup. Flash chromatography of the residue (silica gel, 30% ether/hexane) gave isopropyl 5-allyloxy-2 (S)-(tert-butoxycarbonylamino)pentanoate as a viscous colorless oil, 16.3 g (81%): $^1$H NMR (300 MHz, Chloroform-D) δ 5.88 (ddt, 1H, 17.4, 10.4, 5.5), 5.28 (m, 1H), 5.22-5.11 (m, 1H), 5.02 (sept., 1H, J=6.2Hz), 4.21 (br t, 1H, J=6.7Hz), 3.94 (dt, 2H, J=5.9, 1.5Hz), 3.42 (t, 2H, J=5.9Hz), 1.90-1.82 (m, 1H), 1.75-1.57 (m, 3H), 1.42 (s, 9H), 1.21 (d, 3H, J=6.2Hz), 1.19 (d, 3H, J=6.2Hz). LCMS m/z 316 (M+H)+.

Step 5: Preparation of Example 33, 5-Allyloxy-2(S)-(tert-butoxycarbonylamino)pentanoic acid

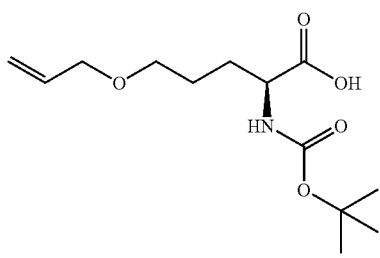

Example 33

A mixture of isopropyl 5-allyloxy-2(S)-(tert-butoxycarbonylamino)pentanoate (product of step 26D, 16.1 g, 51.1 mmol) and lithium hydroxide hydrate (4.19 g, 102 mmol) in THF/water (100 mL/20 mL) was stirred at room temperature under nitrogen for 16 hours. The reaction was diluted with water, washed with ether, pH of aqueous fraction adjusted to ~4, extracted with ether, combined organic fractions washed with saturated NaCl, dried (MgSO$_4$) and evaporated giving 5-allyloxy-2(S)-(tert-butoxycarbonylamino)pentanoic acid as a light yellow syrup: $^1$H NMR (300 MHz, Chloroform-D) δ 5.89 (ddt, 1H, J=17.4, 10.4, 5.5), 5.25 (dd, 1H, J=17.4, 1.6Hz), 5.17 (dd, 1H, J=10.4, 1.6Hz), 4.30 (br d, 1H, J=6.2), 3.96 (dt, 2H, J=5.9, 1.5Hz), 3.46 (t, 2H, J=5.9Hz), 1.96-1.86 (m, 1H), 1.85-1.77 (m, 1H), 1.75-1.64 (m, 2H), 1.43 (s, 9H). LCMS m/z 274 (M+H)+.

Example 34

General Procedure for the Preparation of Example 34

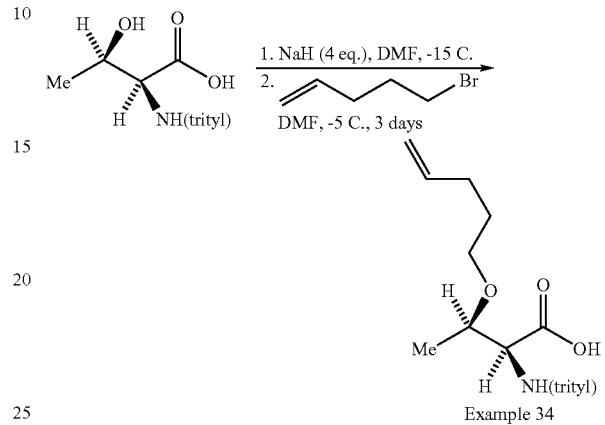

Example 34

Example 34

Example 23 was prepared by adding a DMF solution of N-trityl protected threonine to a DMF solution of sodium hydride cooled to −15 C. The reaction mixture was stirred for 30 minutes at −15 C after which 5-bromo-1-pentene was added and the resulting mixture was warmed to −5 C. The reaction mixture was maintained at −5 C for 3 days after which time the reaction was quenched by the addition of 1N aqueous HCl and worked up using standard extraction procedures as described above. Example 23 was obtained in pure form by standard chromatography procedures.

Example 35

Preparation of Example 35, N-tert-Butoxycarbonyl-O-(4-pentenyl)-L-serine

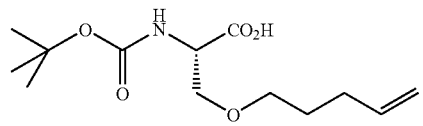

Example 35

Step 1: Preparation of N-tert-Butoxycarbonyl-O-(4-pentenyl)-L-serine, methyl ester

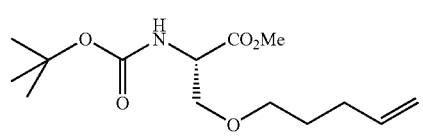

To a solution of 10.26 g (50 mmol, 1.0 eq) of N-tert-butoxycarbonyl-L-serine in 500 mL of anhydrous dimethyl-sulfoxide at room temperature was added 2.00 g (50 mmol, 1.0 eq) of 60% sodium hydride in mineral oil. This mixture was stirred at room temperature for 0.5 hour until the evolution of gas had ceased. To the resulting solution was added 6.00 mL (50 mmol, 1.0 eq) of 5-bromo-1-pentene followed immediately by another 2.00 g (50 mmol, 1.0 eq) of 60% sodium hydride in mineral oil. The reaction mixture then was stirred at room temperature for 16 hours. The mixture was diluted with 2000 mL of water, adjusted to pH 3-4 by the addition of 50 mL of 1.00N hydrochloric acid, and extracted with ethyl acetate. The organic phase was washed with water (2×) and brine, dried over anhydrous sodium sulfate, filtered, and concentrated under vacuum. To remove the residual mineral oil the resulting material was dissolved in a dilute aqueous sodium hydroxide solution. This aqueous solution was washed with hexane and then adjusted to pH 4 employing hydrochloric acid, and extracted with ethyl acetate. The extract was washed with water (2×) and brine, dried over anhydrous sodium sulfate, filtered, and concentrated under vacuum.

The crude product (7.70 g) was dissolved in 100 mL of anhydrous dimethylsulfoxide. To this solution was added 7.80 g (56 mmol) of potassium carbonate and 3.50 mL (56 mmol) of iodomethane, and the resulting mixture was stirred at room temperature for 24 hours. The reaction mixture was diluted with water and extracted with ethyl acetate. The combined extracts were washed with water (2×) and brine, dried over anhydrous sodium sulfate, filtered, and concentrated under vacuum. Column chromatography on silica gel (elution: 2-10% ethyl acetate/hexane) provided 6.70 g of N-tert-butoxycarbonyl-O-(4-pentenyl)-L-serine, methyl ester as a colorless oil. NMR (300 MHz, CDCl$_3$): δ 5.78 (d of d of t, 1H, J=17.2, 10.2, 6.6Hz), 5.34 (br d, 1H, J=8.0Hz), 5.03-4.92 (m, 2H), 4.40 (m, 1H), 3.81 (d of d, 1H, J=9.5, 2.9Hz), 3.74 (s, 3H), 3.61 (d of d, 1H, J=9.5, 3.5Hz), 3.42 (m, 2H), 2.06 (quart., 2H, J=7.3Hz), 1.61 (quint., 2H, J=7.3Hz), 1.44 (s, 9 H).

Step 2: Preparation of Example 35, N-tert-Butoxycarbonyl-O-(4-pentenyl)-L-serine

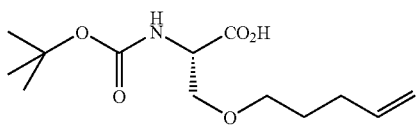

Example 35

To a solution of 6.65 g (23 mmol) of N-tert-butoxycarbonyl-O-(4-pentenyl)-L-serine, methyl ester in 500 mL of tetrahydrofuran at room temperature was added a solution of 1.95 g (46 mmol) of lithium hydroxide monohydrate in 100 mL of water. The resulting mixture was stirred at room temperature for 40 hours. To the reaction mixture then was added 46mL of 1.00N hydrochloric acid. The mixture was diluted with ethyl acetate, washed with water (3×) and brine, dried over anhydrous sodium sulfate, filtered, and concentrated under vacuum to afford 6.30 g of N-tert-butoxycarbonyl-O-(4-pentenyl)-L-serine as a colorless oil. NMR (300 MHz, CDCl$_3$): δ 5.77 (d of d of t, 1H, J=17.2, 10.2, 6.6Hz), 5.37 (br d, 1H, J=8.0Hz), 5.03-4.92 (m, 2H), 4.42 (m, 1H), 3.87 (d of d, 1H, J=9.5, 2.6Hz), 3.63 (d of d, 1 H, J=9.5, 4.0Hz), 3.45 (t, 2H, J=6.6Hz), 2.07 (quart., 2H, J=7.3Hz), 1.64 (quint., 2H, J=7.3Hz), 1.44 (s, 9H).

Example 36

Preparation of Example 36, (S)-4-allyloxy-2-(tert-butoxycarbonylamino)butyric acid

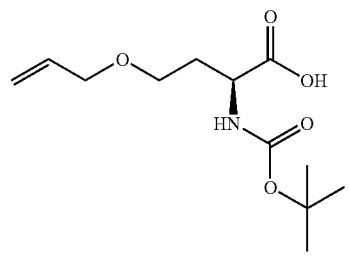

Example 36

To a mixture of sodium hydride (913 mg, 22.8 mmoL) in DMF at 0° C. was added N-t-Boc-L-homoserine (2 g, 9.13 mmoL). This reaction mixture was stirred at 0° C. for 15 min, and then allyl bromide (1.38 g, 11.4 mmoL) was added. The mixture was warmed up to rt, and stirred for 2 h. It was then concentrated in vacuo. The residue was diluted with water, and sequentially washed with hexane and ether. The organic layers were discarded, and the aqueous layer was carefully adjusted to pH 3 with 1 N HCl. This acidic aqueous solution was extracted with ethyl acetate. The organic phase was dried (MgSO$_4$), and concentrated in vacuo to yield 2.2 g (93%) of (S)-4-allyloxy-2-(tert-butoxycarbonylamino)butyric acid as a colorless oil. $^1$H NMR (300 MHz, CD$_3$OD) δ 1.42 (s, 9H), 1.80-1.90 (m, 1H), 2.04-2.16 (m, 1H), 3.50-3.54 (m, 2H), 3.97 (d, J=4.39Hz, 2H), 4.23 (dd, J=8.78, 4.39Hz, 1H), 5.15 (d, J=10.25Hz, 1H), 5.26 (dd, J=17.38, 1.65Hz, 1H), 5.84-5.97 (m, 1H).

Example 37

Preparation of Example 37, (S)-2-(tert-butoxycarbonyl)-3-(2-nitro-N-(pent-4-enyl)phenylsulfonamido)propanoic acid

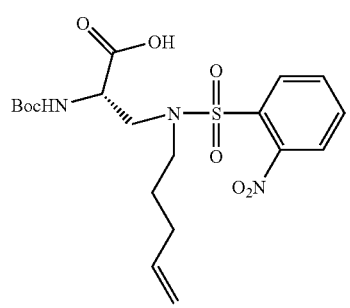

Example 37

Step 1: Preparation of methyl 3-amino-2(S)-(tert-butoxycarbonylamino)propanoate

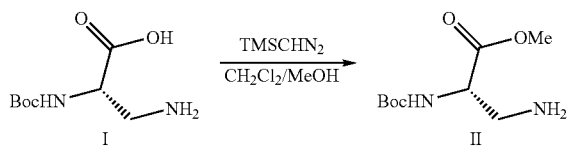

To a mixture of i (Boc-DAP-OH)(3.0 g 14.7 mmol) in 50 mL of methylene chloride was added 5 mL of methanol. To this solution was slowly added (trimethylsilyl)diazomethane (2 M in ether, 7.9 mL, 15.8 mmoL). The mixture was stirred at rt for 2 h until all of the solid dissolved and the solution turned light yellow. It was then concentrated to yield 3.2 g (99%) of methyl 3-amino-2(S)-(tert-butoxycarbonylamino) propanoate ii as a colorless oil. $^1$H NMR (CD$_3$OD, 300 MHz) δ 1.46 (s, 9H), 2.82-3.00 (m, 2H), 3.71 (s, 3H), 4.14 (brs, 1H).

Preparation of methyl 2(S)-(tert-butoxycarbonylamino)-3-(2-nitrophenylsulfonamido)propanoate iii

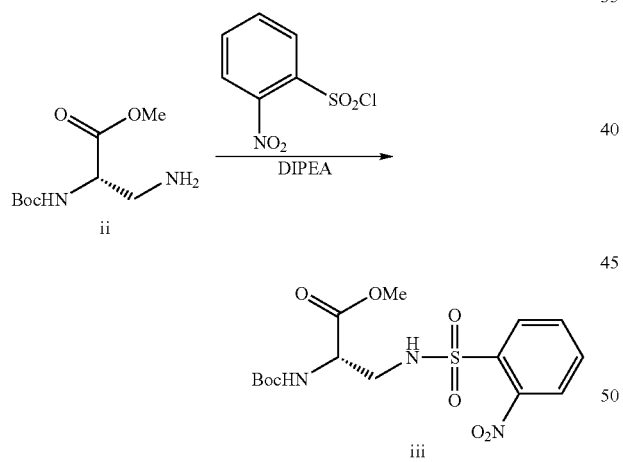

To a mixture of methyl 3-amino-2(S)-(tert-butoxycarbonylamino)propanoate ii (1.6 g, 7.3 mmoL) in DCM (50 mL) was added DIPEA (1.64 mL, 9.4 mmoL) and 2-nitrobenzene sulfonyl chloride (1.62 g, 7.3 mmoL). The mixture was stirred at rt for 2 h. It was then concentrated, dissolved in ethyl acetate, which was then washed with sat. sodium bicarbonate, brine and dried over magnesium sulfate. It was then filtered, concentrated to yield 2.9 g (98%) of methyl 2(S)-(tert-butoxycarbonylamino)-3-(2-nitrophenylsulfonamido)propanoate iii as a yellow foam. $^1$H NMR (CD$_3$OD, 300 MHz) δ 1.41 (s, 9H), 3.36-3.51 (m, 2H), 3.71 (s, 3H), 4.22 (m, 1H), 7.80-7.90 (m, 3H), 8.07-8.10 (m, 1H).

Preparation of methyl 2(S)-(tert-butoxycarbonylamino)-3-(2-nitro-N-(pent-4-enyl)phenylsulfonamido)propanoate iv

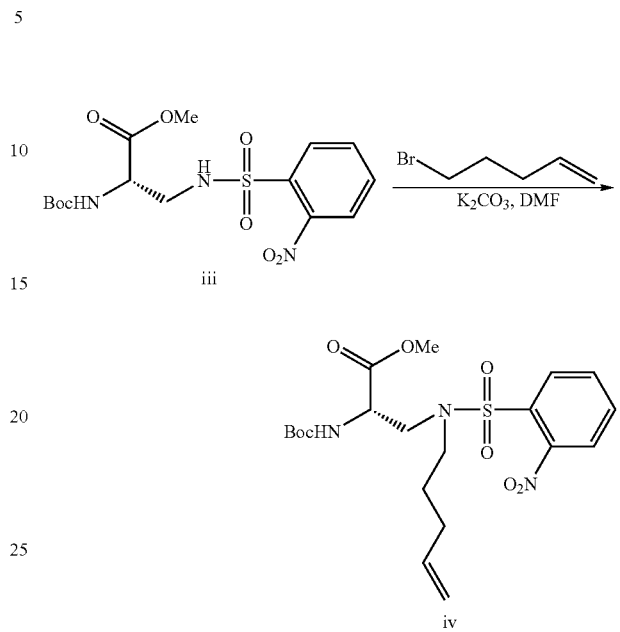

To a mixture of methyl 2(S)-(tert-butoxycarbonylamino)-3-(2-nitrophenylsulfonamido)propanoate iii (150 mg, 0.37 mmol) in 3 mL of DMF was added potassium carbonate (102 mg, 0.74 mmoL). This mixture was stirred at rt for 20 min followed by the addition of 5-bromo-1-pentene (65 μL, 0.55 mmoL). The reaction mixture was stirred at rt for 2 days. It was then filtered, concentrated and purified by silica gel chromatography (eluting with 25% ethyl acetate in hexane) to give 75 mg (43%) of methyl 2(S)-(tert-butoxycarbonylamnio)-3-(2-nitro-N-(pent-4-enyl)phenylsulfonamido)propanoate iv as a yellow solid. $^1$H NMR (CD$_3$OD, 300 MHz) δ 1.42 (s, 9H), 1.54-1.64 (m, 2H), 1.97 (q, J=7.20Hz, 2H), 3.37 (m, 2H), 3.57-3.80 (m, 2H), 3.72 (s, 3H), 4.42 (dd, J=8.60, 5.31Hz, 1H), 4.91-5.01 (m, 2H), 5.69-5.79 (m, 1H), 7.75-7.85 (m, 3H), 8.04 (m, 1H); MS m/z 372 (M$^+$+1-Boc).

Preparation of Example 37, 2(S)-(tert-butoxycarbonylamino)-3-(2-nitro-N-(pent-4-enyl)phenylsulfonamido)propanoic acid v

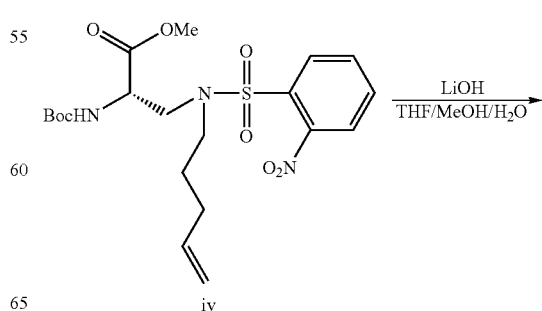

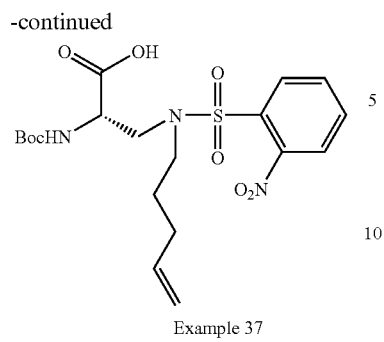

Example 37

(S)-methyl 2-(tert-butoxycarbonyl)-3-(2-nitro-N-(pent-4-enyl)phenylsulfonamido)-propanoate iv (500 mg, 1.06 mmol) was dissolved in the mixed solvent system: THF (4 mL), methanol (1 mL), and water (2 mL). Powdered lithium hydroxide (250 mg, 10.4 mmol) was added. The light yellow slurry was stirred at rt for 15 h, and then concentrated in vacuo. The residue was partitioned between ether and water. The ether phase was discarded, and the aqueous phase was treated with 1 N HCl until the pH was 4. This acidic solution was extracted with ethyl acetate four times. The combined ethyl acetate extracts were dried ($MgSO_4$) and concentrated in vacuo to give 430 mg (89%) of 2-(tert-butoxycarbonylamino)-3-(2-nitro-N-(pent-4-enyl)phenylsulfonamido)propanoic acid (Example 26) as a yellow oil. $^1$H NMR ($CD_3OD$, 300 MHz) δ 1.38 (s, 9H), 1.51-1.60 (m, 2H), 1.89-1.98 (m, 2H), 3.28-3.32 (m, 2H), 3.59-3.64 (dd, J=14.95, 9.46Hz, 1H), 3.71-3.74 (m, 1H), 4.33 (dd, J=9.61, 4.43Hz, 1H), 4.87-4.94 (m, 2H), 5.63-5.72 (m, 1H), 7.71-7.77 (m, 3H), 8.01 (dd, J=7.48, 1.37Hz, 1H); MS m/z 358 ($M^+$+1-Boc).

Example 38

In the examples that follow there are four general procedures, referred to as Methods I-V, which are employed in the synthesis of compounds of the present invention. Method I is described in Example 38. Method II is described in Example 56. Method III is described in Example 73. Method IV is described in Example 82. Method V is described in Example 87.

Preparation of Compound 1

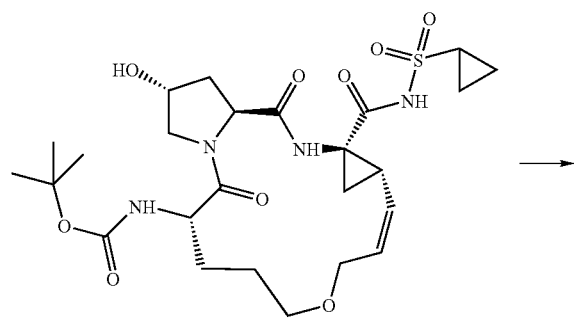

→

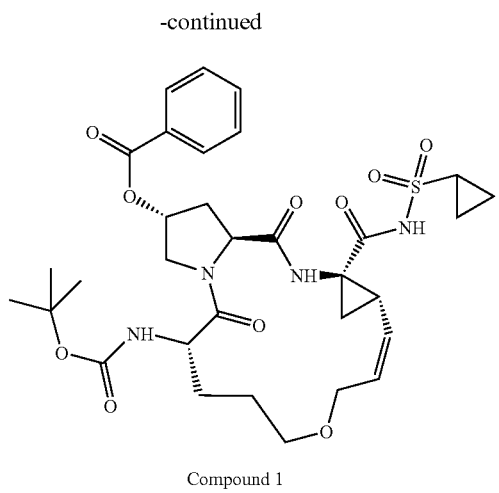

Compound 1

Method I: Method I is one of four general procedures referred to herein in the synthesis of compounds of the present invention.

Method I: The intermediate 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) was dissolved in 2 mL of pyridine and treated with benzoyl chloride (61 μL, 0.53 mmol). Care was taken to avoid moisture by using oven-dried glassware and maintaining a dry $N_2$ atmosphere above the reaction. The progression of the reaction was checked by LCMS. After stirring the reaction solution for 5 hours, it was diluted with diethyl ether. The solution washed with aqueous 1N HCl and then brine. The organic phase was dried ($MgSO_4$), decanted (to remove from the drying agent), and concentrated in vacuo to give the crude product. Chromatography of the residue ($C_{18}$, 40-80% methanol/water), upon combining and evaporating the appropriate fractions, gave the desired product at 90% purity (HPLC). Flash chromatography of the refined residue (silica gel, 20% hexane/ethyl acetate with 0.1% acetic acid), upon combining and concentrating the appropriate fractions, gave the desired product at 98.7% purity. The residue was triturated with diethyl ether/hexane to provide 31 mg (26%) of the desired product, 18-benzoyloxy-14-tert-butoxycarbonylamino-4-cyclopropylsulfonylaminocarbonyl-2,15-dioxo-3,16-diaza-10-oxatricyclo[14.3.0.0$^{4,6}$]nonadec-7-ene as a white powder: 99.3% pure (HPLC), MS m/z 673.2 (M−H)$^-$, HRMS: calcd. 675.2700 and found 675.2708 (M+H)$^+$, mp 153-155° C., $^1$H NMR (300 MHz, $CDCl_3$) δ ppm 0.88-0.97 (m, 1H), 1.01-1.09 (m, 1H), 1.11-1.20 (m, 2H), 1.27 (s, 9H), 1.89-1.93 (m, 1H), 1.97-2.03 (m, 1H), 2.45-2.54 (m, 1H), 2.59-2.68 (m, 2H), 2.84-2.91 (m, 1H), 3.41-3.46 (t, J=6Hz, 1H), 3.47-3.49 (t, J=3Hz, 2H), 3.69-3.75 (dd, J=6 and 12Hz, 1H), 3.85-3.90 (dd, J=3 and 12Hz, 1H), 4.19-4.25 (t, J=7Hz, 1H), 4.34-4.43 (m, 2H), 4.54-4.61 (m, 1H), 5.03-5.05 (d, J=6 Hz, 1H) 5.19-5.26 (t, J=9Hz, 1H), 5.64 (s, 1H), 5.69-5.76 (m, 1H), 6.75 (s, 1H), 7.35-7.40 ($A_2B_2$, 2H), 7.50-7.57 (t, J=5Hz, 1H), 7.95-8.00 ($A_2B_2$, 2H), 10.00 (s, 1H).

Example 39

Preparation of Compound 2

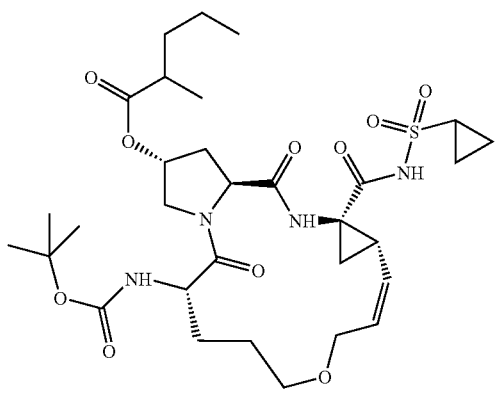

Compound 2

Prepared by way of method I of example 27, using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and 2-methylvaleryl chloride (72 μL, 0.53 mmol). The final trituration (diethyl ether/petroleum ether) and filtration gave 53 mg (45%) of the desired product, 18-(2-methylvaleryloxy)-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 98.8% pure (HPLC), MS m/z 667 (M–H)$^-$, HRMS: calcd. 667.3013 and found 667.3032 (M–H)$^-$, mp 121-123° C.

Example 40

Preparation of Compound 3

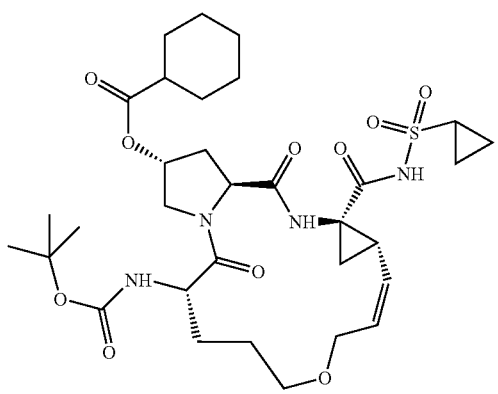

Compound 3

Prepared by way of method I of example 27 using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (50 mg, 0.088 mmol) and cyclohexanecarbonyl chloride (35 μL, 0.26 mmol). The final trituration (diethyl ether/petroleum ether) and filtration gave 16 mg (27%) of 18-cyclohexanecarbonyloxy-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 96.1% pure (HPLC), MS m/z 679 (M–H)$^-$, HRMS: calcd. 679.3013 and found 679.3007 (M–H)$^-$, mp 128-130° C.

Example 41

Preparation of Compound 4

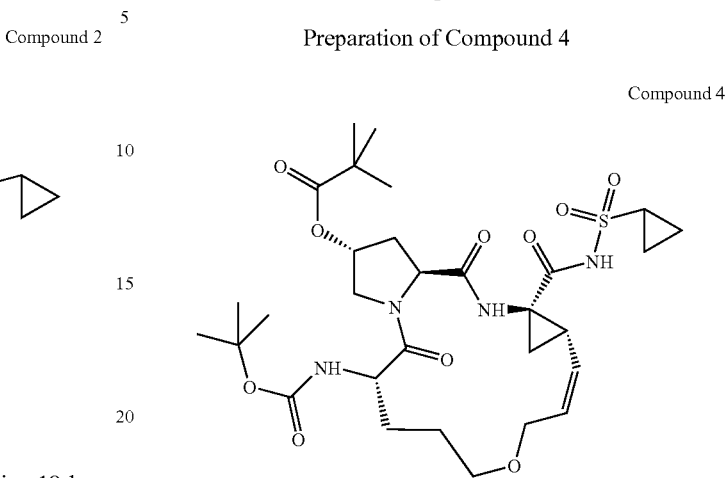

Compound 4

Prepared by way of method I of example 27, using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (50 mg, 0.088 mmol) and pivaloyl chloride (32 μL, 0.26 mmol). The final trituration (diethyl ether/petroleum ether) and filtration gave 15 mg (26%) of the desired product, 18-pivaloyloxy-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 97.9% pure (HPLC), MS m/z 653 (M–H)$^-$, HRMS: calcd. 653.2856 and found 653.2885 (M–H)$^-$, mp 143-145° C.

Example 42

Preparation of Compound 5

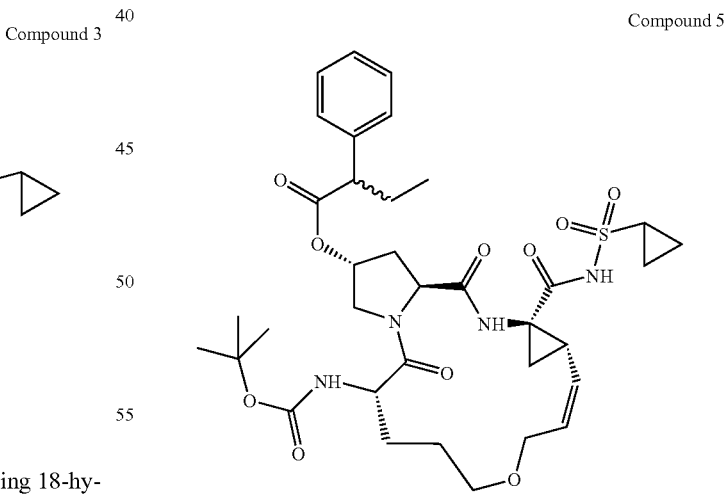

Compound 5

Prepared by way of method I of example 27, using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (50 mg, 0.088 mmol) and 2-phenylbutyryl chloride (44 μL, 0.26 mmol). The final trituration (diethyl ether/petroleum ether) and filtration gave 36 mg (57%) of the desired product, 18-(2-phenylbutyryloxy)-14-tert-butoxycarbonylamino-4-cyclopropylsulfonylaminocarbonyl-2,15-dioxo-3,16-diaza-10-oxatricyclo-

[14.3.0.0⁴,⁶]-nonadec-7-ene as a white powder: 99.7% pure (HPLC), MS m/z 717 (M+H)⁺, HRMS: calcd. 734.3435 and found 734.3403 (M+NH₄)⁺, mp 113-115° C.

Example 43

Preparation of Compound 6

Compound 6

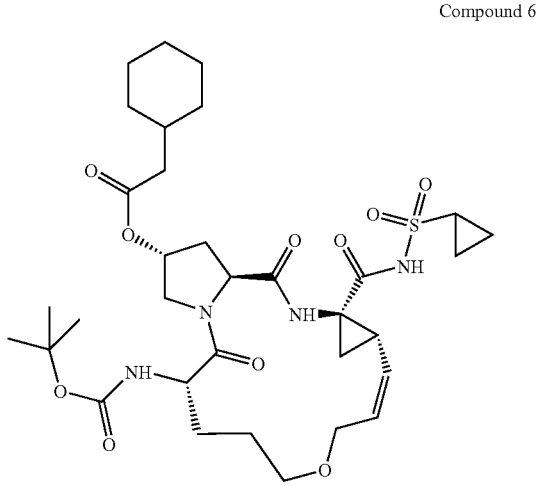

Prepared by way of method I using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and cyclohexaneacetyl chloride (91 µL, 0.53 mmol). The final trituration (diethyl ether/petroleum ether) and filtration gave 11 mg (9.0%) of the desired product, 18-cyclohexaneacetyloxy-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 98.9% pure (HPLC), MS m/z 697 (M+H)⁺, HRMS: calcd. 697.3482 and found 697.3492 (M+H)⁺, mp 107-109° C.

Example 44

Preparation of Compound 7

Compound 7

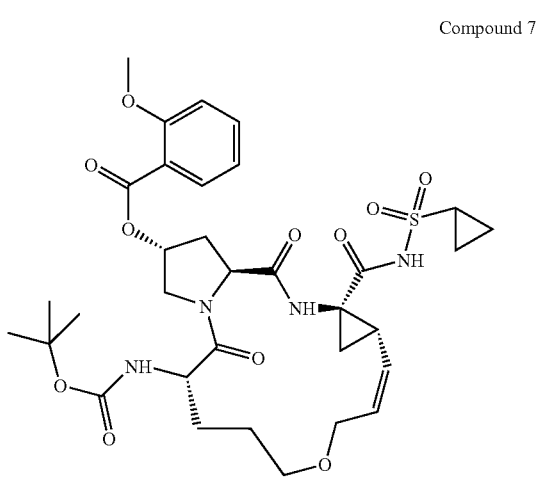

Prepared by way of method I using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and 2-methoxybenzoyl chloride (71 µL, 0.53 mmol). The final trituration (diethyl ether) and filtration gave 59 mg (48%) of the desired product, 18-(2-methoxybenzoyloxy)-14-tert-butoxycarbonylamino-4-cyclopropylsulfonylaminocarbonyl-2,15-dioxo-3,16-diaza-10-oxa-tricyclo-[14.3.0.0$^{4,6}$]-nonadec-7-ene as a white powder: 99.4% pure (HPLC), MS m/z 703 (M–H)⁻, HRMS: calcd. 705.2806 and found 705.2797 (M+H)⁺, mp 144-146° C.

Example 45

Preparation of Compound 8

Compound 8

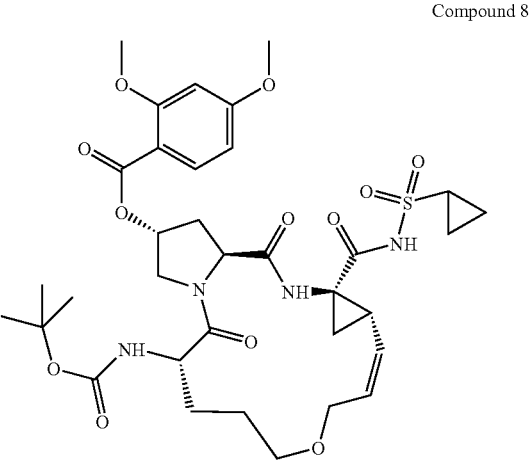

Prepared by way of method II of Example 56 using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and 2,4-dimethoxybenzoyl chloride (105 µL, 0.53 mmol). The final trituration (diethyl ether/hexane) and filtration gave 41 mg (32%) of the desired product, 18-(2,4-dimethoxybenzoyloxy)-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 99.2% pure (HPLC), MS m/z 733 (M–H)⁻, HRMS: calcd. 735.2911 and found 735.2913 (M+H)⁺, mp 122-124° C.

Example 46

Preparation of Compound 9

Compound 9

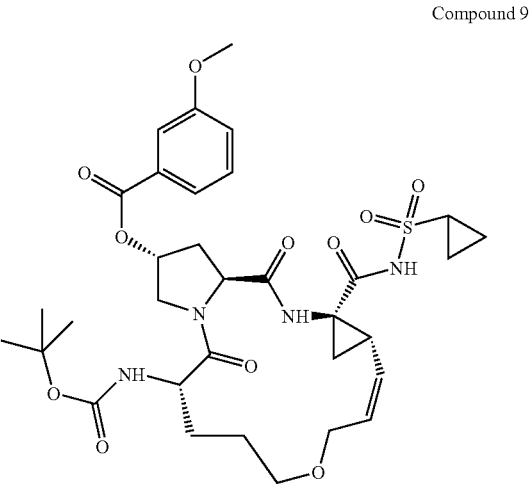

Prepared by way of method I using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and 3-methoxybenzoyl chloride (74 µL, 0.53 mmol). The final trituration (diethyl ether/hexane) and filtration gave 56 mg (45%) of 18-(3-methoxybenzoyloxy)-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder:

98.7% pure (HPLC), MS m/z 703 (M–H)⁻, HRMS: calcd. 705.2806 and found 705.2782 (M+H)⁺, mp 149-151° C.

Example 47

Preparation of Compound 10

Compound 10

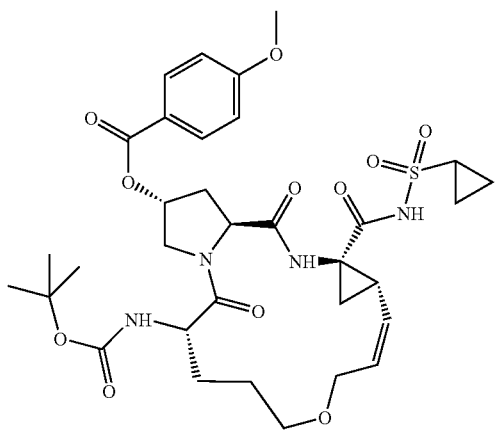

Prepared by way of method I using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and 4-methoxybenzoyl chloride (89 mg, 0.53 mmol). The final trituration (diethyl ether) and filtration gave 44 mg (36%) of 18-(4-methoxybenzoyloxy)-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 98.9% pure (HPLC), MS m/z 703 (M–H)⁻, HRMS: calcd. 705.2806 and found 705.2801 (M+H)⁺, mp 145-147° C.

Example 48

Preparation of Compound 11

Compound 11

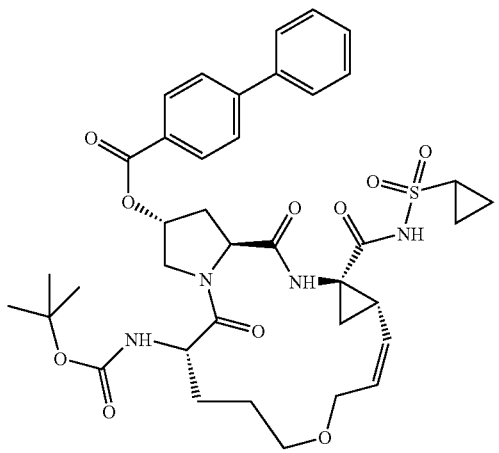

Prepared by way of method I using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and 4-biphenylcarbonyl chloride (113 mg, 0.53 mmol). The final trituration (diethyl ether/hexane) and filtration gave 35 mg (27%) of 18-(4-biphenylcarbonyloxy)-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 98.9% pure (HPLC), MS m/z 749 (M–H)⁻, HRMS: calcd. 751.3013 and found 751.3008 (M+H)⁺, mp 160-162° C.

Example 49

Preparation of Compound 12

Compound 12

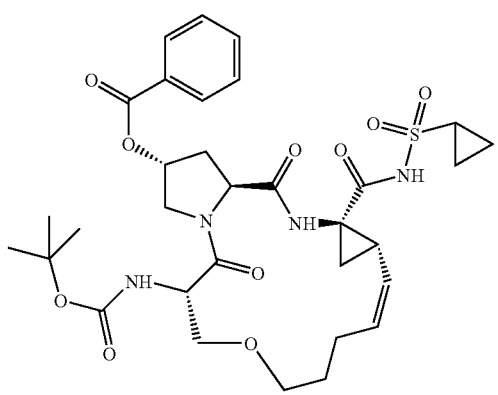

Prepared by way of method I using 18-hydroxy-14-tert-butoxycarbonylamino-4-cyclopropylsulfonylaminocarbonyl-2,15-dioxo-3,16-diaza-12-oxatricyclo[14.3.0.0$^{4,6}$]-nonadec-7-ene (100 mg, 0.175 mmol) and benzoyl chloride (61 µL, 0.53 mmol). The final trituration (diethyl ether/hexane) and filtration gave 56 mg (48%) of 18-benzoyloxy-14-tert-butoxycarbonylamino-4-cyclopropylsulfonylaminocarbonyl-2,15-dioxo-3,16-diaza-12-oxatricyclo-[14.3.0.0$^{4,6}$]-nonadec-7-ene as a white powder: 99.0% pure (HPLC), MS m/z 673 (M–H)⁻, HRMS: calcd. 675.2700 and found 675.2709 (M+H)⁺, mp 135-137° C.

Example 50

Preparation of Compound 13

Compound 13

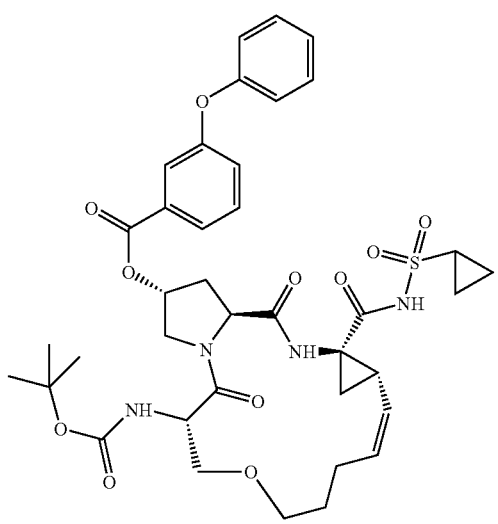

Prepared by way of method I using 18-hydroxy-14-tert-butoxycarbonylamino-4-cyclopropylsulfonylaminocarbonyl-2,15-dioxo-3,16-diaza-12-oxatricyclo[14.3.0.0$^{4,6}$]-nonadec-7-ene (100 mg, 0.175 mmol) and 3-phenoxybenzoyl chloride (122 µL, 0.53 mmol). The final trituration (diethyl ether/hexane) and filtration gave 21 mg (16%) of 18-(3-phe- 12noxybenzoyloxy)-14-tert-butoxycarbonylamino-4-cyclopropylsulfonylaminocarbonyl-2,15-dioxo-3,16-diaza-12-oxatricyclo-[14.3.0.0$^{4,6}$]-nonadec-7-ene as a white powder: 98.0% pure (HPLC), MS m/z 765 (M–H)$^-$, HRMS: calcd. 767.2962 and found 767.2971 (M+H)$^+$, mp 123-125° C.

Example 51

Preparation of Compound 14

Compound 14

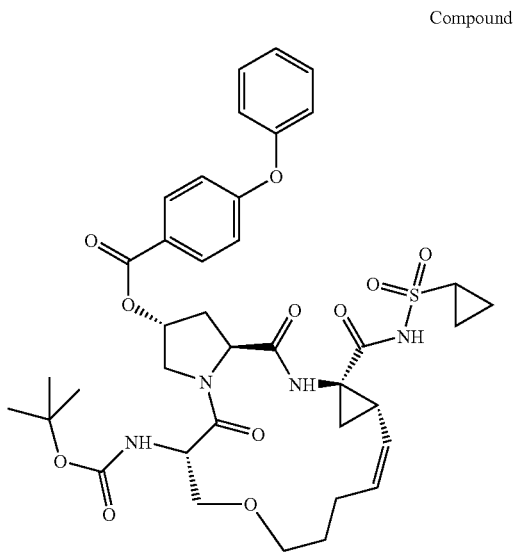

Prepared by way of method I using 18-hydroxy-14-tert-butoxycarbonylamino-4-cyclopropylsulfonylaminocarbonyl-2,15-dioxo-3,16-diaza-12-oxatricyclo[14.3.0.0$^{4,6}$]-nonadec-7-ene (100 mg, 0.175 mmol) and 4-phenoxybenzoyl chloride (111 mg, 0.53 mmol). The final trituration (diethyl ether/hexane) and filtration gave 16 mg (12%) of 18-(4-phenoxybenzoyloxy)-14-tert-butoxycarbonylamino-4-cyclopropylsulfonylaminocarbonyl-2,15-dioxo-3,16-diaza-12-oxatricyclo-[14.3.0.0$^{4,6}$]-nonadec-7-ene as a white powder: 97.5% pure (HPLC), MS m/z 765 (M–H)$^-$, HRMS: calcd. 784.3228 and found 784.3208 (M+NH$_4$)$^+$, mp 207-209° C.

Example 52

Preparation of Compound 15

Compound 15

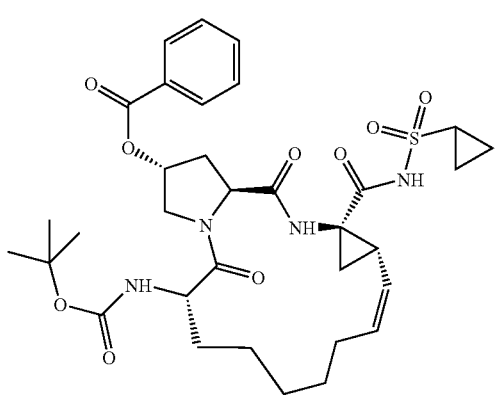

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and benzoyl chloride (41 μL, 0.35 mmol). The final trituration (diethyl ether/hexane) and filtration gave 18 mg (15%) of 18-benzoyloxy-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 97.0% pure (HPLC), MS m/z 673 (M+H)$^+$, HRMS: calcd. 673.2907 and found 673.2908 (M+H)$^+$, mp 140-142° C.

Example 53

Preparation of Compound 16

Compound 16

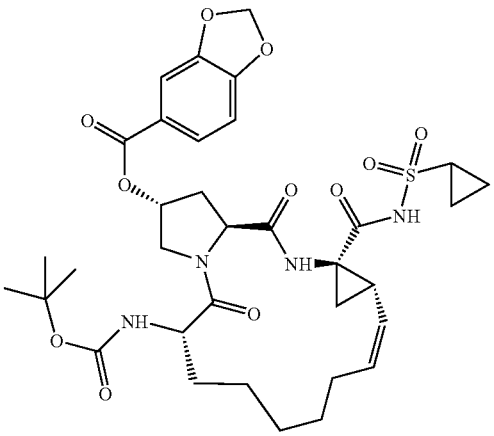

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 3,4-methylenedioxybenzoyl chloride (65 μL, 0.35 mmol). The final trituration (diethyl ether/hexane) and filtration gave 44 mg (35%) of 18-(3,4-methylenedioxybenzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 98.6% pure (HPLC), MS m/z 717 (M+H)$^+$, HRMS: calcd. 717.2806 and found 717.2789 (M+H)$^+$, mp 153-155° C.

Example 54

Preparation of Compound 17

Compound 17

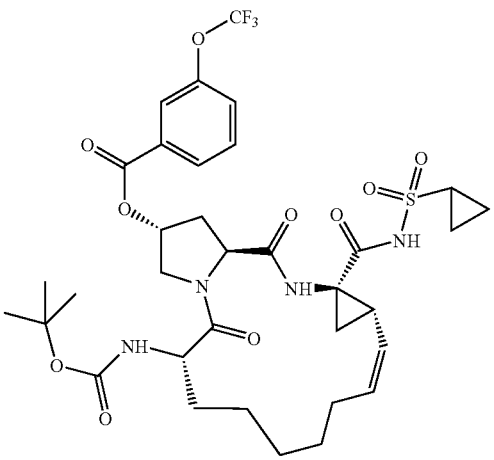

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 3-(trifluoromethoxy)benzoyl chloride (54 μL, 0.35 mmol). The final trituration (diethyl ether/hexane) and filtration gave 72 mg (54%) of 18-[(3-trifluoromethoxy)benzoyloxy]-14-tert-butoxycarbonylamino-4-cyclopropylsulfonylaminocarbonyl-2,15-dioxo- 3,16-diazatricyclo-[14.3.0.0^{4,6}]-nonadec-7-ene as a white powder: 99.0% pure (HPLC), MS m/z 755 (M−H)⁻, HRMS: calcd. 774.2996 and found 774.3012 (M+NH₄)⁺, mp 132-134° C.

Example 55

Preparation of Compound 18

Compound 18

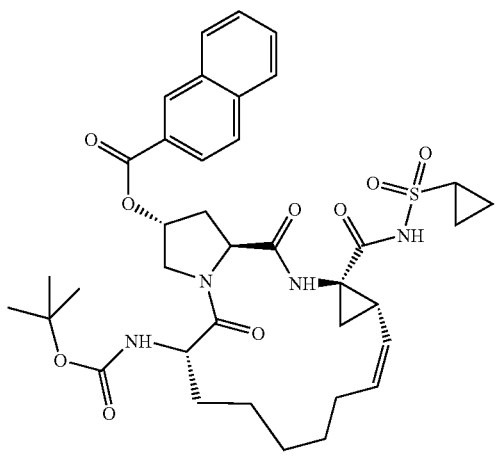

Prepared by way of method I using 18-hydroxy-14-tert-butoxycarbonylamino-4-cyclopropylsulfonylaminocarbonyl-2,15-dioxo-3,16-diazatricyclo[14.3.0.0^{4,6}]-nonadec-7-ene (100 mg, 0.175 mmol) and 2-naphthoyl chloride (66 mg, 0.35 mmol). The final trituration (diethyl ether/hexane) and filtration gave 33 mg (26%) of 18-(2-naphthoyloxy)-14-tert-butoxycarbonylamino-4-cyclopropylsulfonylaminocarbonyl-2,15-dioxo-3,16-diazatricyclo-[14.3.0.0^{4,6}]-nonadec-7-ene as a white powder: 98.5% pure (HPLC), MS m/z 721 (M−H)⁻, HRMS: calcd. 740.3329 and found 740.3321 (M+NH₄)⁺, mp 156-158° C.

Example 56

Preparation of Compound 19

Compound 19

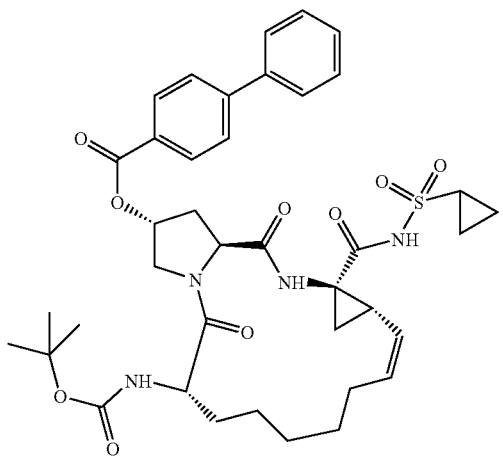

Method II: The intermediate 18-hydroxy-14-tert-butoxycarbonylamino-4-cyclopropylsulfonylaminocarbonyl-2,15-dioxo-3,16-diazatricyclo[14.3.0.0^{4,6}]-nonadec-7-ene (100 mg, 0.175 mmol) and 4-biphenylcarbonyl chloride (76 mg, 0.34 mmol) was dissolved in a solution of dichloromethane (2 mL) and pyridine (1 mL). Care was taken to avoid moisture by using oven-dried glassware and maintaining a dry N₂ atmosphere above the reaction. The progression of the reaction was checked by LCMS. The reaction was refluxed under nitrogen for 12 hours. Upon cooling, the reaction was diluted with ether. The solution was washed with aqueous 1N HCl then brine. The organic phase was dried (MgSO₄), decanted off the drying agent and concentrated in vacuo to give the crude product. Flash chromatography of the residue (silica gel, 80% hexane/ethyl acetate with 0.1% acetic acid), upon combining and evaporating the appropriate fractions, gave the desired product at 98.4% purity. The residue was triturated in ether/hexane and filtration gave 49 mg (37%) of 18-(4-biphenylcarbonyloxy)-14-tert-butoxycarbonylamino-4-cyclopropylsulfonylaminocarbonyl-2,15-dioxo-3,16-diazatricyclo-[14.3.0.0^{4,6}]-nonadec-7-ene as a white powder: 97.6% pure (HPLC), MS m/z 747 (M−H)⁻, HRMS: calcd. 766.3486 and found 766.3497 (M+NH4)⁺, mp 162-164° C. ¹H NMR (300 MHz, CDCl₃) δ ppm 0.83-0.94 (m, 2H), 0.98-1.20 (m, 4H), 1.26 (m, 9H), 1.70-1.86 (m, 2H), 1.89-1.93 (dd, J=6 and 7Hz, 2H), 2.21-2.80 (dd, J=9 and 18Hz, 1H), 2.53-2.64 (m, 3H), 2.83-2.92 (m, 1H), 3.93 (s, 2H), 4.20-4.27 (m, 1H), 4.53-4.58 (t, J=9Hz, 2H), 4.93-4.99 (t, J=9Hz, 1H), 5.18 (s, 1H), 5.62-5.67 (m, 2H), 6.79 (s, 1H), 7.35-7.47 (m, 4H), 7.53-7.63 (m, 5H), 8.00-8.06 (t, J=9Hz, 2H), 10.20 (s, 1H).

Example 57

Preparation of Compound 20

Compound 20

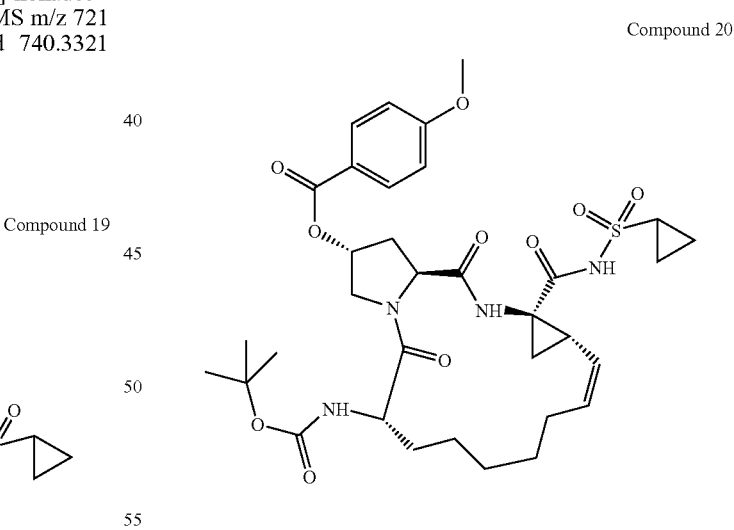

Prepared by way of method I using 18-hydroxy-14-tert-butoxycarbonylamino-4-cyclopropylsulfonylaminocarbonyl-2,15-dioxo-3,16-diazatricyclo[14.3.0.0^{4,6}]-nonadec-7-ene (100 mg, 0.175 mmol) and 4-methoxybenzoyl chloride (72 mg, 0.53 mmol). The final trituration (diethyl ether/hexane) and filtration gave 33 mg (27%) of 18-(4-methoxybenzoyloxy)-14-tert-butoxycarbonylamino-4-cyclopropylsulfonylaminocarbonyl-2,15-dioxo-3,16-diazatricyclo-[14.3.0.0^{4,6}]-nonadec-7-ene as a white powder: 98.0% pure (HPLC), MS m/z 701 (M−H)⁻, HRMS: calcd. 703.3013 and found 703.3006 (M+H)⁺, mp 151-153° C.

Example 58

Preparation of Compound 21

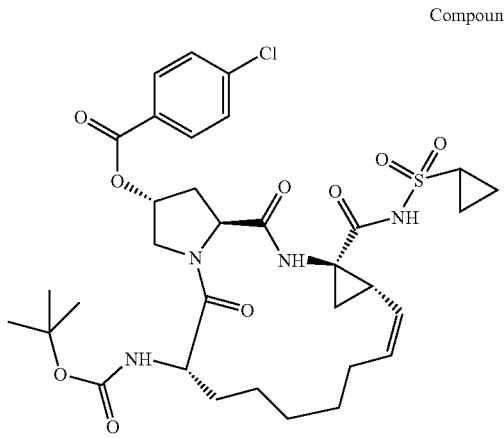

Compound 21

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 4-chlorobenzoyl chloride (45 µL, 0.35 mmol). The final trituration (diethyl ether/hexane) and filtration gave 68 mg (55%) of 18-(4-chlorobenzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 98.5% pure (HPLC), MS m/z 705 (M−H)⁻, HRMS: calcd. 707.2518 and found 707.2499 (M+H)⁺, mp 143-145° C.

Example 59

Preparation of Compound 22

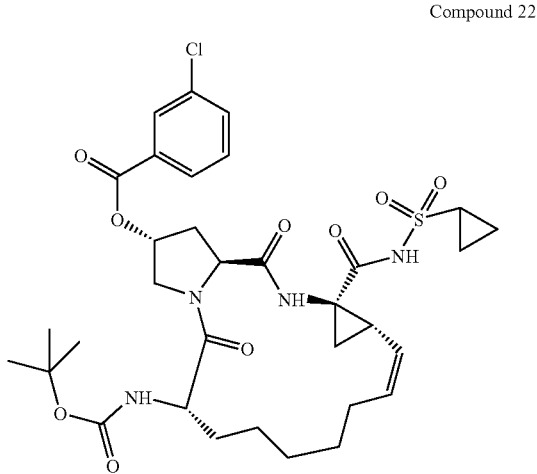

Compound 22

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 3-chlorobenzoyl chloride (45 µL, 0.35 mmol). The final trituration (diethyl ether/hexane) and filtration gave 119 mg (94%) of 18-(3-chorobenzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 98.4% pure (HPLC), MS m/z 705 (M−H)⁻, HRMS: calcd. 707.2518 and found 707.2531 (M+H)⁺, mp 154-156° C.

Example 60

Preparation of Compound 23

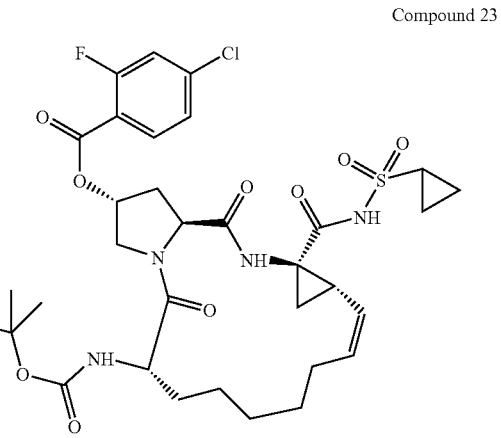

Compound 23

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 4-chloro-2-fluorobenzoyl chloride (47 µL, 0.35 mmol). The final trituration (diethyl ether/hexane) and filtration gave 11 mg (8.7%) of 18-(4-chloro-3-fluorobenzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 99.0% pure (HPLC), MS m/z 723 (M−H)⁻, HRMS: calcd. 742.2689 and found 742.2677 (M+NH₄)⁺, mp 147-149° C.

Example 61

Preparation of Compound 24

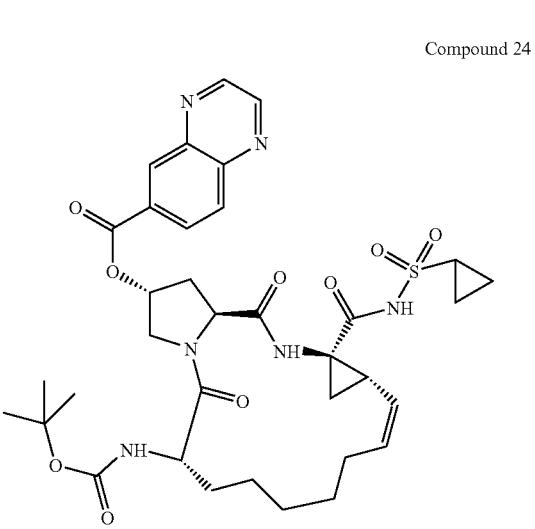

Compound 24

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.176 mmol) and 6-quinoxalinecarbonyl chloride (68 mg, 0.35 mmol). The final trituration (diethyl ether/hexane) and filtration gave 48 mg (38%) of 18-(6-quinoxalinecarbonyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 98.5% pure (HPLC), MS m/z 723 (M–H)⁻, HRMS: calcd. 725.2969 and found 725.2947 (M+H)⁺, mp 158-160° C.

Example 62

Preparation of Compound 25

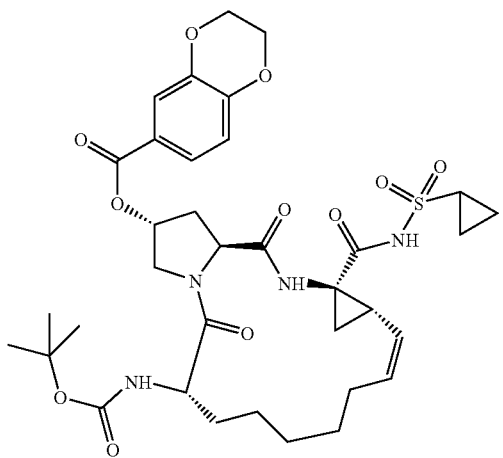

Compound 25

Prepared by way of method II using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 2,3-dihydro-1,4-benzodioxine-6-carbonyl chloride (105 mg, 0.53 mmol). The final trituration (diethyl ether/hexane) and filtration gave 50 mg (39%) of 18-(2,3-dihydro-1,4-benzodioxine-6-carbonyloxy)-14-tert-butoxycarbonylamino-4-cyclopropylsulfonylaminocarbonyl-2,15-dioxo-3,16-diazatricyclo-[14.3.0. 0$^{4,6}$]-nonadec-7-ene as a white powder: 99.5% pure (HPLC), MS m/z 729 (M–H)⁻, HRMS: calcd. 748.3228 and found 748.3220 (M+NH$_4$)⁺, mp 199-201° C.

Example 63

Preparation of Compound 26

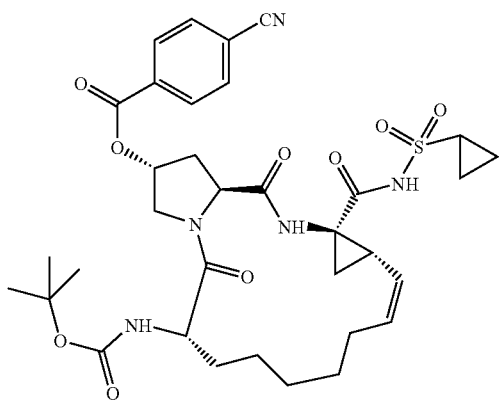

Compound 26

Prepared by way of method II using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 4-cyanobenzoyl chloride (87 mg, 0.53 mmol). The final trituration (diethyl ether/hexane) and filtration gave 45 mg (37%) of 18-(4-cyanobenzoyloxy)-14-tert-butoxycarbonylamino-4-cyclopropylsulfonylaminocarbonyl-2,15-dioxo-3,16-diazatricyclo-[14.3.0. 0$^{4,6}$]-nonadec-7-ene as a white powder: 99.0% pure (HPLC), MS m/z 696 (M–H)⁻, HRMS: calcd. 715.3125 and found 715.3147 (M+NH$_4$)⁺, mp 164-166° C.

Example 64

Preparation of Compound 27

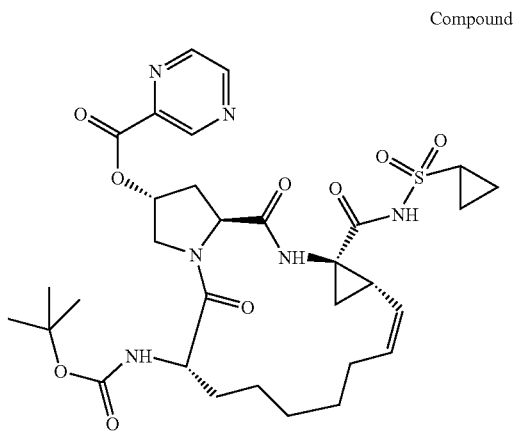

Compound 27

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and pyrazinecarbonyl chloride (75 mg, 0.53 mmol). The final trituration (diethyl ether/hexane) and filtration gave 62 mg (52%) of 18-(pyrazinecarbonyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 98.8% pure (HPLC), MS m/z 673 (M–H)⁻, HRMS: calcd. 675.2812 and found 675.2792 (M+H)⁺, mp 150-152° C.

Example 65

Preparation of Compound 28

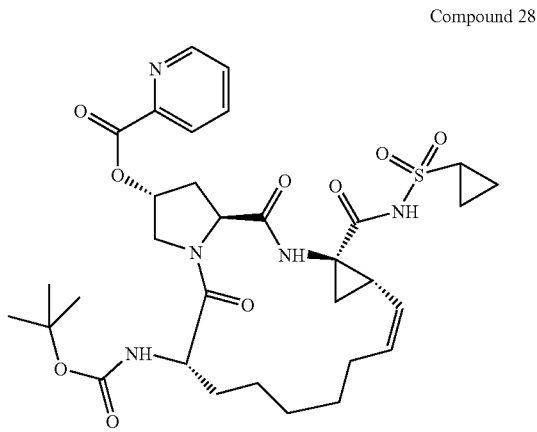

Compound 28

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec- 7-ene (100 mg, 0.175 mmol) and picolinoyl chloride (94 mg, 0.53 mmol). The final trituration (diethyl ether/hexane) and filtration gave 42 mg (54%) of 18-(picolinoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 99.8% pure (HPLC), MS m/z 672 (M−H)$^−$, HRMS: calcd. 674.2860 and found 674.2861 (M+H)$^+$, mp 164-166° C.

Example 66

Preparation of Compound 29

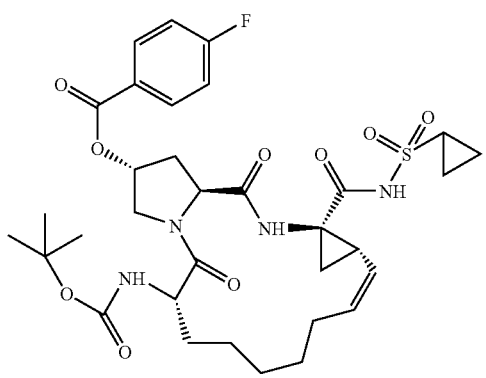

Compound 29

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.176 mmol) and 4-fluorobenzoyl chloride (42 mg, 0.35 mmol). The final trituration (diethyl ether/hexane) and filtration gave 11 mg (9.1%) of 18-(4-fluorobenzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 95.0% pure (HPLC), MS m/z 689 (M−H)$^−$, HRMS: calcd. 691.2813 and found 691.2827 (M+H)$^+$, mp 154-156° C.

Example 67

Preparation of Compound 30

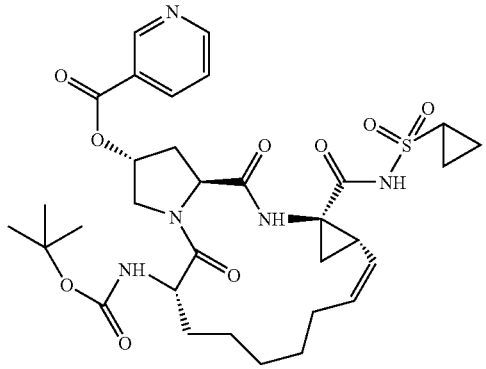

Compound 30

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and nicotinoyl chloride (94 mg, 0.53 mmol). The final trituration (diethyl ether/hexane) and filtration gave 9.0 mg (8.0%) of 18-(nicotinoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 95.0% pure (HPLC), MS m/z 672 (M−H)$^−$, HRMS: calcd. 674.2860 and found 674.2855 (M+H)$^+$, mp 157-159° C.

Example 68

Preparation of Compound 31

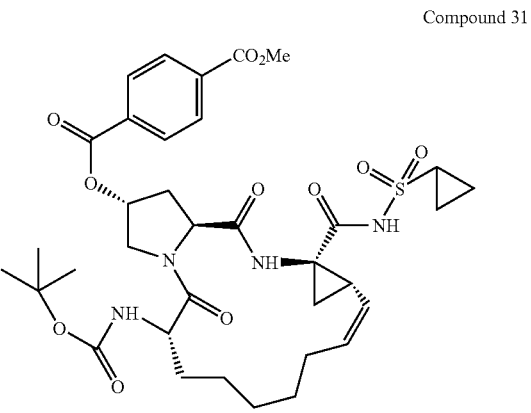

Compound 31

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 4-caboxymethylbenzoyl chloride (70 mg, 0.35 mmol). The final trituration (diethyl ether/hexane) and filtration gave 9.0 mg (7.0%) of 18-(4-carboxymethylbenzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 99.9% pure (HPLC), MS m/z 729 (M−H)$^−$, HRMS: calcd. 731.2962 and found 731.2957 (M+H)$^+$, mp 154-156° C.

Example 69

Preparation of Compound 32

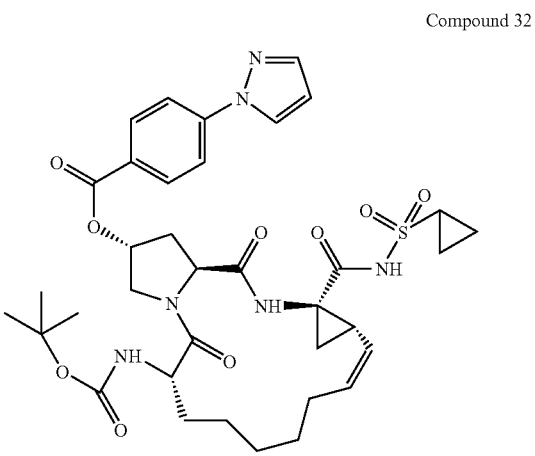

Compound 32

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec- 7-ene (100 mg, 0.175 mmol) and 4-(1-pyrazolyl)benzoyl chloride (183 mg, 0.88 mmol). The final trituration (diethyl ether/hexane) and filtration gave 10 mg (7.7%) of 18-(4-[1-pyrazolyl]benzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 99.9% pure (HPLC), MS m/z 737 (M−H)$^-$, HRMS: calcd. 739.3125 and found 739.3109 (M+H)$^+$, mp 167-169° C.

Example 70

Preparation of Compound 33

Compound 33

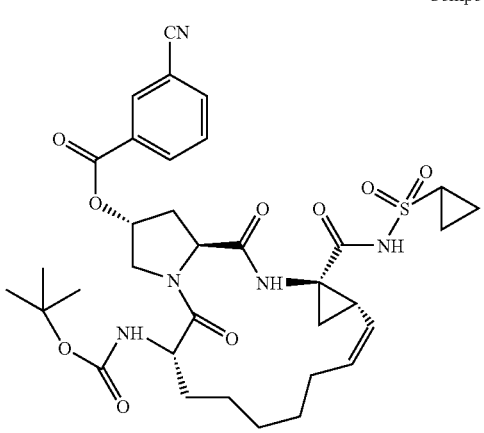

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 3-cyanobenzoyl chloride (87 mg, 0.53 mmol). The final trituration (diethyl ether/hexane) and filtration gave 47 mg (37%) of 18-(3-cyanobenzoyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 98.1% pure (HPLC), MS m/z 696 (M−H)$^-$, HRMS: calcd. 698.2860 and found 698.2849 (M+H)$^+$, mp 151-153° C.

Example 71

Preparation of Compound 34

Compound 34

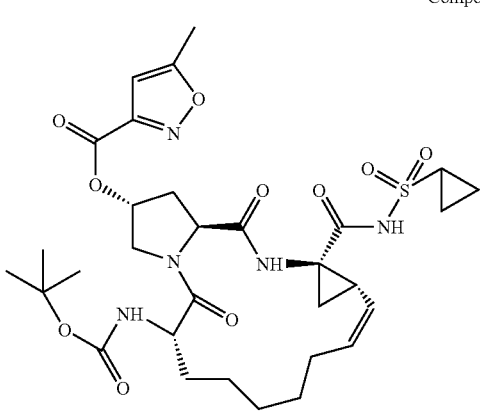

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (100 mg, 0.175 mmol) and 5-methylisoxazole-3-carbonyl chloride (188 mg, 1.06 mmol). The final trituration (diethyl ether/hexane) and filtration gave 31 mg (26%) of 18-(5-methylisoxazole-3-carbonyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 99.9% pure (HPLC), MS m/z 676 (M−H)$^-$, HRMS: calcd. 678.2809 and found 678.2795 (M+H)$^+$, mp 157-159° C.

Example 72

Preparation of Compound 35

Compound 35

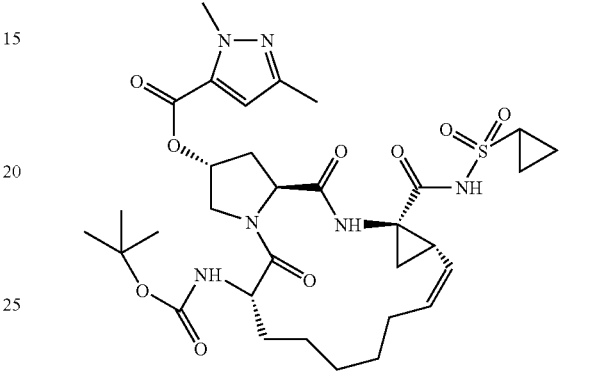

Prepared by way of method I using 18-hydroxy-14-tert-butoxycarbonylamino-4-cyclopropylsulfonylaminocarbonyl-2,15-dioxo-3,16-diazatricyclo[14.3.0.0$^{4,6}$]-nonadec-7-ene (54 mg, 0.095 mmol) and 1,3-dimethylpyrazole-5-carbonyl chloride (23 mg, 0.14 mmol). The final trituration (diethyl ether/hexane) and filtration gave 19 mg (31%) of 18-(1,3-dimethoxypyrazole-5-carbonyloxy)-14-tert-butoxycarbonylamino-4-cyclopropylsulfonylaminocarbonyl-2,15-dioxo-3,16-diazatricyclo-[14.3.0.0$^{4,6}$]-nonadec-7-ene as a white powder: 97.1% pure (HPLC), MS m/z 689 (M−H)$^-$, HRMS: calcd. 691.3125 and found 691.3141 (M+H)$^+$, mp 149-151° C.

Example 73

Preparation of Compound 36

Compound 36

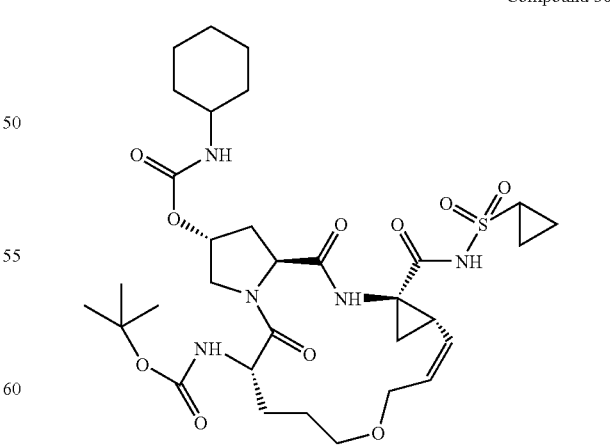

Method III

The intermediate 18-hydroxy-14-tert-butoxycarbonylamino-4-cyclopropylsulfonylaminocarbony-2,15-dioxol-3,16-diaza-10-oxatricyclo[14.3.0.0$^{4,6}$]-nonadec-7-ene (100 mg, 0.175 mmol) and cyclohexyl isocyanate (67 μL, 0.53 mmol) were added to toluene (3 mL). Care was taken to avoid moisture by using oven-dried glassware and maintaining a dry $N_2$ atmosphere above the reaction. The reaction was refluxed under nitrogen for 12 hours. The progression of the reaction was checked by LCMS. Upon cooling, the reaction was diluted with ether. The solution was washed with aqueous 1N HCl then brine. The organic phase was dried ($MgSO_4$), decanted off the drying agent and concentrated in vacuo to give the crude product. Chromatography of the residue ($C_{18}$, 40-80% methanol/water), upon combining and evaporating the appropriate fractions, gave the desired product at 92% purity by HPLC. Flash chromatography of the residue (silica gel, 40% hexane/ethyl acetate with 0.1% acetic acid), upon combining and evaporating the appropriate fractions, gave the desired product at 98.6% purity. The residue was triturated in ether/hexane and filtration gave 31 mg (25%) of 18-(cyclohexylaminocarbonyloxy)-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 99.1% pure (HPLC), MS m/z 694 (M−H)$^-$, HRMS: calcd. 696.3278 and found 696.3262 (M+H)$^+$, mp 156-158° C. $^1$H NMR (300 MHz, CDCl$_3$) δ ppm 0.70-0.93 (m, 2H), 1.03-1.19 (m, 6H), 1.22-1.34 (m, 4H), 1.39 (s, 9H), 1.44-1.53 (m, 3H), 1.87-1.92 (m, 4H), 2.26-2.34 (m, 1H), 2.46-2.54 (m, 1H), 2.55-2.64 (dd, J=18 and 9Hz, 1H), 2.82-2.91 (m, 1H), 3.41-3.49 (m, 3H), 3.71-3.79 (m, 2H), 4.00-4.04 (d, J=12Hz, 1H), 4.25-4.28 (d, J=9Hz, 1H), 4.31-4.37 (dd, J=12 and 6Hz, 1H), 4.46-4.51 (t, J=6Hz, 1H), 4.61-4.63 (d, J=6Hz, 1H), 5.19-5.25 (t, J=9Hz, 2H), 5.35 (s, 1H), 5.67-5.75 (m, 1H), 6.91 (s, 1H), 8.17 (s, 1H), 9.97 (s, 1H).

Example 74

Preparation of Compound 37

Compound 37

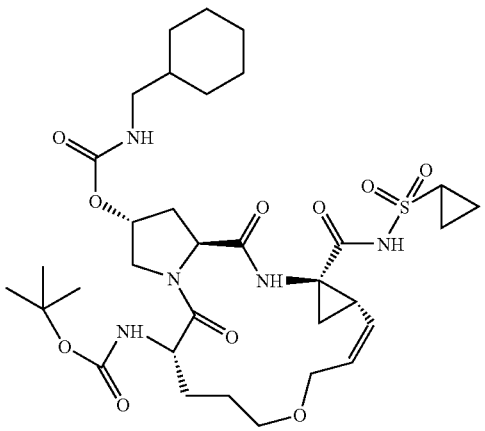

Prepared by way of method III using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and cyclohexylmethyl isocyanate (53 μL, 0.35 mmol). The final trituration (diethyl ether/hexane) and filtration gave 36 mg (29%) of 18-cyclohexylmethylaminocarbonyloxyl-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 99.0% pure (HPLC), MS m/z 708 (M−H)$^-$, HRMS calcd. 708.3278 and found 708.3269, mp 142-144° C.

Example 75

Preparation of Compound 38

Compound 38

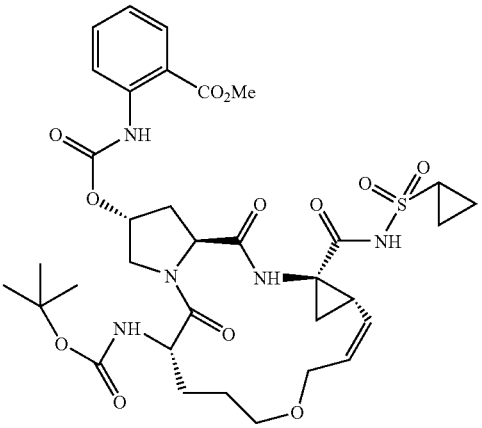

Prepared by way of method III using 18-hydroxy-14-tert-butoxycarbonylamino-4-cyclopropylsulfonylaminocarbonyl-2,15-dioxo-3,16-diaza-10-oxatricyclo[14.3.0.0$^{4,6}$]-nonadec-7-ene (100 mg, 0.175 mmol) and 2-carbomethoxyphenyl isocyanate (62 mg, 0.35 mmol). The final trituration (diethyl ether/hexane) and filtration gave 53 mg (41%) of 18-(2-carbomethoxyphenylaminocarbonyloxy)-14-tert-butoxycarbonylamino-4-cyclopropylsulfonylaminocarbonyl-2,15-dioxo-3,16-diaza-10-oxatricyclo-[14.3.0.0$^{4,6}$]-nonadec-7-ene as a white powder: 99.6% pure (HPLC), MS m/z 746 (M−H)$^-$, HRMS: calcd. 786.2423 and found 786.2436 (M−H+K)$^-$, mp 147-149° C.

Example 76

Preparation of Compound 39

Compound 39

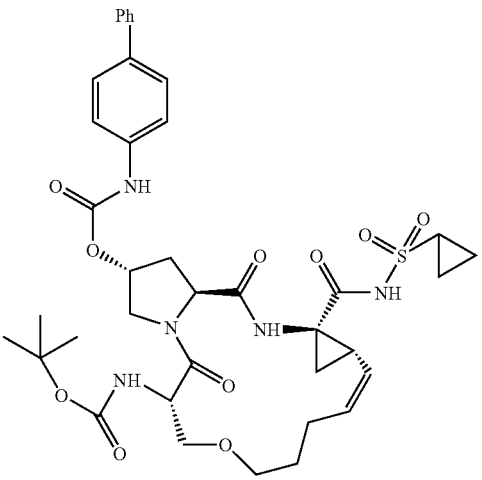

Prepared by way of method III using 18-hydroxy-14-tert-butoxycarbonylamino-4-cyclopropylsulfonylaminocarbonyl-2,15-dioxo-3,16-diaza-12-oxatricyclo[14.3.0.0$^{4,6}$]-nonadec-7-ene (100 mg, 0.175 mmol) and 4-biphenyl isocyanate (102 mg, 0.53 mmol). The final trituration (diethyl ether/hexane) and filtration gave 7.3 mg (5.5%) of 18-(4-biphenylaminocarbonyloxy)-14-tert-butoxycarbonylamino-4-cyclopropylsulfonylaminocarbonyl-2,15-dioxo-3,16- diaza-12-oxatricyclo-[14.3.0.0⁴,⁶]-nonadec-7-ene as a white powder: 95.7% pure (HPLC), MS m/z 764 (M–H)⁻, HRMS: calcd. 783.3387 and found 783.3350 (M+NH₄)⁻, mp 170-173° C.

Example 77

Preparation of Compound 40

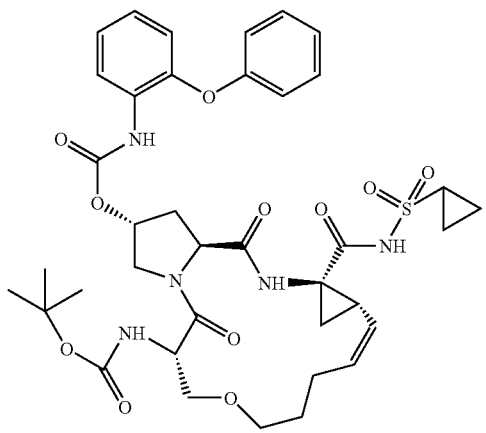

Compound 40

Prepared by way of method III using 18-hydroxy-14-tert-butoxycarbonylamino-4-cyclopropylsulfonylaminocarbonyl-2,15-dioxo-3,16-diaza-12-oxatricyclo[14.3.0.0⁴,⁶]-nonadec-7-ene (100 mg, 0.175 mmol) and 2-phenoxyphenyl isocyanate (94 mg, 0.53 mmol). The final trituration (diethyl ether/hexane) and filtration gave 21 mg (15%) of 18-(2-phenoxyphenylaminocarbonyloxy)-14-tert-butoxycarbonylamino-4-cyclopropylsulfonylaminocarbonyl-2,15-dioxo-3,16-diaza-12-oxatricyclo-[14.3.0.0⁴,⁶]-nonadec-7-ene as a white powder: 99.2% pure (HPLC), MS m/z 780 (M–H)⁻, HRMS: calcd. 799.3337 and found 799.3325 (M+NH₄)⁻, mp 151-153° C.

Example 78

Preparation of Compound 41

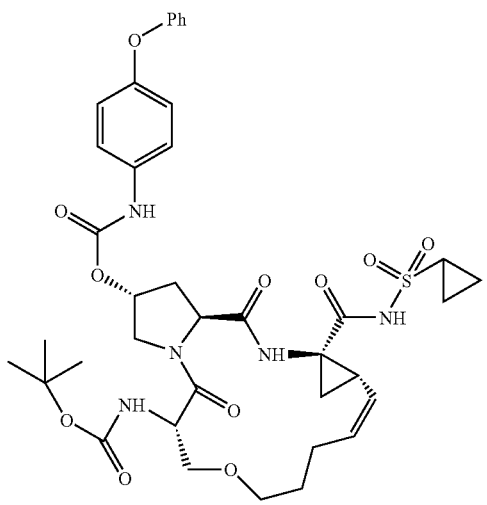

Compound 41

Prepared by way of method III using 18-hydroxy-14-tert-butoxycarbonylamino-4-cyclopropylsulfonylaminocarbonyl-2,15-dioxo-3,16-diaza-12-oxatricyclo[14.3.0.0⁴,⁶]-nonadec-7-ene (100 mg, 0.175 mmol) and 4-phenoxyphenyl isocyanate (111 mg, 0.53 mmol). The final trituration (diethyl ether/hexane) and filtration gave 52 mg (38%) of 18-(4-phenoxyphenylaminocabonyloxy)-14-tert-butoxycarbonylamino-4-cyclopropylsulfonylaminocarbonyl-2,15-dioxo-3,16-diaza-12-oxatricyclo-[14.3.0.0⁴,⁶]-nonadec-7-ene as a white powder: 98.0% pure (HPLC), MS m/z 780 (M–H)⁻, HRMS: calcd. 799.3337 and found 799.3316 (M+NH₄)⁺, mp 163-165° C.

Example 79

Preparation of Compound 42

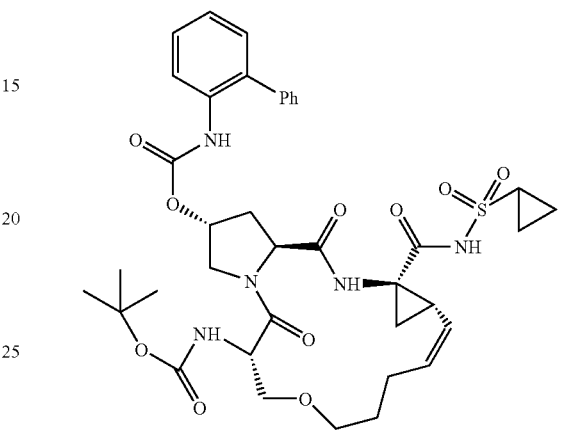

Compound 42

Prepared by way of method III using 18-hydroxy-14-tert-butoxycarbonylamino-4-cyclopropylsulfonylaminocarbonyl-2,15-dioxo-3,16-diaza-12-oxatricyclo[14.3.0.0⁴,⁶]-nonadec-7-ene (100 mg, 0.175 mmol) and 2-biphenyl isocyanate (90 µL, 0.53 mmol). The final trituration (diethyl ether/hexane) and filtration gave 23 mg (17%) of 18-(2-biphenylaminocarbonyloxy)-14-tert-butoxycarbonylamino-4-cyclopropylsulfonylaminocarbonyl-2,15-dioxo-3,16-diaza-12-oxatricyclo-[14.3.0.0⁴,⁶]-nonadec-7-ene as a white powder: 98.5% pure (HPLC), MS m/z 764 (M–H)⁻, HRMS: calcd. 783.3387 and found 783.3408 (M+NH₄)⁺, mp 147-149° C.

Example 80

Preparation of Compound 43

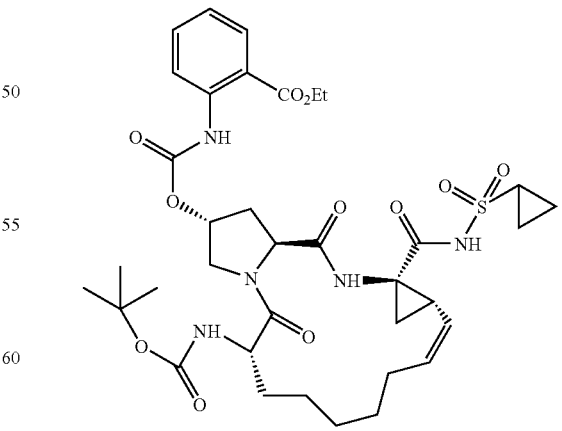

Compound 43

Prepared by way of method III using 18-hydroxy-14-tert-butoxycarbonylamino-4-cyclopropylsulfonylaminocarbonyl-2,15-dioxo-3,16-diaza-12-oxatricyclo[14.3.0.0⁴,⁶]-nonadec-7-ene (100 mg, 0.175 mmol) and 2-carbonylethoxyphenyl isocyanate (102 mg, 0.53 mmol). The final trituration (diethyl ether/hexane) and filtration gave 18 mg (14%) of 18-(2-carbonylethoxyphenylaminocarbonyloxy)-14-tert-butoxycarbonylamino-4-cyclopropylsulfonylaminocarbonyl-2,15-dioxo-3,16-diaza-12-oxatricyclo-[14.3.0.0$^{4,6}$]-nonadec-7-ene as a white powder: 98.9% pure (HPLC), MS m/z 758 (M–H)$^-$, HRMS: calcd. 760.3228 and found 760.3226 (M+NH$_4$)$^+$, mp 148-150° C.

Example 81

Preparation of Compound 44

Compound 44

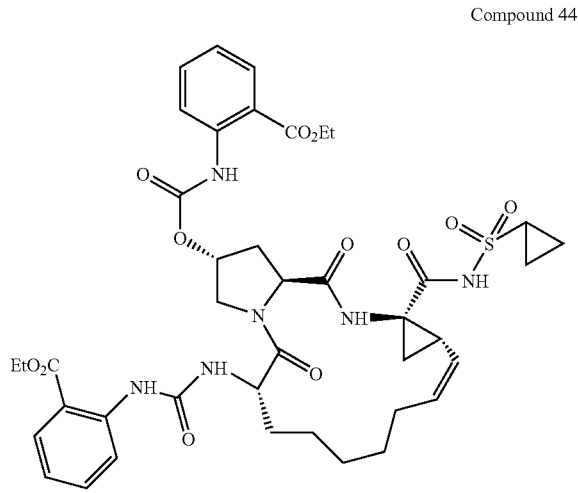

Isolated as a byproduct from the preparation of compound 43. The final trituration (diethyl ether/hexane) and filtration gave 4.2 mg (3.3%) of 18-(2-carboxyethylphenylaminocarbonyloxy)-14-(2-carboxyethoxy)anilinylcarbonylamino-4-cyclopropylsulfonylaminocarbonyl-2,15-dioxo-3,16-diaza-12-oxatricyclo-[14.3.0.0$^{4,6}$]-nonadec-7-ene as a white powder: 99.0% pure (HPLC), MS m/z 849 (M–H)$^-$, HRMS: calcd. 851.3286 and found 851.3294 (M+NH$_4$)$^+$, mp 142-144° C.

Example 82

Preparation of Compound 45

Compound 45

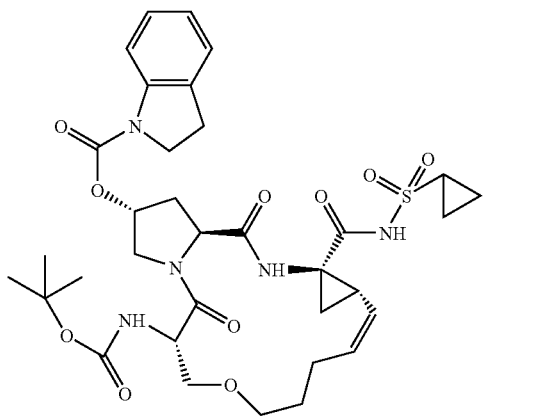

Method IV

The intermediate 18-hydroxy-14-tert-butoxycarbonylamino-4-cyclopropylsulfonylaminocarbony-2,15-dioxol-3,16-diaza-12-oxatricyclo[14.3.0.0$^{4,6}$]-nonadec-7-ene (100 mg, 0.175 mmol) and carbonyl diimidazole (34 mg, 0.21 mmol) were added to dichloromethane (3 mL). Care was taken to avoid moisture by using oven-dried glassware and maintaining a dry N$_2$ atmosphere above the reaction. The reaction was stirred under nitrogen for 4 hours. The progression of the reaction was checked by LCMS. Then indoline was added (59 mL, 0.53 mmol) and the reaction was stirred for 16 hours. The reaction was diluted with ether. The solution was washed with aqueous 1N HCl then brine. The organic phase was dried (MgSO$_4$), decanted off the drying agent and concentrated in vacuo to give the crude product. Chromatography of the residue (silica gel, 80:20:0.1% to 60:40:0.1% hexane/ethyl acetate/AcOH) gave the desired product. The residue was triturated in hexane and filtration gave 59 mg (47%) of 18-(indolinecarbonyloxy)-14-tert-butoxycarbonylamino-4-cyclopropylsulfonylaminocarbonyl-2,15-dioxo-3,16-diaza-12-oxatricyclo-[14.3.0.0$^{4,6}$]-nonadec-7-ene as a white powder: 99.0% pure (HPLC), MS m/z 714 (M–H)$^-$, HRMS: calcd. 733.3231 and found 733.3238 (M+H)$^+$, mp 128-130° C. $^1$H NMR (300MHz, CDCl$_3$) δ ppm 0.90-0.98 (m, 1H), 1.02-1.11 (m, 1H), 1.14-1.25 (m, 2 H), 1.35 (s, 9H), 1.39-1.47 (m, 3H), 1.68-1.77 (m, 1H), 1.90-194 (m, 1 H), 2.08-2.22 (m, 2H), 2.25-2.41 (bs, 3H), 2.70-2.78 (m, 1H), 2.84-2.92 (m, 1H), 3.05-3.11 (t, J=9Hz, 2H), 3.31-3.40 (m, 2H), 3.42-3.47 (t, J=9Hz, 2H), 3.61-3.68 (m, 2H), 3.86-4.05 (m, 3H), 4.60 (bs, 1H), 4.72 (bs, 1H), 5.13-5.19 (t, J=9Hz, 1H), 5.26 (s, 1H), 5.51-5.63 (m, 2H), 6.91-6.96 (t, J=6Hz, 2H), 7.13 (d, J=6Hz, 2H), 7.77-7.82 (m, 1H), 9.93 (s, 1H).

Example 83

Preparation of Compound 46

Compound 46

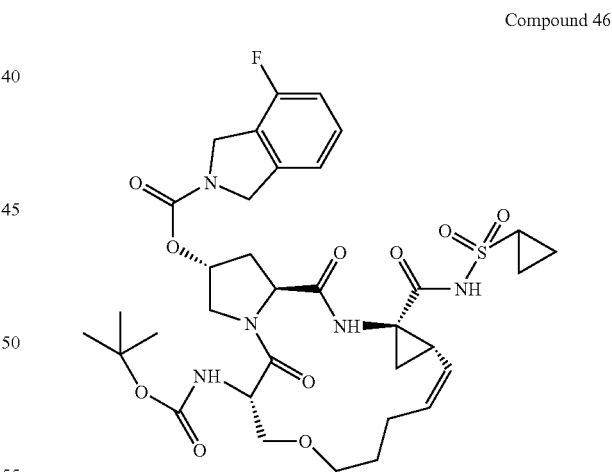

Prepared by way of method III using 18-hydroxy-14-tert-butoxycarbonylamino-4-cyclopropylsulfonylaminocarbony-2,15-dioxol-3,16-diaza-12-oxatricyclo[14.3.0.0$^{4,6}$]-nonadec-7-ene (89 mg, 0.16 mmol), carbonyl diimidazole (30 mg, 0.19 mmol) and 4-fluoroisoindoline (64 mg, 0.47 mmol). The final trituration (hexane) and filtration gave 46 mg (40%) of 18-(2-[4-fluoroisoindoline]carbonyloxy)-14-tert-butoxycarbonylamino-4-cyclopropylsulfonylaminocarbonyl-2,15-dioxo-3,16-diaza-12-oxatricyclo-[14.3.0.0$^{4,6}$]-nonadec-7-ene as a white powder: 98.5% pure (HPLC), MS m/z 723 (M–H)$^-$, HRMS: calcd. and found (M+H)$^+$, mp 151-153° C.

Example 84

Preparation of Compound 47

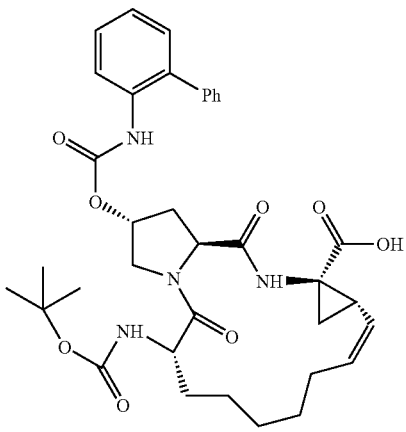

Compound 47

Prepared according to the methods described herein.

Example 85

Preparation of Compound 48

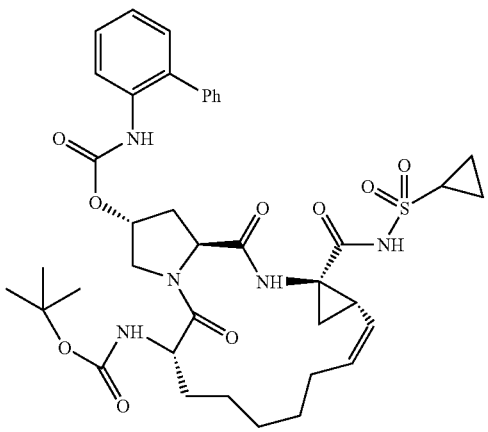

Compound 48

Prepared according to the methods described herein.

Example 86

Preparation of (1S,4R,6S,14S,18R)-[7-cis-4-Cyclopropanesulfonylaminocarbonyl-12-cyclopropyl-18-hydroxy-2,15-dioxo-3,12,16-triaza-tricyclo[14.3.0.0$^{4,6}$]nonadec-7-en-14-yl]carbamic acid, tert-butyl ester (Example 86)

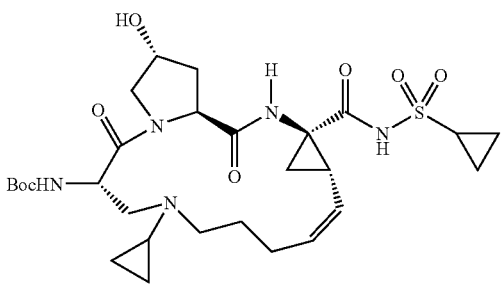

Example 86

Step 1: Synthesis of N-(pent-4-enyl)cyclopropanamine

Using an addition funnel, a solution of 5-bromopentene (15.75 g, 106 mmol) in 50 mL of methanol was added over the course of 5 min to a solution of cyclopropylamine (20.6 g, 361 mmol) in 200 mL of methanol. This solution was allowed to stir at rt for 72 h at which time is was refluxed for 1 h. The methanol and excess cyclopropylamine were removed by distillation. The residue, hydrobromide salt of the product, was partitioned between ether and 4 N NaOH. The aqueous phase was washed with ether (2×). The combined ether extracts were dried (MgSO4), filtered, and concentrated to give 8 g (60%) of N-(pent-4-enyl)cyclopropanamine as a yellow oil: $^1$H NMR (500 MHz, CDCl$_3$) δ 0.31-0.36 (m, 2H) 0.40-0.46 (m, 2H) 1.53-1.63 (m, 2H) 1.87 (brs, 1H) 2.05-2.10 (m, 2H) 2.10-2.14 (m, 1H) 2.69 (t, J=7.32Hz, 2H) 4.91-5.07 (m, 2H) 5.72-5.88 (m, 1H).

Step 2: Synthesis of 2(S)-(tert-butoxycarbonylamino)-3-[N-cyclopropyl-N-(pent-4-enyl)amino]propanoic acid

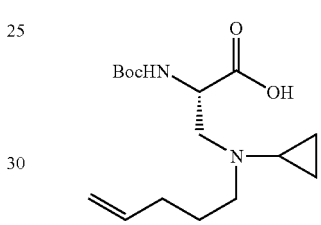

N-(Pent-4-enyl)cyclopropanamine (668 mg, 5.30 mmol) in 20 mL of acetonitrile was added to a slurry of N-t-butoxycarbonyl-L-serine β-lactone (1.0 g, 5.30 mmol) in 40 mL of acetonitrile. The mixture was stirred under N$_2$ at rt for 5 days, and then concentrated in vacuo to give crude 2(S)-(tert-butoxycarbonylamino)-3-[N-cyclopropyl-N-(pent-4-enyl)amino]propanoic acid. This material was used in Step 3 without purification. LC-MS (Phenomenex 10 micromolar ("µm") C18HPLC column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nM. Solvent A: 10% MeOH/90% H$_2$O/0.1% TFA. Solvent B: 10% H$_2$O/90% MeOH/0.1% TFA. (Retention time: 2.50 min), MS m/z 313 (M$^+$+1).

Step 3: Synthesis of ethyl 1(R)-[1-[2(S)-(tert-butoxycarbonylamino)-3-[N-cyclopropyl-N-(pent-4-enyl)amino]propanoyl]-4(R)-hydroxypyrrolidine-2(S)-carboxamido]-2(S)-vinylcyclopropanecarboxylate

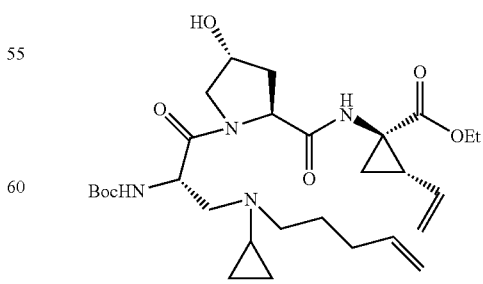

A solution of 2(S)-(tert-butoxycarbonylamino)-3-[N-cyclopropyl-N-(pent-4-enyl)amino]propanoic acid (1.47 g, 4.71 mmoL) in 20 mL of DCM was treated sequentially with ethyl 1(R)-[4(R)-hydroxypyrrolidine-2(S)-carboxamido]-2(S)-vinylcyclopropanecarboxylate hydrochloride (prepared in example 5) (1.44 g, 4.71 mmoL), N-methyl morpholine (1.80 mL, 16.34 mmoL), and HATU (2.14 g, 5.53 mmoL). The reaction mixture was stirred at rt under $N_2$ for 3 h, and then concentrated in vacuo. The residue was dissolved in water and 1N HCl was added until the pH=5. This aqueous solution was extracted with EtOAc (3×). The organic phase was washed with sat. aq. $NaHCO_3$, dried ($MgSO_4$), and concentrated in vacuo to give the crude product. Flash chromatography (50% ethyl acetate/hexane to 100% ethyl acetate) gave 1.55 g (58%) of ethyl 1(R)-[1-[2(S)-(tert-butoxycarbonylamino)-3-[N-cyclopropyl-N-(pent-4-enyl)amino]propanoyl]-4(R)-hydroxypyrrolidine-2(S)-carboxamido]-2(S)-vinylcyclopropanecarboxylate as a white foam:

LC-MS (Phenomenex-Luna S10HPLC column: 3.0×50 mm length. Gradient: 100% Solvent A/0% Solvent B to 0% Solvent A/100% Solvent B. Gradient time: 2 min. Hold time: 1 min. Flow rate: 4 mL/min. Detector Wavelength: 220 nM. Solvent A: 10% MeOH/90% $H_2O$/0.1% TFA. Solvent B: 10% $H_2O$/90% MeOH/0.1% TFA.) (Retention time: 1.38 min), MS m/z 564 ($M^+$+1).

Step 4: Synthesis of ethyl 1(R)-[1-[2(S)-(tert-butoxycarbonylamino)-3-[N-cyclopropyl-N-(pent-4-enyl)amino]propanoyl]-4(R)-(tert-butyldimethylsilyloxy)pyrrolidine-2(S)-carboxamido]-2(S)-vinylcyclopropanecarboxylate

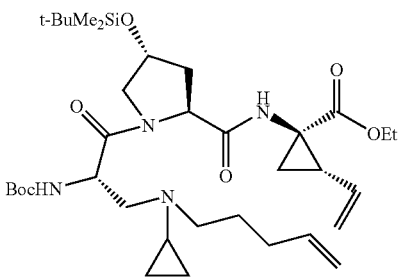

To a mixture of ethyl 1(R)-[1-[2(S)-(tert-butoxycarbonylamino)-3-[N-cyclopropyl-N-(pent-4-enyl)amino]propanoyl]-4(R)-hydroxypyrrolidine-2(S)-carboxamido]-2(S)-vinylcyclopropanecarboxylate (1.55 g, 2.75 mmoL) in 10 mL of DMF was added imidazole (0.47 g, 6.88 mmoL) and tert-butyldimethylsilyl chloride (826 mg, 5.50 mmoL). The mixture was stirred at rt for 18 h, concentrated in vacuo, and partitioned between ethyl acetate and water. The organic phase was dried over magnesium sulfate, and concentrated in vacuo to obtain an off-white solid. Flash chromatography (eluting with methylene chloride and then ethyl acetate) gave ethyl 1(R)-[1-[2(S)-(tert-butoxycarbonylamino)-3-[N-cyclopropyl-N-(pent-4-enyl)amino]propanoyl]-4(R)-(tert-butyldimethylsilyloxy)pyrrolidine-2(S)-carboxamido]-2(S)-vinylcyclopropanecarboxylate as a white solid (1.75 g, 94%): LC-MS (Phenomenex 10 µm C18HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% $H_2O$/0.1% TFA. Solvent B: 10% $H_2O$/90% MeOH/0.1% TFA.) (Retention time: 2.51 min), MS m/z 677 ($M^+$+1).

Step 5: Synthesis of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid, ethyl ester.

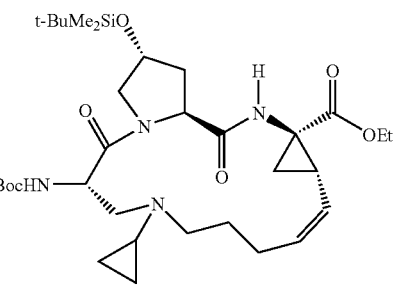

To a solution of ethyl 1(R)-[1-[2(S)-(tert-butoxycarbonylamino)-3-[N-cyclopropyl-N-(pent-4-enyl)amino]propanoyl]-4(R)-(tert-butyldimethylsilyloxy)pyrrolidine-2(S)-carboxamido]-2(S)-vinylcyclopropanecarboxylate (1.45 g, 2.14 mmoL) in 1 L of methylene chloride was added 181 mg (0.21 mmoL) of Grubb's $2^{nd}$ generation catalyst [(1,3-Bis-(2,4,6-trimethylphenyl)-2-imidazolidinylidene)dichloro(phenylmethylene)(tricyclohexylphosphine)ruthenium]. The mixture was heated at reflux for 1 h. A second fraction of the catalyst (50 mg, 0.058 mmol) was added, and the mixture was stirred at rt overnight. The residue was concentrated in vacuo, and then purified by flash chromatography eluting with 50% ether/hexane to give 0.84 g (62%) of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid, ethyl ester as a white solid: LC-MS (Phenomenex 10 µm C18HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% $H_2O$/0.1% TFA. Solvent B: 10% $H_2O$/90% MeOH/0.1% TFA.) (Retention time: 2.43 min), MS m/z 649 ($M^+$+1).

Step 6: Synthesis of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0$^{4,6}$]nonadec-7-ene-4-carboxylic acid

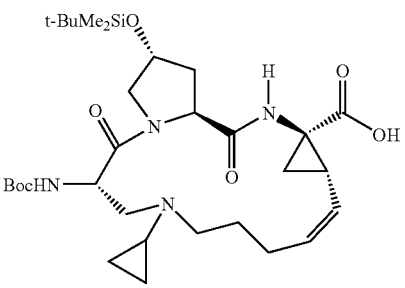

To a solution of (1S,4R,6S,14S,18R)-7-cis-14-tert-Butoxycarbonylamino-18-(tert-butyldimethylsilyloxy)-2,15- dioxo-3,12,16-triazatricyclo[14.3.0.0⁴,⁶]nonadec-7-ene-4-carboxylic acid, ethyl ester (0.84 g, 1.30 mmoL) in THF (30 mL), methanol (15 mL), and water (4 mL), was added powdered lithium hydroxide hydrate (0.31 g, 12.90 mmoL). The resultant light yellow slurry was stirred at rt under $N_2$ overnight. The mixture was then concentrated in vacuo, and partitioned between hexane/ether (1:1) and water. The organic phase was discarded, and the aqueous phase was treated with 1 N HCl until pH 5. This acidic solution was extracted with EtOAc (3×). The combined EtOAc extracts were dried ($MgSO_4$) and concentrated in vacuo to give 0.495 g (61%) of (1S,4R,6S,14S,18R)-7-cis-14-tert-Butoxycarbonylamino-18-(tert-butyldimethylsilyloxy)-2,15-dioxo-3,12,16-triazatricyclo[14.3.0.0⁴,⁶]nonadec-7-ene-4-carboxylic acid as an off-white solid: LC-MS (Phenomenex 10 μm C18HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% $H_2O$/0.1% TFA. Solvent B: 10% $H_2O$/90% MeOH/0.1% TFA.) (Retention time: 2.36 min), MS m/z 621 (M⁺+1).

Step 7: Synthesis of (1S,4R,6S,14S,18R)-[7-cis-4-Cyclopropanesulfonylaminocarbonyl-12-cyclopropyl-18-(tert-butyldimethylsilyloxy)-2,15-dioxo-3,12,16-triaza-tricyclo[14.3.0.0⁴,⁶]nonadec-7-en-14-yl] carbamic acid, tert-butyl ester

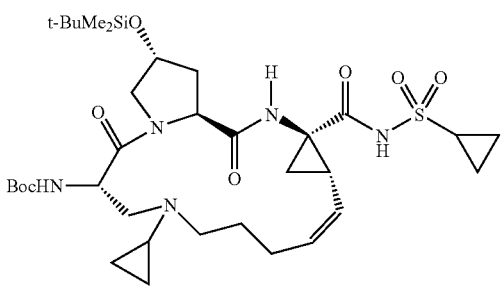

(1S,4R,6S,14S,18R)-7-cis-14-tert-Butoxycarbonylamino-18-(tert-butyldimethylsilyloxy)-2,15-dioxo-3,12,16-triazatricyclo[14.3.0.0⁴,⁶]nonadec-7-ene-4-carboxylic acid (490 mg, 0.79 mmol) was dissolved in 15 mL of THF and treated with CDI (179 mg, 1.10 mmoL). (Care was taken to avoid moisture by using oven dried glassware and maintaining a dry $N_2$ atmosphere.) After refluxing the reaction mixture for two hours, it was cooled to rt and treated sequentially with cyclopropylsulfonamide (134 mg, 1.10 mmoL) and DBU (168 mg, 1.10 mmoL). After stirring overnight at rt, the THF was removed by rotary evaporation. The residue was dissolved in water and 1N HCl was added until the pH=5. This aqueous solution was extracted with EtOAc (3×). The combined EtOAc extracts were dried ($MgSO_4$) and concentrated in vacuo to give the crude product. Purification by flash column, eluting with 3% methanol in methylene chloride, gave 300 mg (53%) of (1S,4R,6S,14S,18R)-[7-cis-4-Cyclopropanesulfonylaminocarbonyl-12-cyclopropyl-18-(tert-butyldimethylsilyloxy)-2,15-dioxo-3,12,16-triaza-tricyclo[14.3.0.0⁴,⁶]nonadec-7-en-14-yl]carbamic acid, tert-butyl ester as a white solid: LC-MS (Phenomenex 10 μm C18HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% $H_2O$/0.1% TFA. Solvent B: 10% $H_2O$/90% MeOH/0.1% TFA.) (Retention time: 2.40 min), MS m/z 724 (M⁺+1).

Step 8: Synthesis of (1S,4R,6S,14S,18R)-[7-cis-4-Cyclopropanesulfonylaminocarbonyl-12-cyclopropyl-18-hydroxy-2,15-dioxo-3,12,16-triaza-tricyclo[14.3.0.0⁴,⁶]nonadec-7-en-14-yl]carbamic acid, tert-butyl ester (Example 86)

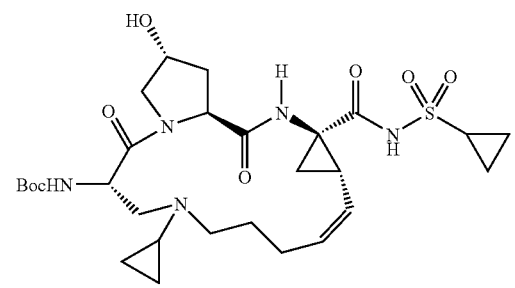

Example 86

To a mixture of compound (1S,4R,6S,14S,18R)-[7-cis-4-Cyclopropanesulfonylaminocarbonyl-12-cyclopropyl-18-(tert-butyldimethylsilyloxy)-2,15-dioxo-3,12,16-triaza-tricyclo[14.3.0.0⁴,⁶]nonadec-7-en-14-yl]carbamic acid, tert-butyl ester (250 mg, 0.35 mmoL) in 15 mL of THF was added tetrabutylammonium fluoride (129 mg, 0.46 mmoL). The mixture was stirred at rt for 18 h. THF was removed by rotary evaporation, and the residue was partitioned between ethyl acetate and water. The organic phase was dried ($MgSO_4$) and concentrated in vacuo to give the crude product. Purification by triturating with hexane provided 200 mg (94%) of (1S,4R, 6S,14S,18R)-[7-cis-4-Cyclopropanesulfonylaminocarbonyl-12-cyclopropyl-18-hydroxy-2,15-dioxo-3,12,16-triaza-tricyclo[14.3.0.0⁴,⁶]nonadec-7-en-14-yl]carbamic acid, tert-butyl ester as a white solid: LC-MS (retention time: 2.32 min), MS m/z 610 (M⁺+1). (Phenomenex 10 μm C18HPLC column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nM. Solvent A: 10% MeOH/90% $H_2O$/0.1% TFA. Solvent B: 10% $H_2O$/90% MeOH/0.1% TFA.) (Retention time: 2.32 min), MS m/z 610 (M⁺+1).

Example 87

Preparation of Compound 49

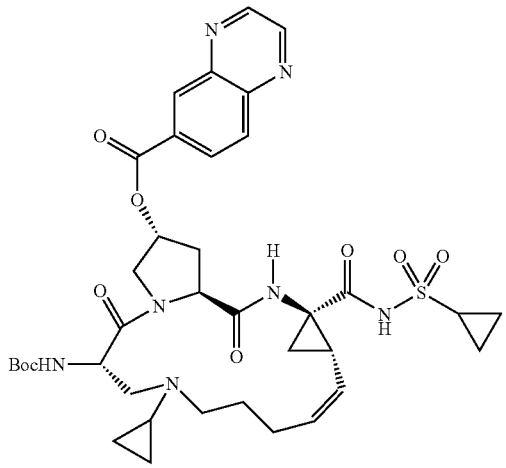

Compound 49

Method V: To a solution of (1S,4R,6S,14S,18R)-[7-cis-4-Cyclopropanesulfonylaminocarbonyl-12-cyclopropyl-18-hydroxy-2,15-dioxo-3,12,16-triazatricyclo[14.3.0.0$^{4,6}$]nonadec-7-en-14-yl]carbamic acid, tert-butyl ester (10 mg, 0.016 mmol) in 2 mL of methylene chloride was added quinoxaline-6-carbonyl chloride (6.16 mg, 0.032 mmol), triethylamine (6.46 mg, 0.064 mmol), and DMAP (1.95 mg, 0.016 mmol). After stirring for 18 h at rt, the reaction was concentrated in vacuo. The residue was dissolved in water and 1N HCl was added until the pH=5. This aqueous solution was extracted with EtOAc (3×). The organic extracts were combined, dried (MgSO4), filtered and concentrated in vacuo to give the crude product. Flash chromatography (EtOAc) gave 5.7 mg (47%) of compound 49 as a white powder: $^1$H NMR (500 MHz, CD$_3$OD) δ 0.68-0.74 (m, 2H), 0.88-1.03 (m, 2H), 1.28 (s, 9H), 1.31-1.38 (m, 2H), 1.50-1.63 (m, 3H), 1.73-1.83 (m, 2H), 1.85 (dd, J=9.31, 5.04Hz, 1H), 1.98 (dd, J=8.09, 5.65Hz, 1H), 2.00-2.05 (m, 1H), 2.60-2.80 (m, 3H), 2.84-3.02 (m, 4H), 3.10-3.19 (m, 1H), 3.46-3.53 (m, 1H), 4.31-4.39 (m, 1H), 4.79-4.92 (m, 2H), 5.01 (d, J=14.04Hz, 1H), 5.26-5.39 (m, 1H), 5.92-6.00 (m, 1H), 6.02 (s, 1H), 8.42 (d, J=8.85Hz, 1H), 8.62 (d, J=8.54Hz, 1H), 8.98 (s, 1H), 9.23 (s, 2H). LC-MS (Phenomenex 10 μm C18 HPLC column: 3.0×50 mm length. Gradient: 100% Solvent A/0% Solvent B to 0% Solvent A/100% Solvent B. Gradient time: 3 min. Hold time: 1 min. Flow rate: 4 mL/min. Detector Wavelength: 220 nM. Solvent A: 10% MeOH/90% H$_2$O/0.1% TFA. Solvent B: 10% H$_2$O/90% MeOH/0.1% TFA. (Retention time: 2.77 min), MS m/z 766 (M$^+$+1).

Example 88

Preparation of Compound 50

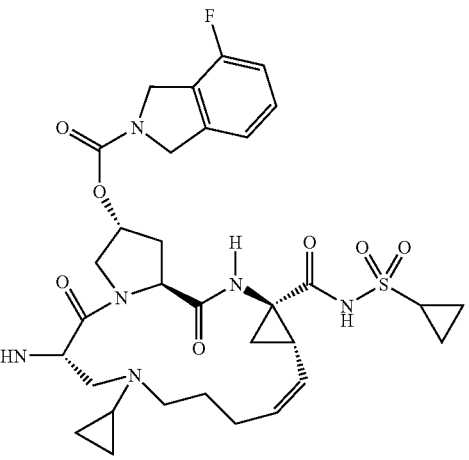

Compound 50

To a solution of (1S,4R,6S,14S,18R)-[7-cis-4-Cyclopropanesulfonylaminocarbonyl-12-cyclopropyl-18-hydroxy-2,15-dioxo-3,12,16-triaza-tricyclo[14.3.0.0$^{4,6}$]nonadec-7-en-14-yl]carbamic acid, tert-butyl ester (14 mg, 0.023 mmol) in 2 mL of methylene chloride was added CDI (5 mg, 0.031 mmol) and the mixture was refluxed for 3 h. It was then cooled to rt and 4-fluoroisoindoline (9 mg, 0.066 mmol) was added. After stirring for 3 h at rt, DIPEA (20 μL, 0.11 mmol) was added and the mixture was stirred at rt for another 10 min. It was then concentrated in vacuo. The residue was dissolved in water and 1N HCl was added until the pH=5. This aqueous solution was extracted with EtOAc (3×). The organic extracts were combined, dried (MgSO$_4$), filtered and concentrated in vacuo to give the crude product. Flash chromatography (3% MeOH/CH$_2$Cl$_2$) gave 3.4 mg (19%) of compound 50 as a white solid: as a white powder: $^1$H NMR (500 MHz, CD$_3$OD) δ 0.67 (d, J=52.19Hz, 2H), 0.97 (d, J=35.71Hz, 2H), 1.21-1.32 (m, 1H), 1.31-1.44 (m, 2H), 1.45-1.55 (m, 9H), 1.54-1.64 (m, 2H), 1.78-1.91 (m, 3H), 1.95-2.10 (m, 2H), 2.53-2.64 (m, 1H), 2.65-2.73 (m, 1H), 2.73-2.86 (m, 2H), 2.87-3.05 (m, 3H), 3.09-3.23 (m, 1H), 3.48-3.55 (m, 1H), 4.26 (d, J=12.51Hz, 1H), 4.69-4.80 (m, 2H), 4.93-5.04 (m, 5H), 5.31-5.41 (m, 1 H), 5.73 (s, 1H), 5.94-6.06 (m, 1H), 7.24-7.46 (m, 2H), 7.55-7.66 (m, 1H). LC-MS (Phenomenex 10 μm C18HPLC column: 3.0×50 mm length. Gradient: 100% Solvent A/0% Solvent B to 0% Solvent A/100% Solvent B. Gradient time: 2 min. Hold time: 1 min. Flow rate: 5 mL/min. Detector Wavelength: 220 nM. Solvent A: 10% MeOH/90% H$_2$O/0.1% TFA. Solvent B: 10% H$_2$O/90% MeOH/0.1% TFA.) (Retention time: 2.20 min), MS m/z 773 (M$^+$+1).

The compounds of Table 3, found below, can be prepared by employing the procedures described herein for the preparation for examples and compounds.

TABLE 1

| Cmpd | R₂ | X | ZR₁ | R₈ | Q |
|---|---|---|---|---|---|
| A | NH-C(O)-O-tBu | O | isoindolin-2-yl | cyclopropyl | N(cyclopropyl)(pent-3-enyl) |
| B | NH-C(O)-O-tBu | O | 1,2,3,4-tetrahydroisoquinolin-2-yl | cyclopropyl | N(cyclopropyl)(pent-3-enyl) |
| C | NH-C(O)-O-tBu | O | 1,2,3,4-tetrahydroisoquinolin-2-yl | N(Me)(Et)-CH< | N(cyclopropyl)(pent-3-enyl) |
| D | NH-C(O)-NH-tBu | O | 1,2,3,4-tetrahydroisoquinolin-2-yl | cyclopropyl | N(cyclopropyl)(pent-3-enyl) |
| E | NH-C(O)-CH₂-tBu | O | 1,2,3,4-tetrahydroisoquinolin-2-yl | cyclopropyl | N(cyclopropyl)(pent-3-enyl) |
| F | NH-C(O)-O-Me | O | 1,2,3,4-tetrahydroisoquinolin-2-yl | cyclopropyl | N(cyclopropyl)(pent-3-enyl) |

TABLE 1-continued

| Cmpd | R₂ | X | ZR₁ | R₈ | Q |
|---|---|---|---|---|---|
| G | NHBoc (tert-butyl carbamate) | O | 4-fluoroisoindolin-2-yl | cyclopropyl | N(CH₂CH₂CH=CH-)C(O)OMe |
| H | NHBoc | O | 1,2,3,4-tetrahydroisoquinolin-2-yl | cyclopropyl | N(CH₂CH₂CH=CH-)C(O)OMe |
| I | NHBoc | O | 4-fluoroisoindolin-2-yl | cyclopropyl | N(CH₂CH₂CH=CH-)C(O)-morpholine |
| J | NHBoc | O | 1,2,3,4-tetrahydroisoquinolin-2-yl | cyclopropyl | N(CH₂CH₂CH=CH-)C(O)-morpholine |
| K | NHBoc | O | 4-fluoroisoindolin-2-yl | cyclopropyl | N(CH₂CH₂CH=CH-)C(O)CH₂NMe₂ |

TABLE 1-continued
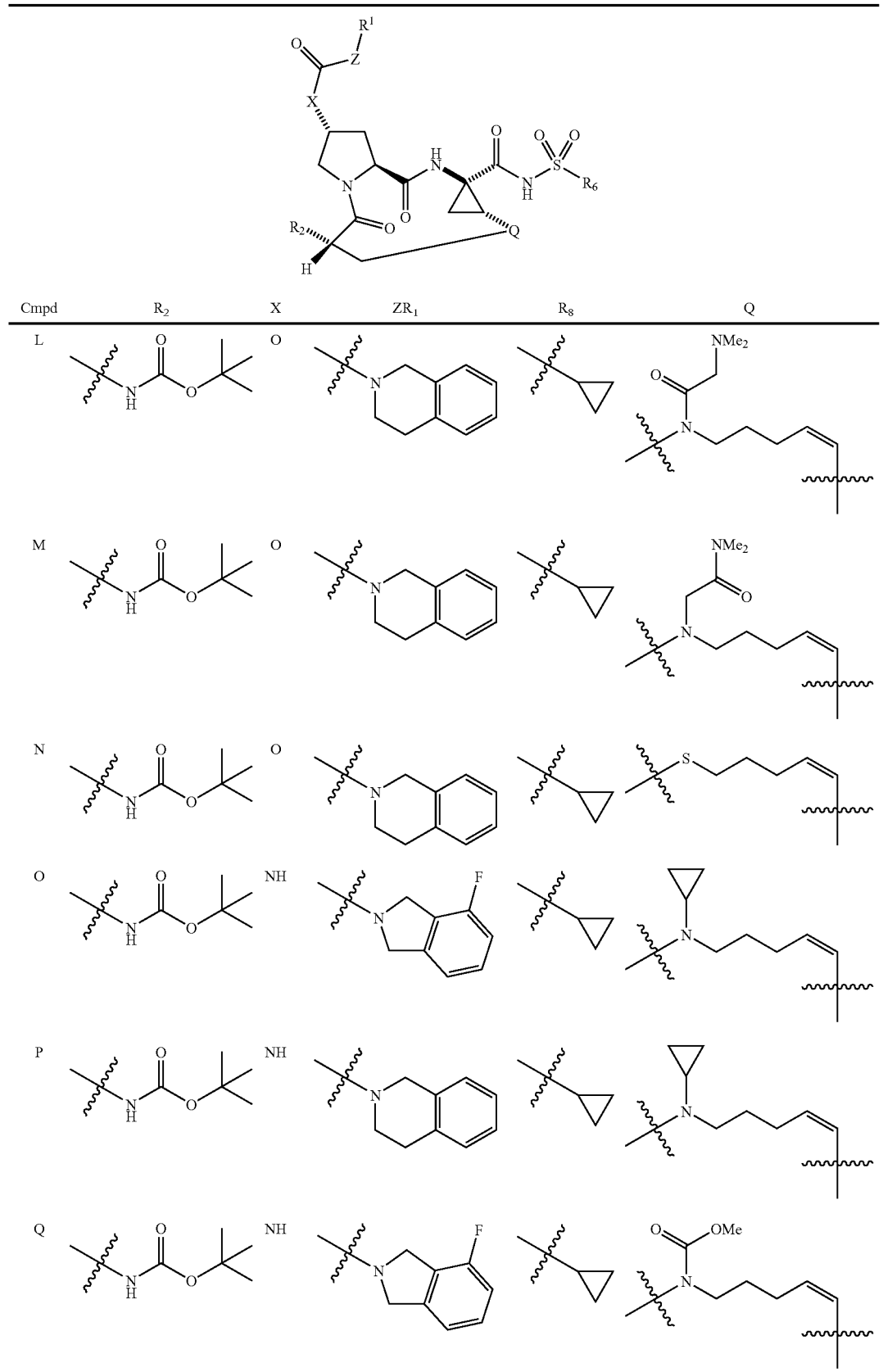

TABLE 1-continued
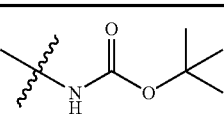
| Cmpd | R₂ | X | ZR₁ | R₈ | Q |
|------|----|----|-----|-----|---|
| R | 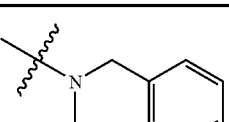 | NH | 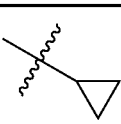 | 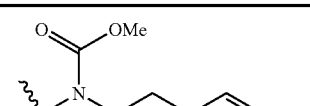 | 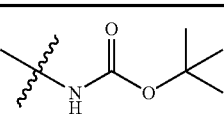 |
| S | 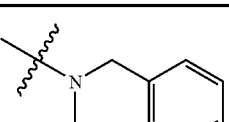 | NH | 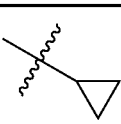 | 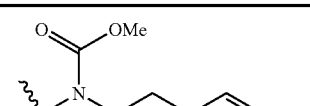 |  |
| T | 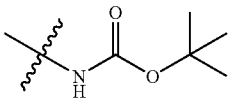 | NH | 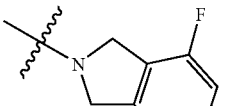 | 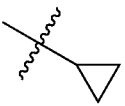 | 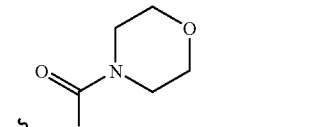 |
| U | 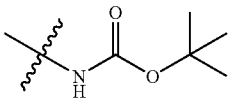 | NH | 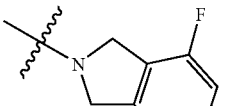 | 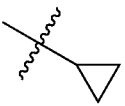 | 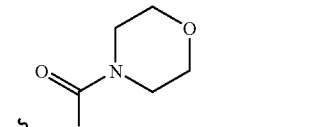 |
| V |  | NH | 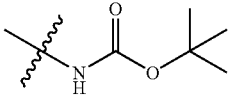 | 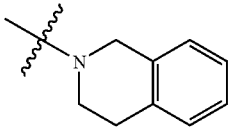 | 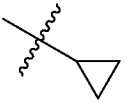 |

TABLE 1-continued

| Cmpd | R₂ | X | ZR₁ | R₈ | Q |
|---|---|---|---|---|---|
| W | NHBoc-methyl | NH | 4-fluoroisoindolin-2-yl | cyclopropyl | N(CH₂C(O)NMe₂)(cis-pent-3-enyl) |
| X | NHBoc-methyl | NH | 1,2,3,4-tetrahydroisoquinolin-2-yl | cyclopropyl | N(CH₂C(O)NMe₂)(cis-pent-3-enyl) |
| Y | NHBoc-methyl | O | naphthalen-2-yl | cyclopropyl | N(cyclopropyl)(cis-pent-3-enyl) |
| Z | NHBoc-methyl | O | phenyl | cyclopropyl | N(cyclopropyl)(cis-pent-3-enyl) |
| AA | NHBoc-methyl | O | naphthalen-1-yl | cyclopropyl | N(cyclopropyl)(cis-pent-3-enyl) |

TABLE 1-continued
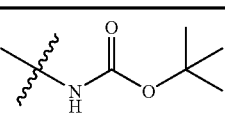
| Cmpd | R$_2$ | X | ZR$_1$ | R$_8$ | Q |
|---|---|---|---|---|---|
| BB | 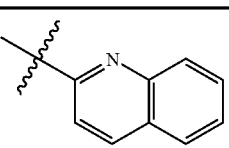 | O | 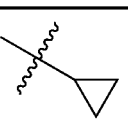 | 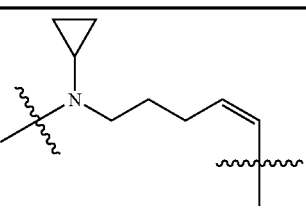 | 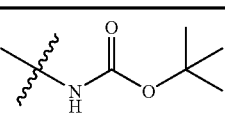 |
| CC | 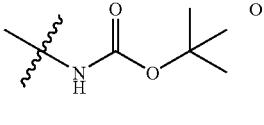 | O | 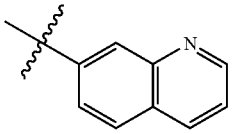 | 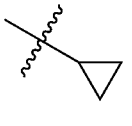 | 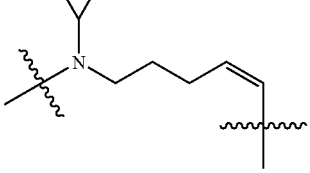 |
| DD | 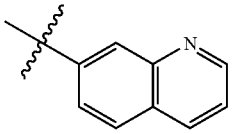 | O | 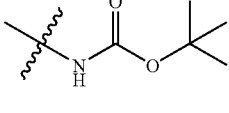 | 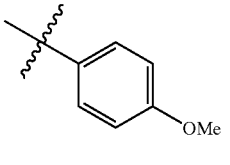 | 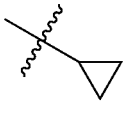 |
| EE | 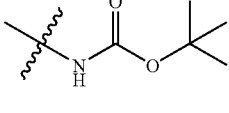 | O | 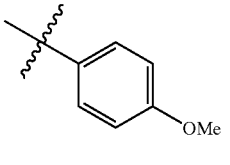 | 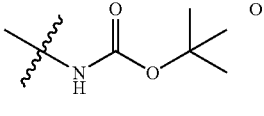 | 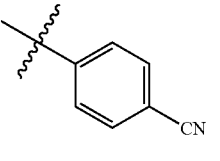 |
| FF | 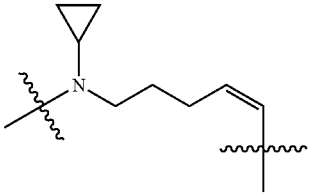 | O | 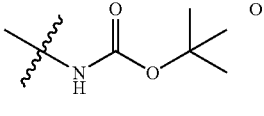 | 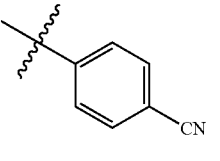 | 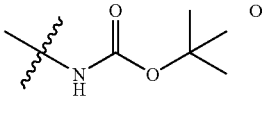 |
| GG | 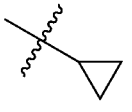 | O | 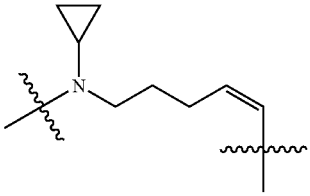 | 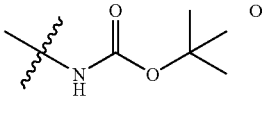 | 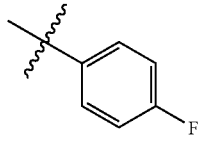 |

TABLE 1-continued

| Cmpd | R₂ | X | ZR₁ | R₈ | Q |
|---|---|---|---|---|---|
| HH | NHBoc-CH | O | 8-methoxyquinolin-3-yl | cyclopropyl | N(cyclopropyl)(pent-3-enyl) |
| II | NHBoc-CH | O | 5-(oxazol-2-yl)pyridin-2-yl | cyclopropyl | N(cyclopropyl)(pent-3-enyl) |
| JJ | NHBoc-CH | O | 4-(oxazol-2-yl)phenyl | cyclopropyl | N(cyclopropyl)(pent-3-enyl) |
| KK | NHBoc-CH | O | 4-(thiazol-2-yl)phenyl | cyclopropyl | N(cyclopropyl)(pent-3-enyl) |
| LL | NHBoc-CH | O | 5-(thiazol-2-yl)pyridin-2-yl | cyclopropyl | N(cyclopropyl)(pent-3-enyl) |

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J Virol. 72(8):6758-69 (1998)) with modifications. Briefly, the NS3/4A protease complex expression was induced with 0.5 mM Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride ($MgCl_2$), 1 µg/ml Dnasel, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 h at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat # 22991)(FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound was determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 micromolar ("µM") final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nM and excitation of 490 nM at 25° C. Reactions were generally followed for approximately 15 min.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y = A + ((B-A)/(1+((C/x)^0 D)))$.

All of the compounds tested were found to inhibit the activity of the NS3/4A protease complex with IC50's of 1.2 µM or less. Further, compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases, a 96-well plate format protocol using colorimetric p-nitroaniline (pNA) substrate or fluorometric Amino-Methyl-Coumarin (AMC) substrate, specific for each enzyme was used as described previously (PCT Patent Application No. WO 00/09543) with some modifications. All enzymes were purchased from Sigma or EMDbiosciences while the substrates were from Bachem.

Each pNA assay included a 2 h enzyme-inhibitor pre-incubation at room temperature followed by addition of substrate and hydrolysis to ~15% conversion as measured on a Spectramax Pro microplate reader. The cathepsin B assay was initiated by adding substrate to a 10 min enzyme-inhibitor pre-incubation at room temperature, and the assay plate measured immediately using the Cytofluor Series 4000. Compound concentrations varied from 100 to 0.4 µM depending on their potency.

The final conditions for each assay were as follows:

50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with:

133 µM succ-AAA-pNA and 20 nM HNE or 8 nM PPE; 100 µM succ-AAPF-pNA and 250 pM Chymotrypsin.

100 mM $NaHPO_4$ (Sodium Hydrogen Phosphate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 µM Z-FR-AMC diluted in $H_2O$.

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann V, Komer F, Koch J, Herian U, Theilmann L, Bartenschlager R., Science 285(5424):110-3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a $CC_{50}$ reading. The toxicity of compound ($CC_{50}$) was determined by adding $\frac{1}{10}^{th}$ volume of alamar Blue to the media incubating the cells.

After 4 hours, the fluorescence signal from each well was read, with an excitation wavelength at 530 nM and an emission wavelength of 580 nM, using the Cytofluor Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 µM final from a 2 mM stock in 100% DMSO. The HCV protease substrate. The plate was then placed into the Cytofluor 4000 instrument which had been set to 340 nM excitation/490 nM emission, automatic mode for 21 cycles and the plate read in a kinetic mode. $EC_{50}$ determinations were carried out as described for the $IC_{50}$ determinations.

HCV Replicon Luciferase Reporter Assay

As a secondary assay, $EC_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, J. Virol. 75(10):4614-4624 (2001)). The replicon construct described for our FRET assay was modified by inserting cDNA encoding a humanized form of the Renilla luciferase gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, Science 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% $CO_2$ incubator, cells were analyzed for Renilla Luciferase activity using the Promega Dual-Glo Luciferase Assay System. Media (100 µl) was removed from each well containing cells. To the remaining 50 µl of media, 50 µl of Dual-Glo Luciferase Reagent was added, and plates rocked for 10 minutes to 2 hours at room temperature. Dual-Glo Stop & Glo Reagent (50 µl) was then added to each well, and plates were rocked again for an additional 10 minutes to 2 h at room temperature. Plates were read on a Packard TopCount NXT using a luminescence program.

The percentage inhibition was calculated using the formula below:

$$\% \text{ control} = \frac{\text{average luciferase signal in experimental wells (+ compound)}}{\text{average luciferase signal in } DMSO \text{ control wells (− compound)}}$$

The values were graphed and analyzed using XLfit to obtain the $EC_{50}$ value.

Representative compounds of the disclosure were assessed in the HCV enzyme assays, HCV replicon cell assay and/or in several of the outlined specificity assays. For example, Compound 26 was found to have an $IC_{50}$ of 0.78 nanomolar (nM) against the NS3/4A BMS strain in the enzyme assay. Similar potency values were obtained with the published H77 ($IC_{50}$ of 0.53 nM) and J4L6S ($IC_{50}$ of 0.23 nM) strains. The $EC_{50}$ value in the replicon FRET assay was 7.3 nM, and 4.3 nM in the replicon Luciferase assay.

In the specificity assays, the same compound was found to have the following activity: HLE>100 µM; PPE>100 µM; Chymotrypsin>100 µM; Cathepsin B=100 µM. These results indicate this family of compounds are highly specific for the NS3 protease and many of these members inhibit HCV replicon replication.

The compounds of the current disclosure were tested and found to have activities in the ranges as follow:

$IC_{50}$ Activity Ranges (NS3/4A BMS Strain): A is >1 micromolar (µM); B is 0.1-1 µM; C is <0.1 µM $EC_{50}$ Activity Range (for compounds tested): A is >1 µM; B is 0.1-1 µM; C is <0.1 µM Note that by using the patent compound number shown in Table 1 the structures of compounds can be found herein.

In accordance with one embodiment of the present disclosure, the compounds have a biological activity ($EC_{50}$) of 100 µM or less, and in another embodiment, 1 µM or less, and most preferably 0.1 µM or less.

| Patent Compound Number | IC50 Range | EC50 Range |
|---|---|---|
| Compound 1 | C | B |
| Compound 2 | C | A |
| Compound 3 | C | A |
| Compound 4 | C | A |
| Compound 5 | C | A |
| Compound 6 | C | A |
| Compound 7 | C | A |
| Compound 8 | C | B |
| Compound 9 | C | B |
| Compound 10 | C | B |
| Compound 11 | C | C |
| Compound 12 | C | B |
| Compound 13 | C | B |
| Compound 14 | B | B |
| Compound 15 | C | C |
| Compound 16 | C | C |
| Compound 17 | C | C |
| Compound 18 | C | C |
| Compound 19 | C | C |
| Compound 20 | C | C |
| Compound 21 | C | C |
| Compound 22 | C | C |
| Compound 23 | C | C |
| Compound 24 | C | C |
| Compound 25 | C | C |
| Compound 26 | C | C |
| Compound 27 | C | A |
| Compound 28 | C | A |
| Compound 29 | C | C |
| Compound 30 | C | A |
| Compound 31 | C | C |
| Compound 32 | C | C |
| Compound 33 | C | B |
| Compound 34 | C | A |
| Compound 35 | C | B |
| Compound 36 | B | A |
| Compound 37 | B | A |
| Compound 38 | C | B |
| Compound 39 | A | |
| Compound 40 | B | B |
| Compound 41 | A | A |
| Compound 42 | C | B |
| Compound 43 | C | C |
| Compound 44 | C | B |
| Compound 45 | C | B |
| Compound 46 | C | C |
| Compound 47 | A | |
| Compound 48 | C | C |

-continued

| Patent Compound Number | IC50 Range | EC50 Range |
|---|---|---|
| Compound 49 | C | C |
| Compound 50 | C | C |
| Compound 51 | C | C |
| Compound 52 | C | C |
| Compound 53 | C | C |
| Compound 54 | C | C |

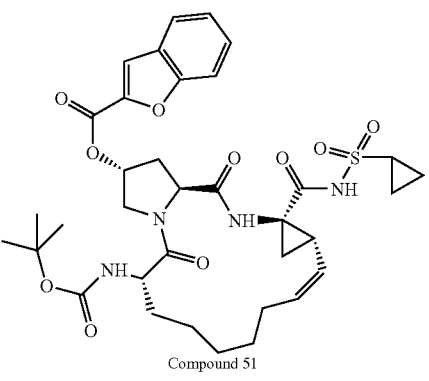

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (V)

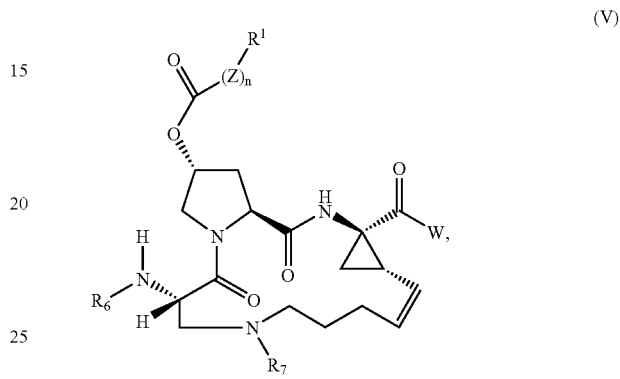

or a pharmaceutically acceptable salt thereof, wherein
$R^1$ is aryl;
$R^6$ is selected from alkoxycarbonyl, cycloalkoxycarbonyl, alkylaminocarbonyl, and alkylcarbonyl;
$R^7$ is selected from hydrogen, alkoxy, alkoxycarbonyl, alkyl, cycloalkyl, and dialkylaminocarbonyl;
W is —NHSO$_2$R$^8$; wherein R$^8$ is selected from: cycloalkyl optionally substituted with alkyl and alkoxy; heterocyclyl; and —NR$^a$R$^b$; wherein R$^a$ and R$^b$ are independently selected from hydrogen, and alkyl; and
n is 0.

2. A composition comprising the compound of claim 1 and a pharmaceutically acceptable carrier.

3. The composition according to the claim 2 further comprising at least one of an interferon and ribavirin.

4. The composition according to claim 2 further comprising a second compound having anti-HCV activity.

5. The composition according to claim 4 wherein the second compound having anti-HCV activity is an interferon.

6. The composition according to claim 5 wherein the interferon is selected from interferon alpha 2B, pegylated interferon alpha, consensus interferon, interferon alpha 2A, and lymphoblastiod interferon tau.

7. The composition according to claim 4 wherein the second compound having anti-HCV activity is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

8. The composition according to claim 4 wherein the second compound having anti-HCV activity is a small molecule compound.

9. The composition according to claim 4 wherein the second compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

10. A method of inhibiting the function of HCV serine protease comprising contacting the HCV serine protease with the compound of claim 1.

11. A method of treating an HCV infection in a patient, comprising administering to the patient a therapeutically effective amount of the compound of claim 1.

12. The method of claim 11 wherein the compound is effective to inhibit the function of the HCV serine protease.

13. The method of claim 10 further comprising administering a second compound having anti-HCV activity.

14. The method of claim 13 wherein the second compound having anti-HCV activity is an interferon.

15. The method of claim 14 wherein the interferon is selected from interferon alpha 2B, pegylated interferon alpha, consensus interferon, interferon alpha 2A, and lymphoblastiod interferon tau.

16. The method of claim 13 wherein the second compound having anti-HCV activity is selected from interleukin 2, interleukin 6, interleukin 12, a compound that enhances the development of a type 1 helper T cell response, Imiqimod, ribavirin, an inosine 5'-monophospate dehydrogenase inhibitor, amantadine, and rimantadine.

17. The method of claim 13 wherein the second compound having anti-HCV activity is a small molecule.

18. The method of claim 13 wherein the second compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

19. The method of claim 13 wherein the second compound having anti-HCV activity is effective to inhibit the function of target in the HCV life cycle other than the HCV serine protease.

* * * * *

UNITED STATES PATENT AND TRADEMARK OFFICE
CERTIFICATE OF CORRECTION

| | |
|---|---|
| PATENT NO. | : 7,772,183 B2 |
| APPLICATION NO. | : 11/546505 |
| DATED | : August 10, 2010 |
| INVENTOR(S) | : David J. Carini et al. |

Page 1 of 1

It is certified that error appears in the above-identified patent and that said Letters Patent is hereby corrected as shown below:

In the Specification:

Column 13, line 51, change "lymphoblastiod" to -- lymphoblastoid --.
Column 13, line 62, change "Imiqimod" to -- Imiquimod --.
Column 13, line 62, change "5′-monophospate" to -- 5′-monophosphate --.
Column 14, line 28, change "lymphoblastiod" to -- lymphoblastoid --.
Column 14, line 52, change "Imiqimod" to -- Imiquimod --.
Column 14, line 52, change "5′-monophospate" to -- 5′-monophosphate --.
Column 33, lines 3 and 4, change "lymphoblastiod" to -- lymphoblastoid --.
Column 33, line 8, change "Imiqimod" to -- Imiquimod --.
Column 33, line 9, change "5′-monophospate" to -- 5′-monophosphate --.

In the Claims:

Claim 6:
    Column 160, line 51, change "lymphoblastiod" to -- lymphoblastoid --.

Claim 7:
    Column 160, line 56, change "Imiqimod" to -- Imiquimod --.
    Column 160, line 56, change "5′-monophospate" to -- 5′-monophosphate --.

Claim 15:
    Column 161, lines 15 and 16, change "lymphoblastiod" to -- lymphoblastoid --.

Claim 16:
    Column 162, line 2, change "Imiqimod" to -- Imiquimod --.
    Column 162, line 3, change "5′-monophospate" to -- 5′-monophosphate --.

Signed and Sealed this
Twenty-eighth Day of August, 2012

David J. Kappos
*Director of the United States Patent and Trademark Office*